United States Patent [19]

Pieper et al.

[11] Patent Number: 5,994,356

[45] Date of Patent: *Nov. 30, 1999

[54] CARBOXYLIC ACID DERIVATIVES, MEDICAMENTS COMPRISING THESE COMPOUNDS, THEIR USE AND PROCESSES FOR THEIR PRODUCTION

[75] Inventors: Helmut Pieper, Biberach; Günter Linz, Mittelbiberach; Volkhard Austel, Biberach; Frank Himmelsbach, Mittelbiberach; Brian Guth, Warthausen; Johannes Weisenberger, Biberach, all of Germany

[73] Assignee: Karl Thomae, Biberach, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/832,259

[22] Filed: Apr. 3, 1997

[30] Foreign Application Priority Data

Apr. 10, 1996 [DE] Germany ............... 196 14 204

[51] Int. Cl.$^6$ ............ A61K 31/495; C07D 403/06; C07D 403/12; C07D 403/14

[52] U.S. Cl. ............ 514/252; 514/269; 514/329; 514/316; 514/317; 544/239; 544/298; 544/336; 544/360; 544/364; 546/187; 546/191; 546/223; 546/224

[58] Field of Search ............ 514/329, 316, 514/318, 327, 328, 252, 269; 544/239, 298, 336, 360, 364; 546/187, 188, 194, 191, 223, 224, 225

[56] References Cited

U.S. PATENT DOCUMENTS 5,227,490   7/1993   Hartman ................. 514/317

5,652,242   7/1997   Wayne ................... 514/255

FOREIGN PATENT DOCUMENTS 0 528 369 A2   2/1993   European Pat. Off. .
0 638 553 A1   2/1994   European Pat. Off. .
0 604 800 A1   7/1994   European Pat. Off. .

Primary Examiner—Evelyn Mei Huang
Attorney, Agent, or Firm—Robert P. Raymond; Alan R. Stempel; Mary-Ellen M. Devlin

[57] ABSTRACT

The present invention relates to carboxylic acid derivatives of the general formula

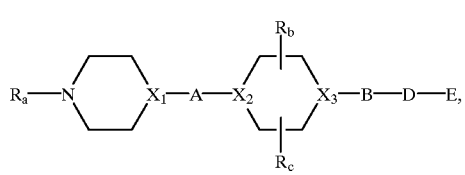

in which $R_a$ to $R_c$, A, B, D, E and $X_1$ to $X_3$ are as defined in claim 1, their tautomers, their stereoisomers including their mixtures, and their salts, in particular their physiologically tolerated salts with inorganic or organic acids or bases, which have useful pharmacological properties, preferably aggregation-inhibiting inhibiting actions, medicaments containing these compounds, their use and processes for their preparation.

9 Claims, No Drawings

CARBOXYLIC ACID DERIVATIVES, MEDICAMENTS COMPRISING THESE COMPOUNDS, THEIR USE AND PROCESSES FOR THEIR PRODUCTION

The present invention relates to carboxylic acid derivatives of the general formula

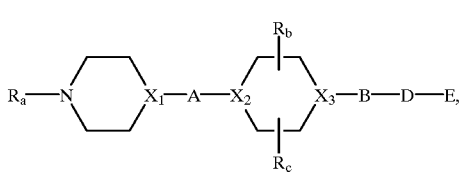

their tautomers, their stereoisomers, including their mixtures, and their salts, in particular their salts with physiologically tolerated acids or bases, which have useful pharmacological properties, preferably aggregation-inhibiting actions, medicaments comprising these compounds and their use, and processes for their production.

In the above general formula I $R_a$ is a hydrogen atom, a $C_{1-5}$-alkyl or phenyl-$C_{1-3}$-alkyl group, in which in each case the alkyl moiety can be substituted by a carboxyl, $C_{1-3}$-alkoxycarbonyl, aminocarbonyl, N-$C_{1-3}$-alkylamino-carbonyl, N,N-di($C_{1-3}$-alkyl)aminocarbonyl, vinyl or ethynyl group or alternatively, if the abovementioned substituents are not on an α-carbon atom adjacent to a nitrogen atom, by a hydroxyl, $C_{1-3}$-alkoxy, amino, $C_{1-3}$-alkylamino or di($C_{1-3}$-alkyl)amino group, or is a radical which can be cleaved in vivo, $R_b$ and $R_c$, which can be identical or different, in each case are a hydrogen atom or the side chain of a natural D- or L-α-amino acid, and their esters and ethers, A is an —$HCR_1$—$HCR_2$-, —CO—$HCR_1$—, —$HCR_1$—CO—, —$NR_3$—$HCR_1$—, —$HCR_1$—$NR_3$—, —$NR_2$—CO—, —CO—$NR_2$—, —O—CO—, —CO—O—, —O—$HCR_1$— or —$CHR_1$—O— group, in which $R_1$ is a hydrogen atom, a $C_{1-3}$-alkyl, phenyl-$C_{1-3}$-alkyl or phenyl group, $R_2$ is a hydrogen atom, a $C_{1-3}$-alkyl or phenyl-$C_{1-3}$-alkyl group and $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$, $X_2$ and $X_3$, which can be identical or different, in each case are a nitrogen atom or a methine group, it additionally in each case being possible in the abovementioned heterocyclic rings in which $X_2$ or $X_3$ or $X_2$ and $X_3$ are each a nitrogen atom for a methylene group linked to a ring nitrogen atom to be replaced by a carbonyl group, B is a 3-piperidinylene, 4-piperidinylene or 1,4-piperazinylene group, in which in each case a methylene group adjacent to a nitrogen atom can be replaced by a carbonyl group, it additionally being possible for a 1,4-piperazinylene group to be substituted by $R_b$ and $R_c$, and $R_b$ and $R_c$ being defined as mentioned above, or a phenylene, cyclohexylene, pyridinylene, pyridazinylene, pyrimidinylene or pyrazinylene group, D is an —O—$R_1CR_4$—CO—, —$NR_3$—$HCR_1$—CO—, —$NR_3$—$CH_2CH_2CO$—, —$CH_2CO$—, —$CHR_1CH_2CO$— or (—O—)$_2$CH—CO— group, in which $R_1$ and $R_3$ are defined as mentioned above and $R_4$ is a hydrogen atom, a $C_{1-3}$-alkyl, hydroxy-$C_{1-3}$-alkyl, carboxy-$C_{1-3}$-alkyl, $C_{1-3}$-alkoxycarbonyl-$C_{1-3}$-alkyl, $C_{3-7}$-cycloalkoxycarbonyl-$C_{1-3}$-alkyl, phenyl-$C_{1-3}$-alkyl, phenyl, pyridyl-$C_{1-3}$-alkyl or pyridyl group, and E is a hydroxyl group, an alkoxy group having 1 to 6 carbon atoms, a phenylalkoxy group in which the alkoxy moiety can contain 1 to 3 carbon atoms, a cycloalkoxy group having 3 to 9 carbon atoms in which the cycloalkyl moiety having 5 to 8 carbon atoms can additionally be substituted by one or two alkyl groups each having 1 to 3 carbon atoms, a cycloalkoxy group having 5 to 8 carbon atoms in which in the cycloalkyl moiety a methylene group in the 3- or 4-position is replaced by an oxygen atom or by an imino group which is optionally substituted by an alkyl, phenylalkyl or phenylalkoxycarbonyl group, in which the alkyl and alkoxy moiety can each contain 1 to 3 carbon atoms, or by an alkanoyl group having 2 to 6 carbon atoms, and the cycloalkyl moiety can additionally be substituted by one or two alkyl groups each having 1 to 3 carbon atoms, or is a cycloalkenyloxy group in which the cycloalkenyl moiety can contain 4 to 7 carbon atoms, an alkenyloxy, phenylalkenyloxy, alkynyloxy or phenylalkynyloxy group with the proviso that a bond to the oxygen atom does not start from a carbon atom which carries a double or triple bond and in which the alkenyl and alkynyl moiety can each contain 3 to 5 carbon atoms, a cycloalkylalkoxy group in which the cycloalkyl moiety can contain 3 to 8 carbon atoms and the alkoxy moiety 1 to 3 carbon atoms, a bicycloalkoxy group having a total of 8 to 10 carbon atoms, which in the bicycloalkyl moiety can additionally be substituted by one or two alkyl groups each having 1 to 3 carbon atoms, a 1,3-dihydro-3-oxo-1-isobenzofuranyloxy group or an $R_7$—CO—O—($R_5CR_6$)—O group, in which $R_5$ is a hydrogen atom, a $C_{1-6}$-alkyl, $C_{3-7}$-cycloalkyl or phenyl group, $R_6$ is a hydrogen atom or a $C_{1-6}$-alkyl group and $R_7$ is a $C_{1-5}$-alkyl, $C_{1-5}$-alkoxy, $C_{5-7}$-cycloalkyl or $C_{5-7}$-cycloalkoxy group, or E is an α-amino group of a natural D- or L-amino acid and their esters.

The expressions "a phenyl group" or "a phenylene group" mentioned in the definition of the above radicals is in each case in particular understood as meaning a phenyl or phenylene group which is optionally mono-, di- or trisubstituted by fluorine, chlorine, bromine or iodine atoms, by $C_{1-3}$-alkyl, trifluoromethyl, nitro, amino, $C_{1-3}$-alkylamino, di($C_{1-3}$-alkyl)amino, $C_{1-4}$-alkanoylamino, hydroxyl, $C_{1-3}$-alkoxy, carboxyl, $C_{1-3}$-alkoxycarbonyl, $C_{3-7}$-cycloalkoxycarbonylalkoxy, hydroxycarbonyl-$C_{1-3}$-alkoxy, $C_{1-3}$-alkoxycarbonyl-$C_{1-3}$-alkoxy, aminocarbonyl, $C_{1-3}$-alkylaminocarbonyl or di($C_{1-3}$-alkyl)aminocarbonyl groups, it being posisble for the substituents to be identical or different, the esters of a natural α-amino acid are understood as meaning its $C_{1-6}$-alkyl, $C_{2-6}$-alkenyl, $C_{5-7}$-cycloalkyl, phenyl or phenyl-$C_{1-3}$-alkyl esters such as the methyl, ethyl, n-propyl, isopropyl, tert-butyl, allyl, phenyl or benzyl ester, the ethers of the side chain of a natural D- or L-α-amino acid are understood as meaning its $C_{1-5}$-alkyl, phenyl-$C_{1-3}$-alkyl, phenyl or $C_{4-7}$-cycloalkyl ether and a radical which can be cleaved in vivo is understood as meaning an alkanoyl group having a total of 1 to 6 carbon atoms, a benzoyl, allyloxycarbonyl, $C_{1-5}$- alkoxycarbonyl or phenyl-$C_{1-3}$-alkoxycarbonyl group such as the formyl, acetyl, propionyl, butanoyl, pentanoyl, hexanoyl, benzoyl, allyloxycarbonyl, methoxycarbonyl, ethoxycarbonyl, propoxycarbonyl, isopropoxycarbonyl, butoxycarbonyl, tert-butoxycarbonyl, pentoxycarbonyl, hexoxycarbonyl, benzyloxycarbonyl, phenylethoxycarbonyl or phenyl-propoxycarbonyl group.

Preferred compounds of the above general formula I are those in which $R_a$ is a hydrogen atom, a $C_{1-5}$-alkyl or phenyl-$C_{1-3}$-alkyl group in which in each case the alkyl moiety can be substituted by a carboxyl, $C_{1-3}$-alkoxycarbonyl, aminocarbonyl, N-$C_{1-3}$-alkylaminocarbonyl, N,N-di($C_{1-3}$-alkyl)aminocarbonyl, vinyl or ethynyl group or alternatively, if the abovementioned substituents are not on an α-carbon atom adjacent to a nitrogen atom, by a hydroxyl, $C_{1-3}$-alkoxy, amino, $C_{1-3}$-alkylamino or di($C_{1-3}$-alkyl)amino group, or is a radical which can be cleaved in vivo, $R_b$ and $R_c$, which can be identical or different, are each a hydrogen atom or the side chain of a natural D- or L-α-amino acid, and their esters and ethers, A is an —$HCR_1$—$HCR_2$—, —CO—$HCR_1$—, —$HCR_1$—CO—, —$NR_3$—$HCR_1$—, —$HCR_1$—$NR_3$—, —$NR_2$—CO—, —CO—$NR_2$—, —O—CO—, —CO—O, —O—$HCR_1$— or —$CHR_1$—O— group, in which $R_1$ is a hydrogen atom, a $C_{1-3}$-alkyl, phenyl-$C_{1-3}$-alkyl or phenyl group, $R_2$ is a hydrogen atom, a $C_{1-3}$-alkyl or phenyl-$C_{1-3}$-alkyl group and $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$, $X_2$ and $X_3$, which can be identical or different, are each a nitrogen atom or a methine group, it additionally in each case being possible in the abovementioned heterocylic rings in which $X_2$ or $X_3$ or $X_2$ and $X_3$ are each a nitrogen atom for a methylene group linked to a ring nitrogen atom to be replaced by a carbonyl group, B is a 3-piperidinylene, 4-piperidinylene or 1,4-piperazinylene group in which in each case a methylene group adjacent to a nitrogen atom can be replaced by a carbonyl group, it additionally being possible for a 1,4-piperazinylene group to be substituted by $R_b$ and $R_c$, and $R_b$ and $R_c$ being defined as mentioned above, or a phenylene, cyclohexylene or pyridazinylene group, D is an —O—$R_1CR_4$—CO—, —$NR_3$—$HCR_1$—CO—, —$NR_3$—$CH_2CH_2CO$—, —$CH_2CO$—, —$CHR_1CH_2CO$— or (—O—)$_2$CH—CO— group, in which $R_1$ and $R_3$ are defined as mentioned above and $R_4$ is a hydrogen atom, a $C_{1-3}$-alkyl, hydroxy-$C_{1-3}$-alkyl, carboxy-$C_{1-3}$-alkyl, $C_{1-3}$-alkoxycarbonyl-$C_{1-3}$-alkyl, $C_{3-7}$-cycloalkoxycarbonyl-$C_{1-3}$-alkyl, phenyl-$C_{1-3}$-alkyl, phenyl, pyridyl-$C_{1-3}$-alkyl or pyridyl group, and E is a hydroxyl, $C_{1-6}$-alkoxy, $C_{3-9}$-cycloalkoxy, phenyl-$C_{1-3}$-alkoxy or $R_7$—CO—O—($R_5CR_6$)—O— group, in which $R_5$ is a hydrogen atom, a $C_{1-6}$-alkyl, $C_{3-7}$-cycloalkyl or phenyl group, $R_6$ is a hydrogen atom or a $C_{1-6}$-alkyl group and $R_7$ is a $C_{1-5}$-alkyl, $C_{1-5}$-alkoxy, $C_{5-7}$-cycloalkyl or $C_{5-7}$-cycloalkoxy group, the expressions A "a phenyl group" or "a phenylene group" mentioned in the definitions of the above radicals in each case in particular being understood as meaning a phenyl or phenylene group which is optionally mono-, di- or trisubstituted by fluorine, chlorine, bromine or iodine atoms, by $C_{1-3}$-alkyl, trifluoromethyl, nitro, amino, $C_{1-3}$-alkylamino, di($C_{1-3}$-alkyl)amino, $C_{1-4}$-alkanoylamino, hydroxyl, $C_{1-3}$-alkoxy, carboxyl, $C_{1-3}$-alkoxycarbonyl, $C_{3-7}$-cycloalkoxycarbonylalkoxy, hydroxycarbonyl-$C_{1-3}$-alkoxy, $C_{1-3}$-alkoxycarbonyl-$C_{1-3}$-alkoxy, aminocarbonyl, $C_{1-3}$-alkylaminocarbonyl or di($C_{1-3}$-alkyl)aminocarbonyl groups, it being possible for the substituents to be identical or different, the esters of a natural α-amino acid are understood as meaning its $C_{1-6}$-alkyl, $C_{2-6}$-alkenyl, $C_{5-7}$-cycloalkyl, phenyl or phenyl-$C_{1-3}$-alkyl esters such as the methyl, ethyl, n-propyl, iso-propyl, tert-butyl, allyl, phenyl or benzyl ester, the ethers of the side chain of a natural D- or L-α-amino acid are understood as meaning its $C_{1-5}$-alkyl, phenyl-$C_{1-3}$-alkyl, phenyl or $C_{4-7}$-cycloalkyl ether and a radical which can be cleaved in vivo is understood as meaning an alkanoyl group having a total of 1 to 6 carbon atoms, a benzoyl, allyloxycarbonyl, $C_{1-5}$-alkoxycarbonyl or phenyl-$C_{1-3}$-alkoxycarbonyl group such as the formyl, acetyl, propionyl, butanoyl, pentanoyl, hexanoyl, benzoyl, allyloxycarbonyl, methoxycarbonyl, ethoxycarbonyl, propoxycarbonyl, isopropoxycarbonyl, butoxycarbonyl, tert-butoxycarbonyl, pentoxycarbonyl, hexoxycarbonyl, benzyloxycarbonyl, phenylethoxycarbonyl or phenyl-propoxycarbonyl group, their tautomers, their stereoisomers, including their mixtures, and their salts.

Particularly preferred compounds of the above general formula I are those in which $R_a$ is a hydrogen atom, a $C_{1-3}$-alkyl, phenyl-$C_{1-3}$-alkyl, $C_{1-5}$-alkoxycarbonyl or phenyl-$C_{1-3}$-alkoxycarbonyl group, $R_b$ and $R_c$, which can be identical or different, are each a hydrogen atom or the side chain of a natural D- or L-α-amino acid, and its esters and ethers, A is a —$CH_2CH_2$—, —CO—$CH_2$—, —$CH_2$—CO—, —$CH_2$—$NR_3$—, —$NR_3$—$CH_2$—, —NH—CO—, —O—CO— or —$CH_2$—O— group, in which $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$, $X_2$ and $X_3$, which can be identical or different, are each a nitrogen atom or a methine group, it additionally in each case being possible in the abovementioned heterocylic rings in which $X_2$ or $X_3$ or $X_2$ and $X_3$ are each a nitrogen atom for a methylene group linked to a ring nitrogen atom to be replaced by a carbonyl group, B is a 4-piperidinylene group or a 1,4-piperazinylene group in which a methylene group adjacent to a nitrogen atom can be replaced by a carbonyl group, it additionally being possible for the abovementioned 1,4-piperazinylene groups to be substituted by a carboxymethyl or $C_{1-5}$-alkoxycarbonyl group, or is a 1,3- or 1,4-phenylene group which is optionally substituted by an E—CO—$CH_2$— group, E being defined as below, or a 1,4-cyclohexylene or 2,5-pyridazinylene group, D is an —O—$R_1CR_4$—CO—, —$CH_2CO$—, —$CHR_1CH_2CO$—, —$NR_3CH_2CO$— or (—O—)$_2$CH—CO— group, in which $R_3$ is defined as mentioned above, $R_1$ is a hydrogen atom or a $C_{1-3}$-alkyl group and $R_4$ is a hydrogen atom, a $C_{1-3}$-alkyl, hydroxy-$C_{1-2}$-alkyl, carboxymethyl, benzyl, chlorobenzyl or phenyl group, and E is a hydroxyl, $C_{1-6}$-alkoxy, $C_{3-9}$-cycloalkoxy or phenyl-$C_{1-3}$-alkoxy group, the esters of a natural α-amino acid in the definition of the abovementioned radicals being understood as meaning its $C_{1-6}$-alkyl, $C_{2-6}$-alkenyl, $C_{5-7}$-cycloalkyl, phenyl or phenyl-$C_{1-3}$-alkyl esters such as the methyl, ethyl, n-propyl, isopropyl, tert-butyl, allyl, phenyl or benzyl ester and the ethers of the side chain of a natural D- or L-α-amino acid being understood as meaning its $C_{1-5}$-alkyl, phenyl-$C_{1-3}$-alkyl, phenyl or $C_{4-7}$-cycloalkyl ether, their tautomers, their stereoisomers, including their mixtures, and their salts.

Very particularly preferred compounds of the above general formula I are those in which $R_a$ is a hydrogen atom, a benzyl, $C_{1-5}$-alkoxycarbonyl or benzyloxycarbonyl group, $R_b$ and $R_c$, which can be identical or different, are each a hydrogen atom or the side chain of a natural D- or L-α-amino acid, and its esters and ethers, A is a —$CH_2CH_2$—, —CO—$CH_2$—, —$CH_2$—CO—, —$CH_2$—$NR_3$—, —$NR_3$—$CH_2$— or —NH—CO— group, in which $R_3$ is a hydrogen atom, a methyl, benzyl, acetyl or n-butylsulphonyl group, $X_1$, $X_2$ and $X_3$, which can be identical or different, are each a nitrogen atom or a methine group, it additionally in each case being possible in the abovementioned heterocylic rings in which $X_2$ or $X_3$ or $X_2$ and $X_3$ are each a nitrogen atom for a methylene group linked to a ring nitrogen atom to be replaced by a carbonyl group, B is a 4-piperidinylene group or a 1,4-piperazinylene group in which a methylene group adjacent to a nitrogen atom can be replaced by a carbonyl group, it additionally being possible for the abovementioned 1,4-piperazinylene groups to be substituted by a carboxymethyl or $C_{1-5}$-alkoxycarbonyl group, or is a 1,3- or 1,4-phenylene group which is optionally substituted by an E—CO—$CH_2$— group, E being defined as below, or a 1,4-cyclohexylene or 2,5-pyridazinylene group, D is an —O—$R_1$CH—CO—, —O— ($CH_3CCH_3$)—CO—, —$CH_2CH_2$CO—, —(CH$CH_3$)$CH_2$CO—, —$NR_3CH_2$CO— or (—O—)$_2$CH—CO— group, in which $R_3$ is defined as mentioned above and $R_1$ is a hydrogen atom, methyl, 2-hydroxyethyl, carboxymethyl, benzyl, chlorobenzyl or phenyl group, and E is a hydroxyl, $C_{1-6}$-alkoxy, $C_{3-9}$-cycloalkoxy or phenyl-$C_{1-3}$-alkoxy group, the esters of a natural α-amino acid in the definition of the abovementioned radicals being understood as meaning its $C_{1-6}$-alkyl, $C_{2-6}$-alkenyl, $C_{5-7}$-cycloalkyl, phenyl or phenyl-$C_{1-3}$-alkyl esters such as the methyl, ethyl, n-propyl, isopropyl, tert-butyl, allyl, phenyl or benzyl ester and the ethers of the side chain of a natural D- or L-α-amino acid being understood as meaning its $C_{1-5}$-alkyl, phenyl-$C_{1-3}$-alkyl, phenyl or $C_{4-7}$-cycloalkyl ether, their tautomers, their stereoisomers, including their mixtures, and their salts.

For example, the following particularly preferred compounds of the general formula I may be mentioned:

(1) 1-(4-carboxymethyloxyphenyl)-4-[2-(piperidin-4-yl)ethyl]piperazine, (2) 1-(4-carboxymethyloxyphenyl)-4-[2-(piperidin-4-yl)ethyl]piperazin-2-one, (3) 1-[3,4-di(carboxymethyloxy)phenyl]-4-[2-(piperidin-4-yl)ethyl]piperazine, (4) 1-(4-carboxymethyloxyphenyl)-2-methyl-4-[2-(piperidin-4-yl)ethyl]piperazine, (5) trans-1-(4-carboxymethyloxyphenyl)-4-[(piperidin-4-yl)-N-methylmethylamino]cyclohexane, (6) 1-(trans-4-carboxymethyloxycyclohexyl)-4-[2-(piperidin-4-yl)ethyl]piperazin-2-one, (7) 1-[4-(1-carboxybenzyloxy)phenyl]-4-[2-(piperidin-4-yl)ethyl]piperazine, their $C_{1-4}$-alkyl, cyclopentyl and cyclohexyl esters, their stereoisomers, including their mixtures, and their salts, but in particular the compounds 1-(4-cyclohexyloxycarbonylmethyloxyphenyl)-4-[2-(piperidin-4-yl)ethyl]piperazine and 1-[3,4-di(cyclopentyloxycarbonylmethyloxy)phenyl]-4-[2-(piperidin-4-yl)ethyl]piperazine and their salts.

a) To prepare a compound of the general formula I in which $R_a$ is defined as at the beginning and E is a hydroxyl group or E, with the exception of the hydroxyl and $R_7$—CO—O—($R_5CR_6$)—O— group, is as defined at the beginning and $R_a$ is a hydrogen atom:

conversion of a compound of the general formula

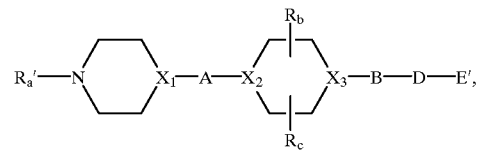

(II)

in which $R_b$, $R_c$, A, B, D and $X_1$ to $X_3$ with the proviso are as defined in the beginning that E' has the meanings mentioned for E at the beginning and $R_a'$ is a protective radical for an imino group which can be removed by means of hydrolysis, treatment with an acid or base, thermolysis or hydrogenolysis or $R_a'$ has the meanings mentioned for $R_a$ at the beginning and E' is a group which can be converted into a hydroxyl group by means of hydrolysis, treatment with an acid or base, thermolysis or hydrogenolysis, into a compound of the general formula I, in which $R_a$ is as defined at the beginning and E is a hydroxyl group or E, with the exception of the hydroxyl and $R_7$—CO—O—($R_5CR_6$)—O— group, is as defined at the beginning and $R_a$ is a hydrogen atom.

As protective groups for a hydroxyl group of a carboxyl group, for example, the functional derivatives of a carboxyl group such as its unsubstituted or substituted amides, esters, thioesters, trimethylsilyl esters, orthoesters or iminoesters can be converted into a carboxyl group by means of hydrolysis, esters with tertiary alcohols, e.g. the tert-butyl ester, can be converted into a carboxyl group by means of treatment with an acid or thermolysis and esters with aralkanols, e.g. the benzyl ester, can be converted into a carboxyl group by means of hydrogenolysis.

The hydrolysis is expediently carried out either in the presence of an acid such as hydrochloric acid, sulphuric acid, phosphoric acid, acetic acid, trichloroacetic acid, trifluoroacetic acid or their mixtures or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between –10 and 120° C., e.g. at temperatures between room temperature and the boiling temperature of the reaction mixture.

Under the abovementioned reaction conditions, N-acylamino or $C_{1-5}$-alkoxycarbonylamino groups which may be present, such as an N-trifluoroacetylamino or tert-butyloxycarbonylamino group, can be converted into the corresponding amino groups.

If E' in a compound of the general formula II is, for example, the tert-butyloxy group and/or $R_a'$ is the tert-butyloxycarbonyl group, these groups can also be removed by treatment with an acid such as trifluoroacetic acid, formic acid, p-toluenesulphonic acid, sulphuric acid, hydrochloric acid, phosphoric acid or polyphosphoric acid, if appropriate in an inert solvent such as methylene chloride, chloroform, benzene, toluene, diethyl ether, tetrahydrofuran or dioxane, preferably at temperatures between –10 and 120° C., e.g. at temperatures between 0 and 60° C., or alternatively thermally, if appropriate in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C. Under the abovementioned reaction conditions, N-tert-butyloxycarbonylamino groups which may be present can be converted into the corresponding amino groups.

If E' in a compound of the formula II is, for example, the benzyloxy group and/or $R_a'$ is the benzyl group, these groups can also be removed hydrogenolytically in the presence of a hydrogenation catalyst such as palladium/carbon in a suitable solvent such as methanol, ethanol, ethanol/water, glacial acetic acid, ethyl acetate, dioxane or dimethylformamide, preferably at temperatures between 0 and 50° C., e.g. at room temperature, and at a hydrogen pressure of 1 to 5 bar. During the hydrogenolysis, other radicals can simultaneously be converted, e.g. a nitro group into an amino group, a benzyloxy group into a hydroxyl group and an N-benzylamino, N-benzylimino, N-benzyloxycarbonylamino or N-benzyloxycarbonylimino group into a corresponding amino or imino group.

b) For the preparation of a compound of the general formula I in which $X_2$ is a nitrogen atom and A is an —HCR$_1$—HCR$_2$—, —CO—HCR$_1$— or —HCR$_1$—CO— group:

reaction of a compound of the general formula

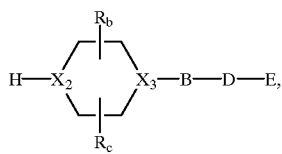

(III)

in which $R_b$, $R_c$, $X_3$, B, D and E are as defined at the beginning and $X_2$ is a nitrogen atom, with a compound of the general formula

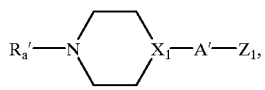

(IV)

in which $X_1$ is as defined at the beginning, and $R_a'$, with the exception of the hydrogen atom, has the meanings mentioned for $R_a$ at the beginning or is a protective radical for an imino group, A' is —HCR$_1$—HCR$_2$—, —CO—HCR$_1$— or —HCR$_1$—CO— group, $R_1$ and $R_2$ being as defined at the beginning, and $Z_1$ is a hydroxyl group or a nucleofugic leaving group such as a halogen atom, e.g. a chlorine, bromine or iodine atom, a sulphonic acid ester group, e.g. a methanesulphonyloxy or p-toluenesulphonyloxy group, an imidazolyl, triazolyl or 4-nitrophenyloxy group and, if appropriate, subsequent removal of a protective radical used.

The reaction is preferably carried out in a solvent such as methanol, ethanol, methylene chloride, tetrahydrofuran, toluene, dioxane, dimethyl sulphoxide or dimethylformamide, if appropriate in the presence of an inorganic or of a tertiary organic base or if appropriate in the presence of an agent which dehydrates or activates the acid, at temperatures between –30 and 200° C.

The reaction of a carboxylic acid of the general formula IV is optionally carried out in a solvent or solvent mixture such as methylene chloride, dimethylformamide, benzene, toluene, chlorobenzene, tetrahydrofuran, benzene/tetrahydrofuran or dioxane or in an appropriate amine of the general formula III, if appropriate in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and if appropriate with addition of a base such as pyridine, 4-dimethylaminopyridine, N-methylmorpholine or triethylamine, expediently at temperatures between 0 and 150° C., preferably at temperatures between 0 and 100° C.

The reaction of a compound of the general formula IV in which $Z_1$ is a nucleofugic leaving group is preferably carried out in a solvent such as methylene chloride, acetonitrile, tetrahydrofuran, dioxane, toluene, dimethylformamide or dimethyl sulphoxide, if appropriate in the presence of a base such as sodium hydride, potassium carbonate, potassium tert-butoxide or N-ethyldiisopropylamine, at temperatures between –20 and 100° C., preferably at temperatures between 0 and 60° C.

The subsequent removal of a protective radical used is expediently carried out hydrolytically either in the presence of an acid such as hydrochloric acid, sulphuric acid, phosphoric acid, acetic acid, trichloroacetic acid, trifluoroacetice acid or their mixtures or in the presence of a base such as lithium hydroxide, sodium hydroxide or potassium hydroxide in a suitable solvent such as water, water/methanol, water/ethanol, water/isopropanol, methanol, ethanol, water/ tetrahydrofuran or water/dioxane, at temperatures between −10 and 120° C., e.g. at temperatures between room temperature and the boiling temperature of the reaction mixture, or hydrogenolytically in the presence of a hydrogenation catalyst such as palladium/carbon in a suitable solvent such as methanol, ethanol, ethanol/water, glacial acetic acid, ethyl acetate, dioxane or dimethylformamide, preferably at temperatures between 0 and 50° C., e.g. at room temperature, and at a hydrogen pressure of 1 to 5 bar.

c) For the preparation of a compound of the general formula I in which A is an —NR$_3$—CO— group and X$_2$ is a nitrogen atom:

reaction of a compound of the general formula

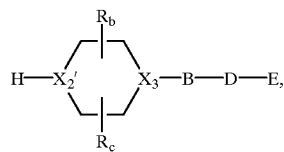
(III)

in which

R$_b$, R$_c$, X$_3$, B, D and E are as defined at the beginning and X$_2$' is a nitrogen atom, with a compound of the general formula

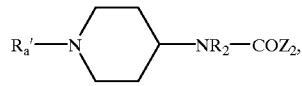
(V)

in which

R$_2$ is as defined at the beginning,

R$_a$', with the exception of the hydrogen atom, has the meanings mentioned for R$_a$ at the beginning or is a protective radical for an imino group and Z$_2$ is a nucleofugic leaving group such as a halogen atom, e.g. a chlorine, bromine or iodine atom, an imidazolyl, triazolyl or 4-nitrophenyloxy group or Z$_2$, together with R$_2$, is a further carbon-nitrogen bond and, if appropriate, subsequent removal of a protective radical used.

The reaction is preferably carried out in a suitable solvent, such as methylene chloride, tetrahydrofuran, toluene, dioxane, dimethyl sulphoxide or dimethylformamide, if appropriate in the presence of an inorganic or of a tertiary organic base or if appropriate in the presence of a dehydrating agent, at temperatures between −30 and 200° C.

The reaction of a compound of the general formula V in which Z$_2$ is a nucleofugic leaving group, or with an isocyanate of the general formula V, is preferably carried out in a solvent such as methylene chloride, acetonitrile, tetrahydrofuran, dioxane, toluene, dimethylformamide or dimethyl sulphoxide, if appropriate in the presence of a base such as sodium hydride, potassium carbonate, potassium tert-butoxide or N-ethyl-diisopropylamine, at temperatures between −20 and 100° C., preferably at temperatures between 0 and 60° C.

The subsequent removal of a protective radical used is expediently carried out hydrolytically either in the presence of an acid such as hydrochloric acid, sulphuric acid, phosphoric acid, acetic acid, trichloroacetic acid, trifluoroacetic acid or their mixtures or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane, at temperatures between −10 and 120° C., e.g. at temperatures between room temperature and the boiling temperature of the reaction mixture, or hydrogenolytically in the presence of a hydrogenation catalyst such as palladium/carbon in a suitable solvent such as methanol, ethanol, ethanol/water, glacial acetic acid, ethyl acetate, dioxane or dimethylformamide, preferably at temperatures between 0 and 50° C., e.g. at room temperature, and at a hydrogen pressure from 1 to 5 bar.

d) For the preparation of a compound of the general formula I in which D is an —O—R$_1$CR$_4$—CO— group:

reaction of a compound of the general formula

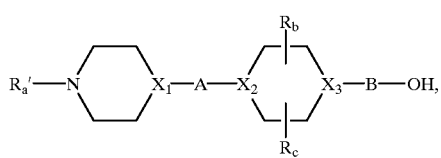
(VI)

in which

R$_b$, R$_c$, A, B and X$_1$ to X$_3$ are as defined at the beginning and

R$_a$', with the exception of the hydrogen atom, has the meanings mentioned for R$_a$ at the beginning or is a protective radical for an imino group, with a compound of the general formula $Z_3$—R$_1$CR$_4$—CO—E, (VII)

in which

R$_1$, R$_4$ and E are as defined at the beginning and Z$_3$ is a leaving group such as a halogen atom, e.g. a chlorine or bromine atom, or alternatively, if B is one of the phenylene groups mentioned at the beginning, a hydroxyl group and, if appropriate, subsequent removal of a protective radical used.

The reaction is expediently carried out in a solvent such as methylene chloride, tetrahydrofuran, dioxane, dimethyl sulphoxide, dimethylformamide or acetone, if appropriate in the presence of a reaction accelerator such as sodium or potassium iodide and preferably in the presence of a base such as sodium carbonate or potassium carbonate or in the presence of a tertiary organic base such as N-ethyldiisopropylamine or N-methylmorpholine, which can simultaneously also serve as a solvent, or if appropriate in the presence of silver carbonate or silver oxide or in the presence of an azodicarboxylic acid diester and of a phosphine at temperatures between −30 and the boiling temperature of the solvent used, but preferably at temperatures between −10 and 80° C.

If Z$_3$ is a hydroxyl group, the reaction is preferably carried out in an aprotic solvent such as diethyl ether, tetrahydrofuran, dioxane, diglyme, benzene or toluene in the presence of an azodicarboxylic acid diester such as diethyl azodicarboxylate and of a phosphine such as triphenylphosphine, at temperatures between −20° C. and the boiling temperature of the solvent used.

The subsequent removal of a protective radical used is expediently carried out hydrolytically either in the presence of an acid such as hydrochloric acid, sulphuric acid, phosphoric acid, acetic acid, trichloroacetic acid, trifluoroacetic acid or their mixtures or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane, at temperatures between −10 and 120° C., e.g. at temperatures between room temperature and the boiling temperature of the reaction mixture, or hydrogenolytically in the presence of a hydrogenation catalyst such as palladium/carbon in an suitable solvent such as methanol, ethanol, ethanol/water, glacial acetic acid, ethyl acetate, dioxane or dimethylformamide, preferably at temperatures between 0 and 50° C., e.g. at room temperature, and at a hydrogen pressure from 1 to 5 bar.

e) For the preparation of a compound of the general formula I in which B is a 3-piperidinylene, 4-piperidinylene or 1,4-piperazinylene group, it additionally being possible to substitute a 1,4-piperazinylene group by $R_b$ and $R_c$, in which $R_b$ and $R_c$ are defined as mentioned above, and D is an ethylene group:

reaction of a compound of the general formula

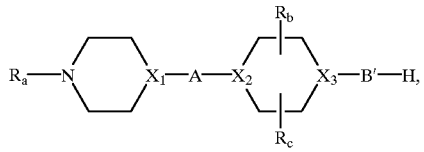  (VIII)

in which $R_a$ to $R_c$, $X_1$ to $X_3$ and A are as defined at the beginning and B' is a 3-piperidinylene, 4-piperidinylene or 1,4-piperazinylene group, with a compound of the general formula

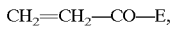  (IX)

in which

E, with the exception of the hydroxyl group, is as defined at the beginning.

The reaction is preferably carried out in a solvent such as methanol, ethanol, methylene chloride, tetrahydrofuran, toluene, dioxane, dimethyl sulphoxide or dimethylformamide, if appropriate in the presence of a tertiary organic base such as N-ethyldiisopropylamine or N-methylmorpholine, at temperatures between −30 and 150° C., but preferably at temperatures between 0 and 100° C.

f) For the preparation of a compound of the general formula I in which the radicals B and $X_3$ are linked with one another via a carbon-nitrogen or nitrogen-carbon bond:

reductive amination of a compound of the general formula

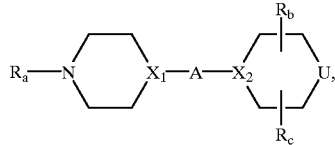  (X)

with a compound of the general formula

  (XI)

in which $R_a$ to $R_c$, $X_1$, $X_2$, A, D and E are as defined at the beginning, U is a carbonyl group and B" is a 3-piperidinylene, 4-piperidinylene or 1,4-piperazinylene group, it additionally being possible to substitute a 1,4-piperazinylene group by $R_b$ and $R_c$, in which $R_b$ and $R_c$ are defined as mentioned above, or U is an imino group and B" is a cyclohexanone group.

The reductive amination is preferably carried out in the presence of a complex metal hydride such as sodium borohydride, lithium borohydride, sodium cyanoborohydride, zinc borohydride, sodium triacetoxyborohydride or borane/pyridine, expediently at a pH of 1–7, if appropriate in the presence of a dehydrating agent such as molecular sieves or titanium (IV) isopropoxide and at room temperature or with hydrogen in the presence of a hydrogenation catalyst, e.g. in the presence of palladium/carbon, at a hydrogen pressure of 1 to 5 bar, preferably at temperatures between 20° C. and the boiling temperature of the solvent used.

g) For the preparation of a compound of the general formula I in which E, with the exception of the hydroxyl group, is as defined at the beginning:

reduction of a compound of the general formula

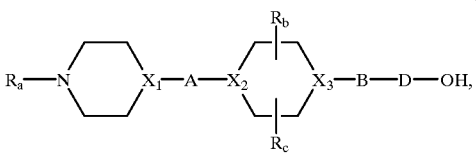  (XII)

in which $R_a$ to $R_c$, $X_1$ to $X_3$, A, B and D are as defined at the beginning, or their reactive derivatives, with an alcohol of the general formula

  (XIII)

or with its formamide acetal or of a compound of the general formula XII with a compound of the general formula

  (XIV)

in which $R_d$ is an alkyl group having 1 to 6 carbon atoms, a phenylalkyl group in which the alkyl moiety can contain 1 to 3 carbon atoms, a cycloalkyl group having 3 to 9 carbon atoms in which the cycloalkyl moiety having 5 to 8 carbon atoms can be additionally substituted by one or two alkyl groups each having 1 to 3 carbon atoms, a cycloalkyl group having 5 to 8 carbon atoms in which in the cycloalkyl moiety a methylene group in the 3- or 4-position is replaced by an oxygen atom or by an imino group which is optionally substituted by an alkyl, phenylalkyl or phenylalkoxycarbonyl group in which the alkyl and alkoxy moiety can each contain 1 to 3 carbon atoms, or by an alkanoyl group having 2 to 6 carbon atoms, and the cycloalkyl moiety can additionally be substituted by one or two alkyl groups each having 1 to 3 carbon atoms, a cycloalkenyl group in which the cycloalkenyl moiety can contain 4 to 7 carbon atoms, an alkenyl, phenylalkenyl, alkynyl or phenylalkynyl group, with the proviso that no bond to the oxygen atom starts from a carbon atom which carries a double or triple bond and in which the alkenyl and alkynyl moieties can each contain 3 to 5 carbon atoms, a cycloalkylalkyl group in which the cycloalkyl moiety can contain 3 to 8 carbon atoms and the alkyl moiety 1 to 3 carbon atoms, a bicycloalkyl group having a total of 8 to 10 carbon atoms, which in the bicycloalkyl moiety can additionally be substituted by one or two alkyl groups each having 1 to 3 carbon atoms, or a 1,3-dihydro-3-oxo-1-isobenzofuranyloxy group, $R_e$ has the meanings mentioned for $R_d$ above and is additionally an $R_7$—CO—O—$(R_5CR_6)$—O— group, in which $R_5$ to $R_7$ are as defined at the beginning, and $Z_4$ is a leaving group such as a halogen atom, e.g. a chlorine or bromine atom.

The reaction with an alcohol of the general formula XII is expediently carried out in a solvent or solvent mixture such as methylene chloride, benzene, toluene, chlorobenzene, tetrahydrofuran, benzene/tetrahydrofuran or dioxane, but preferably in an alcohol of the general formula XII, if appropriate in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole, triphenyl phosphine/carbon tetrachloride or triphenylphosphine/diethyl azodicarboxylate, if appropriate in the presence of a base such as potassium carbonate, N-ethyldiisopropylamine or N,N-dimethylaminopyridine, expediently at temperatures between 0 and 150° C., preferably at temperatures between 0 and 80° C.

With a compound of the general formula XIV, the reaction is expediently carried out in a solvent such as methylene chloride, tetrahydrofuran, dioxane, dimethyl sulphoxide, dimethylformamide or acetone, if appropriate in the presence of a reaction accelerator such as sodium or potassium iodide and preferably in the presence of a base such as sodium carbonate or potassium carbonate or in the presence of a tertiary organic base such as N-ethyldiisopropylamine or N-methylmorpholine, which can simultaneously also serve as a solvent, or if appropriate in the presence of silver carbonate or silver oxide at temperatures between −30 and 100° C., but preferably at temperatures between −10 and 80° C.

h) For the preparation of a compound of the general formula I in which A is an —$HCR_1$—NH— group: reduction of a compound of the general formula

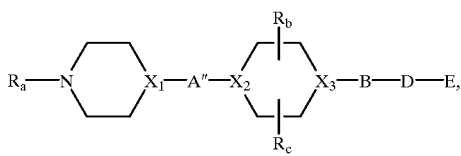

(XV)

in which $R_a$ to $R_c$, $X_1$ to $X_3$, B and D are as defined at the beginning and A" is an —$HCR_1$—N= group, in which $R_1$ is as defined at the beginning.

The reduction is preferably carried out in the presence of a complex metal hydride such as sodium borohydride, lithium borohydride, sodium cyanoborohydride, zinc borohydride, sodium triacetoxyborohydride or borane/pyridine, expediently at a pH of 1–7, if appropriate in the presence of a dehydrating agent such as molecular sieves or titanium(IV) isopropoxide and at room temperature or with hydrogen in the presence of a hydrogenation catalyst, e.g. in the presence of palladium/carbon, at a hydrogen pressure of 1 to 5 bar, preferably at temperatures between 20° C. and the boiling temperature of the solvent used.

If, according to the invention, a compound of the general formula I is obtained which contains an imino group, this can be converted by means of subsequent alkylation or acylation into the desired alkylated or acylated compound of the general formula I.

The subsequent alkylation is optionally carried out in a solvent or solvent mixture such as methylene chloride, dimethylformamide, benzene, toluene, chlorobenzene, tetrahydrofuran, benzene/tetrahydrofuran or dioxane using an alkylating agent such as an appropriate halide or sulphonic acid ester, e.g. using methyl iodide, ethyl bromide, dimethyl sulphate or benzyl chloride, if appropriate in the presence of a tertiary organic base or in the presence of an inorganic base, expediently at temperatures between 0 and 150° C., preferably at temperatures between 0 and 100° C., or using an appropriate carbonyl compound such as formaldehyde, acetaldehyde, propionaldehyde or acetone in the presence of a complex metal hydride such as sodium borohydride, lithium borohydride or sodium cyanoborohydride, expediently at a pH of 6–7 and at room temperature or in the presence of a hydrogenation catalyst, e.g. with hydrogen in the presence of palladium/carbon, at a hydrogen pressure of 1 to 5 bar. The methylation, however, can also be carried out in the presence of formic acid as a reducing agent at elevated temperatures, e.g. at temperatures between 60 and 120° C.

The subsequent acylation is carried out using an appropriate reactive carboxylic acid derivative such as the acid halide, if appropriate in a solvent or solvent mixture such as methylene chloride, dimethylformamide, benzene, toluene, chlorobenzene, tetrahydrofuran or dioxane, if appropriate in the presence of a tertiary organic base or in the presence of an inorganic base or using an appropriate carboxylic acid in the presence of a dehydrating agent, e.g. in the presence of isobutyl chloroformate, thionyl chloride, trimethylchlorosilane, phosphorus trichloride, 2-(1H-benzotriazol-1-yl)-1,1,3,3-tetramethyluronium tetrafluoroborate, N,N'-dicyclohexylcarbodiimide, N,N'-dicyclohexylcarbodiimide/N-hydroxysuccinimide or 1-hydroxybenzotriazole and if appropriate in the presence of 4-dimethylaminopyridine, N,N'-carbonyldiimidazole or triphenylphosphine/carbon tetrachloride, expediently at temperatures between 0 and 150° C., preferably at temperatures between 0 and 80° C.

In the reactions described above, reactive groups which may be present such as hydroxyl, carboxyl, amino, alkylamino or imino groups can be protected during the reaction by customary protective groups which are removed again after the reaction.

For example, a suitable protective radical for a hydroxyl group is the trimethylsilyl, acetyl, benzoyl, tert-butyl, trityl, benzyl or tetrahydropyranyl group, protective radicals for a carboxyl group are the trimethylsilyl, methyl, ethyl, tert-butyl, benzyl or tetrahydropyranyl group and a protective radical for an amino, alkylamino or imino group is the formyl, acetyl, trifluoroacetyl, methoxycarbonyl, ethoxycarbonyl, tert-butoxycarbonyl, benzyloxycarbonyl, benzyl, methoxybenzyl or 2,4-dimethoxybenzyl group, for the imino group additionally the methyl group and for the amino group the phthalyl group.

The possible subsequent removal of a protective radical used is carried out, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali base such as sodium hydroxide or potassium hydroxide or by means of ether cleavage, e.g. in the presence of iodotrimethylsilane, at temperatures between 0 and 120° C., preferably at temperatures between 10 and 100° C.

The removal of a benzyl, methoxybenzyl or benzyloxycarbonyl radical, however, is carried out, for example, hydrogenolytically, e.g. with hydrogen in the presence of a catalyst such as palladium/carbon in a solvent such as methanol, ethanol, isopropanol, ethyl acetate or glacial acetic acid, if appropriate with addition of an acid such as hydrochloric acid, at temperatures between 0 and 100° C., but preferably at temperatures between 20 and 60° C., and at a hydrogen pressure of 1 to 7 bar, but preferably of 3 to 5 bar.

The removal of a tert-butyl or tert-butyloxycarbonyl radical is preferably carried out by treatment with an acid such as trifluoroacetic acid or hydrochloric acid or by treatment with iodotrimethylsilane, if appropriate using a solvent such as methylene chloride, dioxane, methanol or ether.

The removal of a trifluoroacetyl radical is preferably carried out by treatment with an acid such as hydrochloric acid, if appropriate in the presence of a solvent such as acetic acid or methanol at temperatures between 50 and 120° C. or by treatment with sodium hydroxide solution, if appropriate in the presence of a solvent such as tetrahydrofuran or methanol at temperatures between 0 and 50° C.

The removal of a methyl group from a methylimino group is preferably carried out in the presence of 1-chloroalkyl chloroformates such as 1-chloroethyl chloroformate, preferably in the presence of a base such as 1,8-bis (dimethylamino)naphthalene in the presence of a solvent such as methylene chloride, 1,2-dichloroethane, toluene or dioxane at temperatures between 0 and 150° C., preferably at temperatures between 20° C. and the boiling temperature of the reaction mixture, and subsequent treatment with an alcohol such as methanol at temperatures between 20° C. and the boiling temperature of the alcohol used.

The removal of a phthalyl radical is preferably carried out in the presence of hydrazine or of a primary amine such as methylamine, ethylamine or n-butylamine in a solvent such as methanol, ethanol, isopropanol, toluene/water or dioxane at temperatures between 20 and 50° C.

Furthermore, the compounds of the general formula I obtained, as has already been mentioned at the beginning, can be separated into their enantiomers and/or diastereomers. Thus, for example, cis/trans mixtures can be separated into their cis and trans isomers, and chiral compounds into their enantiomers.

Thus, for example, the cis/trans mixtures obtained can be separated by chromatography into their cis and trans isomers, the compounds of the general formula I obtained which occur in racemates can be separated by methods known per se (see Allinger N. L. and Eliel E. L. in "Topics in Stereochemistry", Vol. 6, Wiley Interscience, 1971) into their optical antipodes and compounds of the general formula I having at least 2 stereogenic centres can be separated on the basis of their physico-chemical differences according to methods known per se, e.g. by chromatography and/or fractional crystallization, into their diastereomers which, if they are obtained in racemic form, can then be separated into the enantiomers as mentioned above.

The separation of enantiomers is preferably carried out by column separation on chiral phases or by recrystallization from an optically active solvent or by reaction with an optically active substance forming salts or derivatives such as, for example, esters or amides with the racemic compound, in particular acids and their activated derivatives or alcohols, and separation of the diastereomeric salt mixture or derivative obtained in this way, for example on the basis of different solubilities, it being possible to liberate the free antipodes from the pure diastereomeric salts or derivatives by the action of suitable agents. Particularly useful, optically active acids are, for example, the D and L forms of tartaric acid or dibenzoyltartaric acid, di-o-tolyltartaric acid, malic acid, mandelic acid, camphorsulphonic acid, glutamic acid, aspartic acid or quinic acid. A suitable optically active alcohol is, for example, (+)- or (−)-menthol and a suitable optically active acyl radical in amides is, for example, (+)- or (−)-menthyloxycarbonyl.

In addition, the compounds of the formula I obtained can be converted into their salts, in particular for pharmaceutical use into their physiologically tolerated salts with inorganic or organic acids. Suitable acids for this purpose are, for example, hydrochloric acid, hydrobromic acid, sulphuric acid, phosphoric acid, fumaric acid, succinic acid, lactic acid, citric acid, tartaric acid or maleic acid.

Additionally, the novel compounds of the formula I thus obtained, if these contain a carboxyl group, can if desired then be converted into their salts with inorganic or organic bases, in particular for pharmaceutical use into their physiologically tolerated salts. Suitable bases here are, for example, sodium hydroxide, potassium hydroxide, arginine, cyclohexylamine, ethanolamine, diethanolamine and triethanolamine.

The compounds used as starting substances are known from the literature in some cases or they are obtained according to processes known from the literature (see Examples I to XXIII).

As already mentioned at the beginning, the novel carboxylic acid derivatives of the general formula I and their salts, in particular their physiologically tolerated salts with inorganic or organic acids or bases, have useful properties, in particular useful pharmacological properties, in addition to an antiinflammatory and antiosteoclastic action, in particular antithrombotic, antiaggregatory and antitumour or antimetastatic action.

For example, the compounds of the general formula I were investigated for their biological actions as follows:
1. Inhibition of the binding of $^3$H-BIBU 52 to Human Platelets A suspension of human platelets in plasma is incubated with $^3$H-BIBU 52 [=(3S,5S)-5-[(4'-amidino-4-biphenylyl) oxymethyl]-3-[(carboxy)methyl]-2-pyrrolidinone[3-$^3$H-4-biphenylyl]], which replaces the ligand $^{125}$I-fibrinogen known from the literature, (see DE-A-4,214,245) and various concentrations of the substance to be tested. The free and bound ligand is separated by centrifugation and determined quantitatively by scintillation counting. From the measurements, the inhibition of $^3$H-BIBU 52 binding by the test substance is determined.

To do this, donor blood is taken from an antecubital vein and anticoagulated with trisodium citrate (final concentration 13 mM). The blood is centrifuged at 170×g for 10 minutes and the supernatant platelet-rich plasma (PRP) is removed. The residual blood is rapidly centrifuged once more to obtain plasma. The PRP is diluted 1:10 with autologous plasma. 750 µl are incubated with 50 ml of physiological saline solution, 100 µl of test substance solution, 50 µl of $^{14}$C-sucrose (3700 Bq) and 50 µl of $^3$H-BIBU 52 (final concentration: 5 nM) at room temperature for 20 minutes. To measure the non-specific binding, instead of the test substance, 100 µl of BIBU 52 (final concentration: 30 µM) is employed. The samples are centrifuged at 10,000×g for 20 seconds and the supernatant is removed. 100 µl thereof are measured to determine the free ligand. The pellet is dissolved in 500 µl of 0.2N NaOH, and 450 µl are mixed with 2 ml of scintillator and 25 µl of 5N HCl and measured. The residual plasma still remaining in the pellet is determined from the $^{14}$C content, the bound ligand from the $^3$H measurement. After subtraction of the non-specific binding, the pellet activity is plotted against the concentration of the test substance and the concentration for a 50% inhibition of binding is determined.

2. Antithrombotic Action

Methodology

Platelet aggregation is measured according to the method of Born and Cross (J. Physiol. 170, 397 (1964)) in platelet-rich plasma of healthy subjects. To inhibit clotting, the blood is treated with sodium citrate 3.14% in the volume ratio 1:10.

Collagen-induced Aggregation

The course of the decrease in the optical density of the platelet suspension is measured photometrically and recorded after addition of the aggregation-inducing substance. From the angle of inclination of the density curve, the aggregation rate is deduced. The point on the curve at which the greatest light transmission is present serves for the calculation of the optical density.

The amount of collagen is chosen to be as low as possible, but of course such that an irreversibly running reaction curve results. Commercially available collagen from Hormonchemie, Munich is used.

Before the addition of collagen, the plasma is incubated at 37° C. with the substance for 10 minutes in each case.

From the measured values obtained, an $EC_{50}$ which relates to a 50% change in the optical density in the sense of an inhibition of aggregation is determined graphically.

The following table contains the results found:

| Substance (Example No.) | Fibrinogen binding test $IC_{50}$[nM] | Inhibition of platelet aggregation $EC_{50}$[nM] |
| --- | --- | --- |
| 1 | 150 | 120 |
| 1(1) | 360 | 370 |
| 1(3) | 47 | 110 |
| 1(7) | 260 | 240 |
| 1(22) | 260 | 370 |
| 7(1) | 200 | 250 |
| 7(6) | 150 | |

Additionally, the compounds of Examples 2, 9, 9(1), 9(2) and 2(4) in Rhesus monkeys after oral administration of 1 mg/kg exhibit high plasma levels over a period of more than 8 hours.

The novel compounds are well tolerated, since, for example, after intravenous administration of 100 mg/kg of the compound according to the invention of the above examples to the mouse it was not possible to observe any toxic side effects.

On account of their inhibitory action on cell-cell or cell-matrix interactions, the novel carboxylic acid derivatives of the general formula I and their physiologically tolerated salts are suitable for the control or prevention of illnesses in which relatively small or relatively large cell aggregates occur or cell-matrix interactions play a part, e.g. in the control or prevention of venous and arterial thromboses, of cerebrovascular disorders, of pulmonary embolisms, of cardiac infarct, of arteriosclerosis, of osteoporosis and of metastasization of tumours and of the therapy of genetically related or alternatively acquired disorders of the interactions of cells with one another or with solid structures. Furthermore, they are suitable for concomitant therapy in thrombolysis with fibrinolytics or vascular interventions such as transluminal angioplasty or alternatively in the therapy of states of shock, of psoriasis, of diabetes and of inflammations.

For the control or prevention of the abovementioned illnesses, the dose is between 0.1 mg and 30 mg/kg of body weight, preferably 1 mg to 15 mg/kg of body weight, with up to 4 administrations per day. To this end, the compounds of the formula I prepared according to the invention, if appropriate in combination with other active substances such as thromboxane receptor antagonists and thromboxane synthesis inhibitors or their combinations, serotonin antagonists, α-receptor antagonists, alkyl nitrates such as glyceryl trinitrate, phosphodiesterase inhibitors, prostacyclin and its analogues, fibrinolytics such as tPA, prourokinase, urokinase, streptokinase, or anticoagulants such as heparin, dermatan sulphate, activated protein C, vitamin K antagonists, hirudin, inhibitors of thrombin or other activated clotting factors, together with one or more inert customary excipients and/or diluents, e.g. with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances such as hard fat or suitable mixtures thereof, in customary pharmaceutical preparations such as tablets, coated tablets, capsules, powders, suspensions, solutions, sprays or suppositories.

The following examples are intended to illustrate the invention in greater detail:

Preparation of the Starting Materials

EXAMPLE I 1-(4-Methoxycarbonylmethyloxyphenyl)piperazine trifluoroacetate a) 1-(tert-Butyloxycarbonyl)-4-(4-hydroxyphenyl) piperazine A solution of 52.4 g (0.24 mol) of di-tert-butyl dicarbonate in 50 ml of dioxane is added dropwise at 0° C. with stirring to a solution of 35.6 g (0.2 mol) of 4-hydroxyphenylpiperazine in 300 ml of dioxane and 300 ml of water. After addition is complete, the reaction mixture is allowed to warm to room temperature and is stirred further overnight at this temperature. The solution is then concentrated to a small volume in vacuo and acidified to pH 3 using potassium hydrogen sulphate. The mixture is extracted with ethyl acetate, and the combined extracts are dried over sodium sulphate and concentrated to dryness in vacuo. The residue is crystallized from ether and dried.

Yield: 38 g (68% of theory), $R_f$: 0.40 (silica gel; methylene chloride/methanol=9:1)

b) 1-(tert-Butyloxycarbonyl)-4-(4-methoxycarbonylmethyloxyphenyl)piperazine 20.5 g (0.15 mol) of potassium carbonate are added with stirring at room temperature to a solution of 38 g (0.137 mol)

of 1-(tert-butyloxycarbonyl)-4-(4-hydroxyphenyl) piperazine in 150 ml of dry dimethylformamide and the mixture is stirred for a further 45 minutes. 23.0 g=14.2 ml (0.15 mol) of methyl bromoacetate are then added with further stirring and the mixture is stirred further overnight. The solution is then concentrated to dryness in vacuo and the residue is partitioned between water and ethyl acetate. The combined organic phases are dried over sodium sulphate and concentrated. The residue which remains is triturated with ether, filtered off with suction and dried.

Yield: 35.7 g (75% of theory),
Melting point: 102–104° C.
$R_f$: 0.65 (silica gel; methylene chloride/methanol=9.5:0.5)

c) 1-(4-Methoxycarbonylmethyloxyphenyl)piperazine trifluoroacetate

A solution of 35.7 g (0.1 mol) of 1-(tert-butyloxycarbonyl)-4-(4-methoxycarbonylmethyloxyphenyl)piperazine in 190 ml of trifluoroacetic acid and 190 ml of methylene chloride is allowed to stand for 3 hours at room temperature. After this time, the solution is concentrated to dryness in vacuo. The residue is crystallized from ether, filtered off with suction and dried.

Yield: 38 g (quantitative),
Melting point: 106–108° C.
$R_f$: 0.40 (silica gel; methylene chloride/methanol=9:1)

EXAMPLE II 1-(1-tert-Butyloxycarbonyl-piperidin-4-yl)-2-methanesulphonyloxyethane a) 2-(1-tert-Butyloxycarbonyl-piperidin-4-yl)ethanol A solution of 100 g (0.812 mol) of 4-(2-hydroxyethyl) pyridine in 1 l of 50% strength acetic acid is exhaustively hydrogenated over 10 g of platinum dioxide at room temperature and a hydrogen pressure of 50 psi. The catalyst is filtered off with suction and the solution is concentrated to dryness in vacuo. The oily residue of 4-(2-hydroxyethyl) piperidine acetate which remains is dissolved in 500 ml of dioxane and 500 ml of water, adjusted to pH 10 with 10N sodium hydroxide solution and treated with a solution of 177.2 g (0.812 mol) of di-tert-butyl dicarbonate in 200 ml of dioxane. The mixture is stirred overnight at room temperature, diluted with water and extracted with ethyl acetate. The combined organic phases are dried and concentrated to dryness in vacuo. The residue is purified by means of chromatography on a silica gel column, ethyl acetate/cyclohexane=1:2 and 1:1 being used as eluent.

Yield: 44.3 g (24% of theory),
$R_f$: 0.40 (silica gel; methylene chloride/methanol/conc. ammonia=9:1:0.1)

b) 1-(1-tert-Butyloxycarbonyl-piperidin-4-yl)-2-methanesulphonyloxyethane 28 ml (0.193 mol) of triethylamine are added to a solution of 44.3 g (0.193 mol) of 2-(1-tert-butyloxycarbonylpiperidin-4-yl)ethanol in 200 ml of methylene chloride. 15 ml (0.193 ml) of methanesulphonyl chloride are then added dropwise with ice-cooling and stirring and the mixture is allowed to stand overnight at room temperature after addition is complete. It is then treated with water, the organic phase is separated off and the aqueous phase is extracted once more with methylene chloride. The combined organic phases are dried and concentrated to dryness in vacuo. The residue which remains is crystallized from petroleum ether.

Yield: 51 g (86% of theory),
Melting point: 76–78° C.
$R_f$: 0.30 (silica gel; ethyl acetate/cyclohexane=1:1)

EXAMPLE III 1-(4-Ethoxycarbonylmethyloxyphenyl)piperazin-2-one hydrochloride a) Ethyl 4-nitrophenoxyacetate 125.4 g (0.9 mol) of 4-nitrophenol are dissolved in 1000 ml of absolute dimethylformamide and, after addition of 150.6 g (0.9 mol) of dried potassium carbonate, the solution is stirred at room temperature for 45 minutes. 150.6 g=100 ml (0.9 mol) of ethyl bromoacetate are then added dropwise with stirring and the suspension is then heated at an oil bath temperature of 80° C. for 5 hours. The heating is switched off and the suspension is stirred for a further 15 hours, the reaction mixture slowly coming to room temperature. The undissolved inorganic salts are filtered off with suction and the filtrate is concentrated to dryness in vacuo. The residue is partitioned between ethyl acetate and water. The organic phase is extracted with water a further 2 times and then dried over sodium sulphate, filtered and concentrated. The residue is triturated with petroleum ether and filtered off with suction. 192.0 g (95% of theory) of the desired product are obtained, which is processed further without further purification.

$R_f$: 0.80 (silica gel; methylene chloride)

b) Ethyl 4-aminophenoxyacetate 144.9 g (0.643 mol) of methyl 4-nitrophenoxyacetate are exhaustively hydrogenated over 1.5 g of palladium on carbon (10% strength) at room temperature and under a hydrogen pressure of 50 psi in 1500 ml of ethyl acetate. The catalyst is filtered off with suction and the filtrate is concentrated to dryness in vacuo. The residue is triturated with petroleum ether and filtered off with suction.

Yield: 123.4 g (98% of theory),
$R_f$: 0.26 (silica gel; methylene chloride)

c) Ethyl 4-(2,2-diethoxyethylamino)phenoxyacetate

A solution of 20 g (0.102 mol) of ethyl 4-aminophenoxyacetate, 18.5 ml (0.123 mol) of bromoacetaldehyde diethyl acetal and 21.4 ml (0.123 mol) of N-ethyldiisopropylamine in 60 ml of dry dimethylformamide is heated at 100° C. for 30 hours and then concentrated to dryness in vacuo. The residue is partitioned between ethyl acetate and water, and the organic phase is washed with water, dried and concentrated to dryness in vacuo. The residue is purified by means of chromatography on a silica gel column, cyclohexane/ethyl acetate=4:1 being used as eluent.

Yield: 18.05 g (57% of theory),
Mass spectrum: $M^+$=311
$R_f$: 0.78 (silica gel; methylene chloride/methanol=9:1)

d) Ethyl 4-[N-(benzyloxycarbonylglycyl)-N-(2,2-diethoxyethyl)amino]phenoxyacetate A mixture of 6 g (0.0193 mol) of ethyl 4-(2,2-diethoxyethylamino)phenoxyacetate, 4.03 g (0.0193 mol) of N-benzyloxycarbonylglycine, 3.2 ml (0.029 mol) of N-methylmorpholine and 7.1 g (0.0193 mol) of 2-(1H-benzotriazol-1-yl)-1,1,3,3-tetramethyluronium tetrafluoroborate in 150 ml of dry tetrahydrofuran is stirred overnight at room temperature and then heated at reflux temperature for 8 hours. The mixture is then concentrated to dryness in vacuo. The residue is partitioned between saturated aqueous sodium hydrogen carbonate solution and ethyl acetate and the aqueous phase is extracted twice more with ethyl acetate. The combined organic phases are dried and concentrated to dryness in vacuo. The residue is purified by means of chromatography on a silica gel column, cyclohexane/ethyl acetate=1:1 being used as eluent.

Yield: 9.69 g (quantitative) of oil,
Mass spectrum: $M^+$=502

$R_f$: 0.42 (silica gel; cyclohexane/ethyl acetate=1:1)

e) 4-Benzyloxycarbonyl-1-(4-ethoxycarbonylmethyl-oxyphenyl)piperazin-5-en-2-one 2 g of p-toluenesulphonic acid are added to a solution of 9.6 g (0.019 mol) of ethyl 4-[N-(benzyloxycarbonylglycyl)-N-(2,2-diethoxyethyl)amino]phenoxyacetate in 200 ml of toluene and the mixture is heated at 75° C. for 4 hours. It is concentrated to dryness in vacuo and the residue is partitioned between saturated aqueous sodium hydrogen carbonate solution and ethyl acetate. The aqueous phase is extracted twice more with ethyl acetate. The combined ethyl acetate extracts are dried and concentrated to dryness in vacuo. The crude residue (7 g) is purified by means of chromatography on a silica gel column, ethyl acetate/cyclohexane=1:1 being used as eluent. After evaporation, the residue is crystallized from ether/petroleum ether.

Yield: 1.64 g (21% of theory),
Melting point: 85–88° C.
$R_f$: 0.60 (silica gel; ethyl acetate/cyclohexane=1:1)

f) 1-(4-Ethoxycarbonylmethyloxyphenyl)piperazin-2-one hydrochloride 1.6 g (0.0039 mol) of 4-benzyloxycarbonyl-1-(4-ethoxycarbonylmethyloxyphenyl)piperazine-5-en-2-one are exhaustively hydrogenated at room temperature and under a hydrogen pressure of 50 psi over 1 g of palladium on carbon (10% strength) in 100 ml of ethyl acetate after addition of an equimolar amount of hydrochloric acid. After removal of the catalyst and concentration of the filtrate in vacuo, the residue is triturated with ether, filtered off with suction and dried.

Yield: 0.97 g (77% of theory),
Melting point: 163–168° C.
$R_f$: 0.45 (silica gel; methylene chloride/methanol/conc. ammonia=9:1:0.1)

EXAMPLE IV

1-[4-(2-Methoxycarbonylethyl)phenyl]piperazine a) Methyl 4-nitrocinnamate

A suspension of 50 g (0.258 mol) of 4-nitrocinnamic acid and 5 ml of conc. sulphuric acid in 1200 ml of methanol is heated at reflux temperature for 10 hours. After cooling, the solid is filtered off with suction and dried.

Yield: 51.1 g (96% of theory),
Melting point: 135–138° C.
$R_f$: 0.9 (silica gel; methylene chloride/methanol=9:1)

b) Methyl 3-(4-aminophenyl)propionate 50 g (0.241 mol) of methyl 4-nitrocinnamate are exhaustively hydrogenated at room temperature and 50 psi hydrogen pressure over 5 g of palladium on carbon (10% strength) at catalyst in 1000 ml of ethyl acetate. The catalyst is filtered off and the filtrate is concentrated to dryness in vacuo. The residue is crystallized from ether/petroleum ether.

Yield: 40.5 g (94% of theory),
Melting point: 52–54° C.
$R_f$: 0.75 (silica gel; methylene chloride/methanol=9.5:0.5)

c) 4-Benzyl-1-[4-(2-methoxycarbonylethyl)phenyl]piperazine

A mixture of 3 g (0.0167 mol) of methyl 3-(4-aminophenyl)propionate, 4.5 g (0.0167 mol) of bis(2-chloroethyl)benzylamine and 7.57 g (10 ml)(0.059 mol) of N-ethyldiisopropylamine in 60 ml of absolute ethanol is heated at reflux temperature for 20 hours. The mixture is then concentrated to dryness in vacuo and the residue is purified by chromatography on a silica gel column, methylene chloride/methanol=50:1 being used as eluent.

Yield: 2.9 g (51% of theory),
Melting point: 56–58° C.
$R_f$: 0.80 (silica gel; methylene chloride/methanol=9:1)

d) 1-[4-(2-Methoxycarbonylethyl)phenyl]piperazine 2.9 g (0.0083 mol) of 4-benzyl-1-[4-(2-methoxycarbonylethyl)phenyl]piperazine are exhaustively hydrogenated at room temperature and under a hydrogen pressure of 45 psi over 1 g of palladium on carbon (10% strength) in 100 ml of methanol. The catalyst is filtered off with suction and the filtrate is concentrated to dryness in vacuo.

Yield: 2.2 g (78% of theory) of resin,
$R_f$: 0.13 (silica gel; methylene chloride/methanol=9:1)

EXAMPLE V 1-(3,4-Dimethoxycarbonylmethyloxyphenyl)piperazine a) 3,4-Dimethoxycarbonylmethyloxynitrobenzene A mixture of 10 g (0.0645 mol) of 4-nitropyrocatechol, 12.8 ml (0.1354 mol) of methyl bromoacetate and 18.7 g (0.1354 mol) of potassium carbonate in 100 ml of dry dimethylformamide is heated at 80° C. with stirring for 5 hours. It is then concentrated to dryness in vacuo and the residue is partitioned between water and ethyl acetate. The aqueous phase is extracted twice more with ethyl acetate. The combined organic extracts are dried and concentrated in vacuo. The residue is triturated with ether and filtered off with suction.

Yield: 11.4 g (59% of theory),
$R_f$: 0.85 (silica gel; methylene chloride)

b) 3,4-Dimethoxycarbonylmethyloxyaniline hydrochloride 11.4 g (0.0381 mol) of 3,4-dimethoxycarbonylmethyloxynitrobenzene are exhaustively hydrogenated at room temperature and under a hydrogen pressure of 50 psi in 160 ml of methanol over 2 g of palladium on carbon (10% strength) in the presence of 40 ml of 1N hydrochloric acid. The catalyst is filtered off, the filtrate is concentrated to dryness in vacuo and the residue is triturated with acetone and filtered off with suction.

Yield: 10.96 g (94% of theory),
$R_f$: 0.65 (silica gel; methylene chloride/methanol=9:1)

c) 4-Benzyl-1-(3,4-dimethoxycarbonylmethyloxyphenyl)piperazine

A suspension of 4 g (0.013 mol) of 3,4-dimethoxycarbonylmethyloxyaniline hydrochloride, 3.5 g (0.013 mol) of bis(2-chloroethyl)benzylamine and 5.09 g (6.74 ml)(0.039 mol) of N-ethyldiisopropylamine in 50 ml of absolute ethanol is heated to reflux with stirring for 20 hours, a clear solution resulting. After concentration to dryness in vacuo, the residue which remains is purified by chromatography on a silica gel column, methylene chloride/methanol=50:1 being used as eluent.

Yield: 1.3 g (23% of theory) of oil,
$R_f$: 0.15 (silica gel; methylene chloride/methanol/conc. ammonia=9:1:0.1)

d) 1-(3,4-Dimethoxycarbonylmethyloxyphenyl)piperazine 1.25 g (0.0029 mol) of 4-benzyl-1-(3,4-dimethoxycarbonylmethyloxyphenyl)piperazine are exhaustively hydrogenated under a hydrogen pressure of 50 psi over 1 g of palladium on carbon as catalyst in 100 ml of methanol at 50° C. The catalyst is filtered off with suction and the filtrate is concentrated to dryness in vacuo. The residue is reacted further without purification.

Yield: 0.7 g (71% of theory) of resin,
$R_f$: 0.11 (silica gel; methylene chloride/methanol=9:1)

EXAMPLE VI 1-tert-Butyloxycarbonylpiperidin-4-ylacetic acid a) Piperidin-4-ylacetic acid 75 g of 4-pyridylacetic acid hydrochloride are treated with 750 ml of glacial acetic acid (50% strength), 6 g of platinum dioxide are added and the mixture is hydrogenated at 3 bar and room temperature in the course of 3 hours. The catalyst is filtered off with suction and the mother liquor is concentrated to dryness in vacuo. The residue is triturated with acetone and filtered off with suction. It is washed twice with acetone and once with ether.

Yield: 71.7 g (92% of theory) of white substance,
Melting point: 150–153° C.

b) 1-tert-Butyloxycarbonylpiperidin-4-ylacetic acid

A solution of 24.3 g (0.11 mol) of di-tert-butyldicarbonate in 20 ml of tetrahydrofuran is added dropwise to a solution of 20 g (0.11 mol) of piperidin-4-ylacetic acid in 250 ml of 1N sodium hydroxide solution and the mixture is allowed to stand at room temperature overnight. It is then neutralized with 250 ml of 1N hydrochloric acid and extracted three times with methylene chloride. The combined organic phases are dried and evaporated to dryness in vacuo. The oily residue is crystallized from petroleum ether.

Yield: 19 g (70% of theory),
Melting point: 97–99° C.

EXAMPLE VII

1-Benzyl-4-carboxymethylpiperazine a) 1-Benzyl-4-methoxycarbonylmethylpiperazine 4.9 g=6.7 ml (0.048 mol) of triethylamine and 7.4 g=4.6 ml (0.048 mol) of methyl bromoacetate are added to a solution of 8.5 g (0.048 mol) of 1-benzylpiperazine in 100 ml of methanol and the mixture is stirred overnight at room temperature. It is then concentrated to dryness in vacuo. The residue is partitioned between saturated aqueous sodium hydrogen carbonate solution and ethyl acetate and the aqueous phase is extracted again with ethyl acetate. The combined organic extracts are dried and concentrated to dryness in vacuo.

Yield: 10.4 g (87% of theory) of oil,
$R_f$: 0.50 (silica gel; methylene chloride/methanol=9:1)

b) 1-Benzyl-4-carboxymethylpiperazine 83.8 ml of 1N sodium hydroxide solution are added to a solution of 10.4 g (41.9 mmol) of 1-benzyl-4-methoxycarbonylmethylpiperazine in 120 ml of tetrahydrofuran and 60 ml of water and the mixture is stirred for 4 hours at room temperature. 83.8 ml of 1N hydrochloric acid are then added and the mixture is concentrated to dryness in vacuo. The residue is treated three times with absolute ethanol, which is distilled off in vacuo each time. The residue which remains is stirred with methylene chloride/methanol=1:1, then the precipitated, organic solid is filtered off and the filtrate is concentrated to dryness in vacuo.

Yield: 7.3 g (74% of theory),
Melting point: 190–192° C.
$R_f$: 0.16 (silica gel; methylene chloride/methanol=4:1)

EXAMPLE VIII

4-Carboxymethyl-1-(4-methoxycarbonylmethyloxyphenyl)piperazine a) 4-Benzyloxycarbonylmethyl-1-(4-methoxycarbonylmethyloxyphenyl)piperazine 4.6 g=3.2 ml (0.02 mol) of benzyl bromoacetate are added to a solution of 9.6 g (0.02 mol) of 1-(4-methoxycarbonylmethyloxyphenyl)piperazine trifluoroacetate and 6.1 g=8.4 ml (0.06 mol) of triethylamine in 150 ml of methanol, and the mixture is heated at reflux temperature for 8 hours and allowed to stand at room temperature overnight. The solution is concentrated to dryness in vacuo and the residue is partitioned between saturated sodium hydrogen carbonate solution and ethyl acetate. The aqueous phase is extracted once more with ethyl acetate. The combined ethyl acetate extracts are dried and concentrated to dryness in vacuo. The residue which remains is purified by means of chromatography on a silica gel column, methylene chloride which contains 2% methanol being used as eluent.

Yield: 3.2 g (40% of theory),
Melting point: 93–94° C.
$R_f$: 0.80 (silica gel; methylene chloride/methanol=9:1)

b) 4-Carboxymethyl-1-(4-methoxycarbonylmethyl-oxyphenyl)piperazine

Prepared from 4-benzyloxycarbonylmethyl-1-(4-methoxycarbonylmethyloxyphenyl)piperazine by hydrogenation over palladium on carbon (10% strength) analogously to Example 5, but without hydrochloric acid.

Yield: 2.2 g (92% of theory),
$R_f$: 0.09 (silica gel; methylene chloride/methanol=9:1)

EXAMPLE IX 1-(4-Methoxycarbonylmethyloxyphenyl)-2-methylpiperazine trifluoracetate a) 4-tert-Butyloxycarbonyl-1-(4-hydroxyphenyl)-2-methylpiperazine A solution of 10 g (0.0485 mol) of 1-(4-methoxyphenyl)-2-methylpiperazine in 50 ml of concentrated hydrochloric acid is heated at 180° C. for 10 hours in an autoclave and then concentrated to dryness in vacuo. The residue which remains is dissolved in 100 ml of dioxane/water=1:1. A pH of 11 is set using 10N sodium hydroxide solution, a solution of 11 g of di-tert-butyl dicarbonate in 15 ml of dioxane is added dropwise with ice-cooling and the mixture is stirred overnight at room temperature. It is then concentrated to dryness in vacuo. The residue is crystallized from methanol/ether. The crystals are filtered off with suction and washed with ether.

Yield: 8.09 g (57% of theory),
$R_f$: 0.45 (silica gel; methylene chloride/methanol=9:1)

b) 4-tert-Butyloxycarbonyl-1-(4-methoxycarbonylmethyl-oxyphenyl)-2-methylpiperazine A suspension of 6 g (0.0205 mol) of 4-tert-butyloxycarbonyl-1-(4-hydroxyphenyl)-2-methylpiperazine, 2.4 ml (0.0246 mol) of methyl bromoacetate and 3.4 g (0.0246 mol) of potassium carbonate in 50 ml of dimethylformamide is heated at 100° C. for 6 hours and, after cooling, concentrated to dryness in vacuo. The residue is partitioned between ethyl acetate and water and the aqueous phase is extracted once more with ethyl acetate. The combined ethyl acetate extracts are concentrated to dryness in vacuo. The residue is purified by means of chromatography on a silica gel column, ethyl acetate/cyclohexane being used as eluent. After evaporation, the residue is crystallized from ether/petroleum ether.

Yield: 6 g (80% of theory),
Melting point: 62–65° C.

c) 1-(4-Methoxycarbonylmethyloxyphenyl)-2-methylpiperazine trifluoroacetate 6 g (0.0165 mol) of 4-tert-butyloxycarbonyl-1-(4-methoxycarbonylmethyloxyphenyl)-2-methylpiperazine are dissolved in 20 ml of methylene chloride and 20 ml of trifluoroacetic acid. This solution is allowed to stand at room temperature for 4 hours and is then concentrated to dryness in vacuo. The residue is treated three times with acetone and concentrated to dryness in vacuo each time. The residue which remains is triturated with ether and filtered off with suction.

Yield: 8.95 g (quantitative),
Melting point: 140–143° C.
$R_f$: 0.22 (silica gel; methylene chloride/methanol/conc. ammonia=9:1:0.1)

EXAMPLE X 2-(1-tert-Butyloxycarbonylpiperazin-4-yl)ethyl bromide

A solution of 1.0 g of 1-tert-butyloxycarbonylpiperazine and 0.7 g (0.005 mol) of N-ethyldiisopropylamine in 5 ml of 1,2-dibromomethane is allowed to stand at room temperature for 3 days and then concentrated to dryness in vacuo. The residue is purified by means of chromatography on a silica gel column, methylene chloride which initially contains 1% and then 2% of methanol being used as eluent.

Yield: 0.6 g (38% of theory),
Mass spectrum: $(M+H)^+$=293/295
$R_f$: 0.40 (silica gel; methylene chloride/methanol=9:1)

EXAMPLE XI 1-(4-Methoxycarbonylmethylphenyl)piperazine hydrochloride a) Methyl 4-aminophenylacetate hydrochloride 7.6 g=4.7 ml of thionyl chloride are added dropwise with stirring at −10° C. to −20° C. to 100 ml of methanol and the mixture is then stirred for half an hour at −20° C. 8.0 g (0.053 mol) of 4-aminophenylacetic acid are added to this solution at −20° C., and it is stirred for a further 2 hours at −20° C. and then overnight at room temperature. The solution is concentrated to dryness in vacuo and the residue is triturated with petroleum ether and filtered off with suction.

Yield: 9.0 g (84% of theory),
Melting point: 194–196° C.
$R_f$: 0.85 (silica gel; methylene chloride/methanol=9:1)

b) 4-Benzyl-1-(4-methoxycarbonylmethylphenyl)piperazine

Prepared from methyl 4-aminophenylacetate hydrochloride, bis(2-chloroethyl)benzylamine and N-ethyldiisopropylamine analogously to Example IVc.

Yield: 1.8 g (55% of theory),
Melting point: 73–75° C. Mass spectrum: $M^+$=324
$R_f$: 0.7 (silica gel; methylene chloride/methanol=9.5:0.5)

c) 1-(4-Methyloxycarbonylmethylphenyl)piperazine hydrochloride

Prepared by hydrogenation of 4-benzyl-1-(4-methoxycarbonylmethylphenyl)piperazine over palladium on carbon (10% strength) analogously to Example IVd.

Yield: 1.5 g (quantitative) of oil,
$R_f$: 0.10 (silica gel; methylene chloride/methanol=9.5:0.5)

EXAMPLE XII (S)-1-(4-Ethoxycarbonylmethyloxyphenyl)-3-(4-methoxybenzyl)piperazin-2-one a) Ethyl 4-(2,2-diethoxyethylamino)phenoxyacetate A solution of 10 g (0.051 mol) of ethyl 4-aminophenoxyacetate, 8.5 ml (0.056 mol) of bromoacetaldehyde diethyl acetal and 9.8 ml (0.056 mol) of N-ethyldiisopropylamine in 30 ml of dry dimethylformamide is heated at 100° C. for 30 hours. After cooling, the mixture is concentrated to dryness in vacuo and the oil which remains is partitioned between ethyl acetate and water. The organic phase is washed with water, dried and concentrated to dryness in vacuo. The residue is purified by means of chromatography on a silica gel column, cyclohexane/ethyl acetate=1:1 being used as eluent. After evaporation, 9.9 g (62% of theory) of an almost colourless oil remain.

$R_f$: 0.70 (silica gel; methylene chloride/methanol=1:1)

b) Ethyl 4-[N-(benzyloxycarbonyl-O-methyl-L-tyrosyl)-2,2-diethoxyethylamino]phenoxyacetate A solution of 2.1 g (67 mmol) of ethyl 4-(2,2-diethoxyethylamino)phenoxyacetate, 2 g (61 mmol) of benzyloxycarbonyl-O-methyl-L-tyrosine, 0.73 ml (67 mmol) of N-methylmorpholine and 0.9 ml (67 mmol) of isobutyl chloroformate in 50 ml of dry dimethylformamide is allowed to stand overnight at room temperature and then concentrated to dryness in vacuo. The residue is partitioned between 0.5 molar potassium hydrogen sulphate solution and ethyl acetate. The organic phase is dried and concentrated to dryness in vacuo. The residue which remains is purified by means of chromatography on a silica gel column, ethyl acetate/cyclohexane=1:2 being used as eluent. After evaporation, 3.3 g (87% of theory) of an almost colourless oil remain.

$R_f$: 0.60 (silica gel; methylene chloride/methanol=1:1)

c) (S)-4-Benzyloxycarbonyl-1-(4-ethoxycarbonylmethyloxyphenyl)-3-(4-methoxybenzyl)piperazin-5-en-2-one A solution of 3.3 g (53 mmol) of ethyl 4-[N-(benzyloxycarbonyl-O-methyl-L-tyrosyl)-2,2-diethoxyethylaminol]phenoxyacetate in 15 ml of trifluoroacetic acid is allowed to stand overnight at room temperature and then concentrated to dryness in vacuo. The residue is partitioned between saturated, aqueous sodium hydrogen carbonate solution and ethyl acetate. The ethyl acetate phase is dried and concentrated to dryness in vacuo. The residue which remains is purified by means of chromatography on a silica gel column, ethyl acetate/cylohexane=1:2 being used as eluent. After evaporation, 3.6 g (76% of theory) remain as almost colourless oil.

$R_f$: 0.50 (silica gel; cyclohexane/ethyl acetate=1:1)

d) (S)-1-(4-Ethoxycarbonylmethyloxyphenyl)-3-(4-methoxybenzylpiperazine-2-one

Prepared by hydrogenation of 1.7 g (82 mmol) of (S)-4-benzyloxycarbonyl-1-(4-ethoxycarbonylmethyloxyphenyl)-3-(4-methoxybenzyl)piperazine-5-en-2-one over palladium on carbon (10% strength) analogously to Example IVd.

Yield: 1.2 g (98% of theory) of oil,
Melting point: 93–94° C.
$R_f$: 0.05 (silica gel; methylene chloride/methanol=9:1)

EXAMPLE XIII 1-(4-tert-Butyloxycarbonylmethyloxyphenyl)-4-[(1-tert-butyloxycarbonylpiperidin-4-yl)methyleneamino]cyclohexane a) 4-(4-tert-Butyloxycarbonylmethyloxyphenyl)cyclohexanone 13 ml (78.9 mmol) of tert-butyl bromoacetate are added dropwise at room temperature with stirring to a mixture of 15.0 g (78.8 mmol) of 4-(4-hydroxyphenyl)cyclohexanone and 12.4 g (90 mmol) of potassium carbonate in 100 ml of dimethylformamide formamide and the mixture is additionally stirred overnight. It is concentrated to dryness in vacuo and the residue is partitioned between water and ethyl acetate. The organic phase is dried and concentrated to dryness in vacuo. The residue is crystallized from cyclohexane.

Yield: 17.5 g (73% of theory),
Melting point: 78–80° C.
$R_f$: 0.50 (silica gel; cyclohexane/ethyl acetate 2:1)

b) 1-(4-tert-Butyloxycarbonylmethyloxyphenyl)-4-[(1-tertbutyloxycarbonylpiperidin-4-yl)methyleneimino] cyclohexane A mixture of 4.57 g (15 mmol) of 4-(4-tert-butyloxycarbonylmethyloxyphenyl)cyclohexanone, 3.21 g (15 mmol) of 1-(tertbutyloxycarbonyl)piperidin-4-ylmethylamine and 10 g of molecular sieve 3 Å in 100 ml of tolene is stirred overnight at room temperature. 0.75 g of 1-(tert-butyloxycarbonyl)piperidin-4-ylmethylamine are then added again and the mixture is stirred for a further 8 hours at 60° C. and then overnight at room temperature. The molecular sieve is filtered off and the filtrate is concentrated to dryness in vacuo.
Yield: 8.85 g of crude product.

EXAMPLE XIV

4-[(1-tert-Butyloxycarbonylpiperidin-4-yl)methoxy]-1-(4-hydroxyphenyl)piperidine a) 1-Benzyl-4-[(1-tert-butyloxycarbonylpiperidin-4-yl)methyloxy]piperidine 4.71 g (0.108 mol) of a 55% strength sodium hydride/oil suspension are added to a solution of 20 g (0.1 mol) of N-benzyl-4-hydroxypiperidine in 300 ml of dry tetrahydrofuran and the mixture is stirred for 4 hours at room temperature. After this time, a suspension of 29.3 g (0.1 mol) of 1-(1-tert-butyloxycarbonyl)piperidin-4-yl-2-methanesulphonyloxyethane in 30 ml of tetrahydrofuran is added, and the mixture is additionally stirred for 2 days at room temperature and then partitioned between water and ethyl acetate. The organic phase is dried and concentrated to dryness in vacuo. The residue is purified by means of chromatography on a silica gel column, methylene chloride/methanol (30:1) and (10:1) being used as eluent.
Yield: 16.6 g (42% of theory) of orange oil,
$R_f$: 0.17 (silica gel; methylene chloride/methanol=15:1)

b) 4-[(1-tert-Butyloxycarbonylpiperidin-4-yl)methyloxy] piperidine 8.04 g (21 mmol) of 1-benzyl-4-[(1-tert-butyloxycarbonylpiperidin-4-yl)methyloxy]piperidine are exhaustively hydrogenated analogously to Example 5 over palladium hydroxide on carbon in methanol.
Yield: 6.21 g (99% of theory).

c) 1-(4-Benzyloxyphenyl)-4-[(1-tert-butyloxycarbonyl-piperidin-4-yl)methoxy]piperidine A mixture of 600 mg (2 mmol) of 4-(1-tert-butyloxycarbonylpiperidin-4-yl)methoxy]piperidine, 526 mg (2 mmol) of 4-benzyloxybromobenzene, 314 mg (2.8 mmol) of potassium tert-butoxide, 23 mg (0.04 mmol) of bis(dibenzylideneacetone)palladium(O) and 24 mg (0.08 mmol) of tri-o-tolylphosphine in 20 ml of toluene is heated at reflux temperature for 6 hours under nitrogen. After cooling, the mixture is partitioned between water and ethyl acetate, and the organic phase is dried and evaporated to dryness. The residue which remains is purified by means of chromatography on a silica gel column, cyclohexane/ethyl acetate=2:1 being used as eluent.
Yield: 420 mg (44% of theory,
$R_f$: 0.35 (silica gel; cyclohexane/ethyl acetate 2:1)

d) 4-[(1-tert-Butyloxycarbonylpiperidin-4-yl)methoxy]-1-(4-hydroxyphenyl)piperidine 540 mg (1.1 mmol) of 1-(4-benzyloxyphenyl)-4-[(1-tert-butyloxycarbonylpiperidin-4-yl)methoxy]piperidine are exhaustively hydrogenated analogously to Example 5 on palladium on carbon (10% strength) in methanol.
Yield: 410 mg (93% of theory) of viscous oil,
$R_f$: 0.60 (silica gel; methylene chloride/methanol/conc. ammonia=9:1:0.1)

EXAMPLE XV

1-[2-(1-tert-Butyloxycarbonylpiperidin-4-yl)ethyl] piperazine a) 1-Benzyl-4-[2-(1-tert-butyloxycarbonylpiperidin-4-yl) ethyl]piperazine
Prepared from 1-(1-tert-butyloxycarbonyl)piperidin-4-yl-2-methanesulphonyloxyethane and 1-benzylpiperazine analogously to Example 3.
Yield: 21 g (90% of theory),
$R_f$: 0.50 (silica gel; methylene chloride/methanol/conc. ammonia=9:1:0.1)

b) 1-[2-(1-tert-Butyloxycarbonylpiperidin-4-yl)ethyl] piperazine
Prepared from 1-benzyl-4-[2-(1-tert-butyloxycarbonyl-piperidin-4-yl)ethyl]piperazine by exhaustive hydrogenation over palladium on carbon (10% strength) analogously to Example 5.
Yield: 12.4 g (95% of theory) of oil,
$R_f$: 0.19 (silica gel; methylene chloride/methanol/conc. ammonia=9:1:0.1)

EXAMPLE XVI 1-(trans-4-Methoxycarbonylmethyloxycyclohexyl) piperazin-2-one a) Methyl 4-trans-[N-(benzyloxycarbonylglycyl)-N-(2,2-diethoxyethyl)amino]cyclohexyloxyacetate
Prepared from N-benzyloxycarbonylglycine, methyl 4-trans-2,2-diethoxyethylaminocyclohexyloxyacetate and 2-(1H-benzotriazol-1-yl)-1,1,3,3-tetramethyluronium tetrafluoroborate analogously to Example IIId.
Yield: 2.42 g (93% of theory) of viscous oil,
$R_f$: 0.75 (silica gel; methylene chloride/methanol/conc. ammonia=9:1:0.1)

b) 4-Benzyloxycarbonyl-1-(trans-4-methoxycarbonylmethyloxycyclohexyl)piperazin-5-en-2-one
Prepared from methyl 4-trans-[N-(benzyloxycarbonylglycyl)-N-(2,2-diethoxyethyl)amino] cyclohexyloxyacetate and trifluoroacetic acid analogously to Example IIIe.
Yield: 1.33 g (68% of theory) of resin,
$R_f$: 0.55 (silica gel; methylene chloride/methanol/conc. ammonia=9:1:0.1)

c) 1-(trans-4-Methoxycarbonylmethyloxycyclohexyl) piperazin-2-one
Prepared by hydrogenation of 4-benzyloxycarbonyl-1-(trans-4-methoxycarbonylmethyloxycyclohexyl)piperazin-5-en-2-one analogously to Example IIIf.
Yield: 780 mg (90% of theory) of oil,
$R_f$: 0.45 (silica gel; methylene chloride/methanol/conc. ammonia=9:1:0.1)

EXAMPLE XVII

4-[2-(1-tert-Butyloxycarbonylpiperidin-4-yl)ethyl]-1-(piperidin-4-yl)piperazine a) 1-(1-Benzylpiperidin-4-yl)-4-[2-(1-tert-butyloxycarbonylpiperidin-4-yl)ethyl]piperazine
Prepared from 1-[2-(1-tert-butyloxycarbonylpiperidin-4-yl)ethyl]piperazine, 1-benzylpiperidin-4-one and sodium cyanborohydride analogously to Example 11.
Yield: 4.27 g (91% of theory),
$R_f$: 0.45 (silica gel; methylene chloride/methanol/conc. ammonia=9:1:0.1)

b) 4-[2-(1-tert-Butyloxycarbonylpiperidin-4-yl)ethyl]-1-(piperidin-4-yl)piperazine Prepared by hydrogenation of 1-(1-benzylpiperidin-4-yl)-4-[2-(1-tert-butyloxycarbonylpiperidin-4-yl)ethyl]piperazine over palladium on carbon (10% strength) analogously to Example 5.

Yield: 1.55 g (87% of theory),
$R_f$: 0.38 (silica gel; methylene chloride/methanol/conc. ammonia=4:1:0.25)

EXAMPLE XVIII trans-4-[(1-tert-Butyloxycarbonylpiperidin-4-yl)methyloxy]-1-(4-hydroxyphenyl)cyclohexane a) trans-4-(4-Hydroxyphenyl)cyclohexanol Prepared from 4-(4-hydroxyphenyl)cyclohexanone and sodium borohydride analogously to Example 10.

Yield: 3.9 g (68% of theory),
$R_f$: 0.34 (silica gel; methylene chloride/methanol=15:1)

b) trans-4-(4-Benzyloxyphenyl)cyclohexanol

A mixture of 3.9 g (0.02 mol) of trans-4-(4-hydroxyphenyl)cyclohexanol, 2.4 ml (0.02 mol) of benzyl bromide and 3.45 g (0.025 mol) of potassium carbonate in 30 ml of dimethylformamide is stirred at room temperature for one day, heated to 70° C. for one hour and then, after cooling, poured slowly with stirring into 200 ml of water. The precipitated crystals are filtered off and dried.

Yield: 5.07 g (89% of theory) of white crystals,
$R_f$: 0.45 (silica gel; methylene chloride/methanol=15:1)

c) trans-1-(4-Benzyloxyphenyl-4-[(1-tert-butyloxycarbonylpiperidine-4-yl)methyloxy]cyclohexane Prepared from trans-4-(4-benzyloxyphenyl)cyclohexanol and 1-(1-tert-butyloxycarbonyl)piperidin-4-yl-2-methanesulphonyloxyethane analogously to Example XIVa.

Yield: 1.3 g (39% of theory),
$R_f$: 0.55 (silica gel; cyclohexane/ethyl acetate=2:1)

d) trans-4-[(1-tert-Butyloxycarbonylpiperidin-4-yl)methyloxy]-1-(4-hydroxyphenyl)cyclohexane Prepared by hydrogenation of trans-1-(4-benzyloxyphenyl)-4-[(1-tert-butyloxycarbonylpiperidin-4-yl)methyloxy]cyclohexane on palladium on carbon (10% strength) analogously to Example 5.

Yield: 850 mg (81% of theory),
$R_f$: 0.45 (silica gel; cyclohexane/ethyl acetate=2:1)

EXAMPLE XIX

[(1-tert-Butyloxycarbonylpiperidin-4-yl)methoxy]cyclohexan-4-one a) 4-[(1-tert-Butyloxycarbonylpiperidin-4-yl)methyloxy]cyclohexane ethylene ketal Prepared from 4-hydroxycyclohexane ethylene ketal and 1-(1-tert-butyloxycarbonyl)piperidin-4-yl-2-methanesulphonyloxy-ethane analogously to Example XIVa.

Yield: 6.2 g (27% of theory) of oil,
$R_f$: 0.35 (silica gel; cyclohexane/ethyl acetate=1:1)

b) [(1-tert-Butyloxycarbonylpiperidin-4-yl)methoxy]cyclohexan-4-one

A solution of 8.5 g (0.024 mol) of 4-[(1-tert-butyloxycarbonylpiperidin-4-yl)methyloxy]cyclohexane ethylene ketal in 120 ml of glacial acetic acid and 30 ml of water is heated at 65° C. for 5 minutes. After cooling, it is partitioned between saturated sodium hydrogen carbonate solution and ethyl acetate. The aqueous phase is extracted a further three times with ethyl acetate. The combined organic extracts are dried and concentrated to dryness in vacuo. The residue is purified by means of chromatography on a silica gel column, cyclohexane/ethyl acetate=2:1 being used as eluent.

Yield: 4 g (54% of theory),
Melting point: 48–52° C.
$R_f$: 0.50 (silica gel; cyclohexane/ethyl acetate=1:1)

EXAMPLE XX 1-(3-Ethoxycarbonylmethyloxyphenyl)piperazine trifluoroacetate a) 4-tert-Butyloxycarbonyl-1-(3-hydroxyphenyl)piperazine Prepared by acidic hydrolysis of 1-(3-methoxyphenyl)piperazine with concentrated hydrochloric acid and subsequent reaction of the 1-(3-hydroxyphenyl)piperazine prepared in this way with di-tert-butyl dicarbonate analogously to Example IXa.

Yield: 6.5 g crude (quantitative) of oil,
$R_f$: 0.60 (silica gel; methylene chloride/methanol/conc. ammonia=9:1:0.1)

b) 4-tert-Butyloxycarbonyl-1-(3-ethoxycarbonylmethyloxyphenyl)piperazine

Prepared from 4-tert-butyloxycarbonyl-1-(3-hydroxyphenyl)piperazine, ethyl bromoacetate and potassium carbonate analogously to Example IXb.

Yield: 3.9 g (46% of theory) of amorphous solid,
$R_f$: 0.85 (silica gel; cyclohexane/ethyl acetate=1:1)

c) 1-(3-Ethoxycarbonylmethyloxyphenyl)piperazine trifluoroacetate

Prepared from 4-tert-butyloxycarbonyl-1-(3-ethoxycarbonylmethyloxyphenyl)piperazine and trifluoroacetic acid analogously to Example IXc.

Yield: 3 g (74% of theory), amorphous solid
$R_f$: 0.15 (silica gel; cyclohexane/ethyl acetate=1:1)

EXAMPLE XXI (S)-4-[1-(2-Ethoxycarbonylethyl)-3-isopropyloxycarbonylmethyl-2-oxo-piperazinyl]piperidine a) (S)-1-(2-Ethoxycarbonylethyl)-3-methoxycarbonylmethyl-2-oxo-piperazine 44 g of 1-ethyl-3-(3-dimethylaminopropyl)carbodiimide are added with stirring and cooling with ice to a solution of 0.8 g of N-(2,2-dimethoxyethyl)-ß-alanine ethyl ester and 1 g of 8-methyl N-benzyloxycarbonyl-L-aspartate in 20 ml of methylene chloride. This mixture is stirred further for 10 minutes with ice-cooling and then for 50 minutes at room temperature. 20 ml of water and 10 ml of a 5% strength aqueous potassium hydrogen sulphate solution are added with further stirring. The organic phase is separated off and the aqueous phase is extracted with 20 ml of methylene chloride. The combined organic phases are washed with water, dried over sodium sulphate and concentrated to dryness under reduced pressure. The residue which remains (1.3 g) is allowed to stand overnight at room temperature in 2.5 ml of trifluoroacetice acid and 0.5 g of p-toluenesulphonic acid is then added and the mixture is stirred for 4 hours at 70–75° C. After cooling, the toluene solution is washed with aqueous sodium hydrogen carbonate solution and concentrated to dryness under reduced pressure. The residue is purified by means of chromatography on a silica gel column, ethyl acetate/cyclohexane=1:1 being used as eluent. After evaporation, the residue (0.9 g) is dissolved in 25 ml of ethanol und exhaustively hydrogenated with hydrogen over 0.3 g of palladium on carbon (10% strength). The catalyst is filtered off and the filtrate is concentrated to dryness in vacuo. 0.9 g of a colourless oil remains.

b) (S)-1-Benzyloxycarbonyl-4-[1-(2-ethoxycarbonylethyl)-3-isopropyloxycarbonylmethyl-2-oxopiperazinyl]piperidine 2 g (0.0083 mol) of N-benzyloxycarbonyl-4-piperidone and 2.27 g (0.0083 mol) of (S)-1-(2-ethoxycarbonylethyl)-3-methoxycarbonylmethyl-2-oxopiperazine are dissolved in 40 ml of absolute ethanol and, after standing at room temperature for 2 hours, 3.4 g (0.016 mol) of triacetoxyborohydride, 2.8 ml (0.0092 mol) of titanium(IV) isopropoxide and 1.05 ml of acetic acid are added at room temperature with stirring and the mixture is stirred further overnight at room temperature. It is concentrated to dryness in vacuo and the residue is partitioned between ethyl acetate and sodium hydrogen carbonate solution and the aqueous phase is extracted twice more with ethyl acetate. The combined ethyl acetate phases are dried and concentrated to dryness in vacuo. The residue is purified on a silica gel column, methylene chloride which contains 2% or 3% methanol being used as eluent.

Yield: 1.64 g (66% of theory), $R_f$: 0.50 (silica gel; methylene chloride/methanol=9:1)

c) (S)-4-[1-(2-Ethoxycarbonylethyl)-3-isopropyloxycarbonylmethyl-2-oxopiperazinyl]piperidine 0.8 g (1.5 mmol) of (S)-1-benzyloxycarbonyl-1-[1-(2-ethoxycarbonylethyl)-3-isopropyloxycarbonylmethyl-2-oxopiperazinyl]piperidine are exhaustively hydrogenated at a hydrogen pressure of 50 psi over 0.5 g of palladium on carbon (10% strength) in 80 ml of ethanol. The catalyst is filtered off with suction and the filtrate is concentrated to dryness in vacuo.

Yield: 0.52 g (88% of theory), of oil, $R_f$: 0.10 (silica gel; methylene chloride/methanol=9:1)

EXAMPLE XXII

1-[4-(N-Acetyl-N-methoxycarbonylmethylamino)phenyl]piperazine hydrochloride a) 4-tert-Butyloxycarbonyl-4-(4-nitrophenyl)piperazine A solution of 16.5 g (0.067 mol) of 4-nitrophenylpiperazine in 500 ml of tetrahydrofuran is treated at room temperature and with stirring with 148 ml of 1N sodium hydroxide solution and then with 17.7 g (0.081 mol) of di-tert-butyl dicarbonate. The mixture is further stirred overnight at room temperature, then the tetrahydrofuran is distilled off under reduced pressure and the residue is extracted with ethyl acetate. The combined ethyl acetate extracts are washed with water, dried and concentrated to dryness in vacuo. The residue is triturated with ether, and the solid is filtered off with suction and dried.

Yield: 17.4 g (83.6% of theory),

Melting point: 146° C.

$R_f$: 0.8 (silica gel; methylene chloride/methanol=9.5:0.5)

b) 1-(4-Aminophenyl)-4-(4-tert-butyloxycarbonylpiperazine

A solution of 10.7 g (0.035 mol) of 4-tert-butyloxycarbonyl-1-(4-nitrophenyl)piperazine in 200 ml of ethyl acetate is exhaustively hydrogenated over 1 g of palladium on carbon (10% strength) at room temperature and under a hydrogen pressure of 50 psi in 200 ml of ethyl acetate. After filtering off the catalyst, the mother liquor is concentrated to dryness in vacuo.

Yield: 9.6 g (100% of theory) of oil, which crystallizes,

Melting point: 92° C.

$R_f$: 0.41 (silica gel; methylene chloride/methanol=9:1)

c) 1-(4-Acetaminophenyl)-4-tert-butyloxycarbonylpiperazine 2.8 g (0.01 mol) of 1-(4-aminophenyl)-4-tert-butyloxycarbonylpiperazine and 0.78 g=0.7 ml (0.01 mol) of acetyl chloride are dissolved in 50 ml of dry dimethylformamide, 1.3 g=1.8 ml (0.013 mol) of triethylamine are added dropwise with stirring and at room temperature and the mixture is stirred further overnight. It is then concentrated to dryness in vacuo and the residue is partitioned between ethyl acetate and 1N hydrochloric acid. The combined organic extracts are washed with saturated sodium hydrogen carbonate solution, dried and concentrated to dryness in vacuo.

Yield: 2.0 g (62.0% of theory),

Melting point: 143° C.

$R_f$: 0.49 (silica gel; methylene chloride/methanol=9:1)

d) 1-[4-(N-Acetyl-N-methoxycarbonylmethylamino)phenyl]-1-tert-butyloxycarbonylpiperazine 0.74 g (6.6 mmol) of potassium tert-butoxide is added at room temperature and with stirring to a solution of 2.0 g (6.3 mmol) of 1-(4-acetaminophenyl)-4-tert-butyloxycarbonylpiperazine in 20 ml of dimethyl sulphoxide and the mixture is stirred for a further 30 minutes. 1.0 g=0.6 ml (6.3 mmol) of methyl bromoacetate is then added dropwise with further stirring and the mixture is stirred further overnight at room temperature. After this time, it is poured onto water and extracted with methylene chloride. The combined organic extracts are washed successively with 0.5 molar potassium hydrogen sulphate solution and saturated sodium hydrogen carbonate solution, dried and evaporated to dryness in vacuo.

Yield: 1.8 g (73.4% of theory),

Mass spectrum: $M^+=391$ $R_f$: 0.55 (silica gel; methylene chloride/methanol=9:1)

e) 1-[4-(N-Acetyl-N-methoxycarbonylmethylamino)phenyl]piperazine hydrochloride 15 ml of ethereal hydrochloric acid are added to a solution of 1.77 g (4.5 mmol) of 1-[4-(N-acetyl-N-methoxycarbonylmethylamino)phenyl]-4-tert-butyloxycarbonylpiperazine in 20 ml of methanol and the mixture is allowed to stand at room temperature for 5 hours. It is then concentrated to dryness in vacuo.

Yield: 1.5 g (quantitative) of oil, $R_f$: 0.13 (silica gel; methylene chloride/methanol=9:1)

EXAMPLE XXIII

1-[4-(N-n-Butylsulphonyl-N-methoxycarbonylmethylamino)phenyl]piperazine hydrochloride a) 4-tert-Butyloxycarbonyl-1-(4-n-butylsulphonylaminophenyl)piperazine 2.8 g (0.01 mol) of 1-(4-aminophenyl)-4-tert-butyloxycarbonylpiperazine and 1.7 g=1.4 ml (0.01 mol) of n-butanesulphonyl chloride are dissolved in 50 ml of dry methylene chloride, 1.0 g=1.0 ml (0.013 mol) of pyridine is added dropwise with stirring and at room temperature and the mixture is stirred further overnight. It is then concentrated to dryness in vacuo and the residue is partitioned between ethyl acetate and 1N hydrochloric acid. The combined organic extracts are washed with saturated sodium hydrogen carbonate solution, dried and concentrated to dryness in vacuo.

Yield: 3.9 g (quantitative) of oil,

Mass spectrum: $M^+=397$ $R_f$: 0.52 (silica gel; methylene chloride/methanol=9:1)

b) 4-tert-Butyloxycarbonyl-1-[4-(N-n-butylsulphonyl-N-methoxycarbonylmethylamino)phenyl]piperazine Prepared from 4.0 g (0.01 mol) of 4-tert-butyloxycarbonyl-1-(4-n-butylsulphonylaminophenyl)piperazine, 1.3 g (0.011 mol) of potassium tert-butoxide and 1.8 g=1.1 ml (0.011 mol) of methyl bromoacetate in 10 ml of dry dimethyl sulphoxide analogously to Example XXIId.

Yield: 4.6 g (97.3% of theory) of oil, $R_f$: 0.73 (silica gel; methylene chloride/methanol=9:1)

c) 1-[4-(N-n-Butylsulphonyl-N-methoxycarbonylmethylamino)phenyl]piperazine hydrochloride Prepared from 3.0 g (6.4 mol) of 4-tert-butyloxycarbonyl-1-[4-(N-n-butylsulphonyl-N-methoxycarbonylmethylamino)phenyl]piperazine and 10 ml of ethereal hydrochloric acid in 10 ml of methanol analogously to Example XXIIe.

Yield: 2.6 g (quantitative) of oil, $R_f$: 0.27 (silica gel; methylene chloride/methanol=9:1)

Preparation of the final products:

EXAMPLE 1

1-(4-Carboxymethyloxyphenyl)-4-[2-(piperidin-4-yl)ethyl]piperazine dihydrochloride A solution of 450 mg (1.2 mmol) of 1-(4-methoxycarbonylmethyloxyphenyl)-4-[2-(piperidin-4-yl)ethyl]piperazine dihydrochloride in 25 ml of 3N hydrochloric acid is allowed to stand at room temperature for 5 hours and then concentrated to dryness in vacuo. The solid residue which remains is triturated with acetone, filtered off with suction and dried.

Yield: 400 mg (76% of theory),

Melting point: 258–260° C.

Mass spectrum: (M+H)$^+$=348

$R_f$: 0.08 (silica gel; methylene chloride/methanol/conc. ammonia=4:1:0.2)

The following compounds can be prepared analogously to Example 1:

(1) 1-(4-Carboxymethyloxyphenyl)-4-[2-(piperidin-4-yl)ethyl]piperazin-2-one dihydrochloride Prepared from 1-(4-ethoxycarbonylmethyloxyphenyl)-4-[2-(piperidin-4-yl)ethyl]piperazin-2-one dihydrochloride.

Yield: 96% of theory of amorphous solid,

Mass spectrum: M$^+$=361

$R_f$: 0.70 (reversed-phase plate RP 18; methanol/50% strength sodium chloride solution=3:2)

(2) 1-[4-(2-Carboxyethyl)phenyl]-4-[2-(piperidin-4-yl)ethyl]piperazine dihydrochloride Prepared from 1-[4-(2-methoxycarbonylethyl)phenyl]-4-[2-(piperidin-4-yl)ethyl]piperazine dihydrochloride.

Yield: 98% of theory,

Melting point: 268–271° C. (dec.)

Mass spectrum: (M+H)$^+$=346

$R_f$: 0.65 (reversed-phase plate RP 18; methanol/50% strength sodium chloride solution=3:2)

(3) 1-[3,4-Di(carboxymethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[3,4-di(methoxycarbonylmethyloxy)phenyl]piperazine.

Yield: 99% of theory,

Melting point: 118–121° C. (dec.)

Mass spectrum: M$^+$=421

$R_f$: 0.65 (reversed-phase plate RP 18; methanol/50% strength sodium chloride solution=3:2)

(4) 1-(4-Carboxymethyloxyphenyl)-4-[(piperidin-4-yl)acetyl]piperazine hydrochloride Prepared from 1-(4-methoxycarbonylmethyloxyphenyl)-4-[(piperidin-4-yl)acetyl]piperazine hydrochloride.

Yield: 93% of theory,

Melting point: 88–90° C.

Mass spectrum: M$^+$=361

$R_f$: 0.08 (silica gel; methylene chloride/methanol/conc. ammonia=4:1:0.2)

(5) 1-(4-Carboxymethyloxyphenyl)-4-[(piperidin-4-yl)aminocarbonyl]piperazine hydrochloride Prepared from 1-(4-methoxycarbonylmethyloxyphenyl)-4-[(piperidin-4-yl)aminocarbonyl]piperazine hydrochloride.

Yield: 91% of theory,

Melting point: 73–78° C.

Mass spectrum: (M+H)$^+$=363

$R_f$: 0.18 (silica gel; methylene chloride/methanol/conc. ammonia=2:1:0.25)

(6) 1-(4-Carboxymethyloxyphenyl)-4-[(4-piperazinyl)carbonylmethyl]piperazine

Prepared from 1-(4-methoxycarbonylmethyloxyphenyl)-4-[(4-piperazinyl)carbonylmethyl]piperazine dihydrochloride.

Yield: 62% of theory,

Melting point: 248–252° C.

Mass spectrum: M$^+$=362

$R_f$: 0.40 (silica gel; methylene chloride/methanol/conc. ammonia=2:1:0.25)

(7) 1-(4-Carboxymethyloxyphenyl)-2-methyl-4-[2-(piperidin-4-yl)ethyl]piperazine dihydrochloride Prepared from 1-(4-methoxycarbonylmethyloxyphenyl)-2-methyl-4-[2-(piperidin-4-yl)ethyl]piperazine dihydrochloride.

Yield: 83% of theory of amorphous solid,

Mass spectrum: M$^+$=361

$R_f$: 0.70 (reversed-phase plate RP 18; methanol/5% strength sodium chloride solution=3:2)

(8) 1-(4-Carboxymethyloxyphenyl)-4-[2-(piperazin-4-yl)ethyl]piperazine dihydrochloride Prepared from 1-(4-methoxycarbonylmethyloxyphenyl)-4-[2-(piperazin-4-yl)ethyl]piperazine dihydrochloride.

Yield: 78% of theory,

Melting point: 253–256° C.

Mass spectrum: M$^+$=348

$R_f$: 0.07 (silica gel; methylene chloride/methanol/conc. ammonia=4:1:0.2)

(9) 1-(4-Carboxymethylphenyl)-4-[2-(piperazin-4-yl)ethyl]piperazine dihydrochloride Prepared from 1-(4-methoxycarbonylmethylphenyl)-4-[2-(piperazin-4-yl)ethyl]piperazine dihydrochloride.

Yield: 69% of theory,

Melting point: 235–238° C.

Mass spectrum: M$^+$=332

$R_f$: 0.35 (silica gel; methylene chloride/methanol/conc. ammonia=2:1:0.25)

(10) (S)-1-(4-Carboxymethyloxyphenyl)-3-(4-methoxybenzyl)-4-[2-(piperidin-4-yl)ethyl]piperazin-2-one dihydrochloride Prepared from (S)-1-(4-ethoxycarbonylmethyloxyphenyl)-3-(4-methoxybenzyl)-4-[2-(piperidin-4-yl)ethyl]piperazin-2-one dihydrochloride.

Yield: 81% of theory,
Melting point: 109–115° C. (dec.)
Mass spectrum: (M+H)⁺=482
$R_f$: 0.55 (reversed-phase plate RP 18; methanol/5% strength sodium chloride solution=3:2)

(11) 1-[2,4-Di(carboxymethyloxy)phenyl]-4-[2-(piperidin-4-yl)ethyl]piperazine dihydrochloride Prepared from 1-[2,4-di(ethoxycarbonylmethyloxy)phenyl]4-[2-(piperidin-4-yl)ethyl]piperazine dihydrochloride.

(12) 1-[3,5-Di(carboxymethyloxy)phenyl]-4-[2-(piperidin-4-yl)ethyl]piperazine dihydrochloride Prepared from 1-[3,5-di(ethoxycarbonylmethyloxyphenyl]-4-[2-(piperidin-4-yl)ethyl]piperazine dihydrochloride.

(13) 1-(3-Carboxymethyloxyphenyl)-4-[2-(piperidin-4-yl)ethyl]piperazine dihydrochloride Prepared from 1-(3-methoxycarbonylmethyloxyphenyl)-4-[2-(piperidin-4-yl)ethyl]piperazine dihydrochloride.
Yield: 98% of theory,
Melting point: 218–220° C.
Mass spectrum: M⁺=347
$R_f$: 0.20 (silica gel; methylene chloride/methanol/ammonia=2:1:0.25)

(14) 1-(4-Carboxymethyloxyphenyl)-4-[(piperidin-4-yl)oxycarbonyl]piperazine hydrochloride Prepared from 1-(4-tert-butyloxycarbonylmethyloxyphenyl)-4-[(piperidin-4-yl)oxycarbonyl]piperazine hydrochloride and trifluoroacetic acid.

(15) 1-(2-Carboxybenzo-1,3-dioxol-5-yl)-4-[2-(piperidin-4-yl)ethyl]piperazine dihydrochloride Prepared from 1-(2-ethoxycarbonylbenzo-1,3-dioxol-5-yl)-4-[2-(piperidin-4-yl)ethyl]piperazine dihydrochloride.

(16) 1-(4-Carboxymethyloxyphenyl)-4-[2-(piperidin-4-yl)ethyl]piperidine hydrochloride Prepared from 1-(4-ethoxycarbonylmethyloxyphenyl)-4-[2-(piperidin-4-yl)ethyl]piperidine hydrochloride.

(17) 1-(4-Carboxymethylaminophenyl)-4-[2-(piperidin-4-yl)ethyl]piperazine dihydrochloride Prepared from 1-(4-ethoxycarbonylmethylaminophenyl)-4-[2-(piperidin-4-yl)ethyl]piperazine dihydrochloride.

(18) 1-(4-Carboxymethyloxyphenyl)-2-(4-methoxybenzyl)-4-[2-(piperidin-4-yl)ethyl]piperazin-3-one hydrochloride Prepared from 1-(4-ethoxycarbonylmethyloxyphenyl)-2-(4-methoxybenzyl)-4-[2-(piperidin-4-yl)ethyl]piperazin-3-one hydrochloride.

(19) (S)-4-[1-(2-Carboxyethyl)-3-isopropyloxycarbonyl-2-oxo-piperazinyl]-1-[2-(piperidin-4-yl)ethyl]piperidine hydrochloride Prepared from (S)-4-[1-(2-ethoxycarbonylethyl)-3-isopropyloxycarbonylmethyl-2-oxopiperazinyl]-1-[2-(piperidin-4-yl)ethyl]piperidine hydrochloride.
Yield: 83% of theory, amorphous
Mass spectrum: (M+H)=467
$R_f$: 0.65 (reversed-phase plate RP 18; methanol/5% strength sodium chloride solution=3:2)

(20) (R)-2-Benzyl-1-(4-carboxymethyloxyphenyl)-4-[2-(piperidin-4-yl)ethyl]piperazin-3-one hydrochloride Prepared from (R)-2-benzyl-1-(4-ethoxycarbonylmethyloxyphenyl)-4-[2-(piperidin-4-yl)ethyl]piperazin-3-one hydrochloride.

(21) trans-1-(4-Carboxymethyloxyphenyl)-4-[(piperidin-4-yl)methylamino]cyclohexane dihydrochloride Prepared from trans-1-(4-tert-butyloxycarbonylmethyloxyphenyl)-4-(1-tert-butyloxycarbonylpiperidin-4-yl)methylamino]cyclohexane and 6N hydrochloric acid/acetic acid=1:1.
Yield: 98% of theory,
Melting point: 309–311° C. (dec.)
Mass spectrum: M⁺=346
$R_f$: 0.12 (silica gel; methylene chloride/methanol/conc. ammonia=2:1:0.25)

(22) trans-1-(4-Carboxymethyloxyphenyl)-4-[(piperidin-4-yl)-N-methylmethylamino]cyclohexane dihydrochloride Prepared from trans-1-(4-tert-butyloxycarbonylmethyloxyphenyl)-4-[(1-tert-butyloxycarbonylpiperidin-4-yl)-N-methylmethylamino]cyclohexane and 6N hydrochloric acid/acetic acid=1:1.
Yield: 99% of theory,
Melting point: 123–126° C. (dec.)
Mass spectrum: M⁺=360
$R_f$: 0.18 (silica gel; methylene chloride/methanol/conc. ammonia=2:1:0.25)

(23) 1-(4-Carboxymethyloxyphenyl)-4-[(piperidin-4-yl)methyloxy]piperidine hydrochloride Prepared from 1-(4-methyloxycarbonylmethyloxyphenyl)-4-[(piperidin-4-yl)methyloxy]piperidine hydrochloride.
Yield: 99% of theory, amorphous solid
Mass spectrum: M⁺=348
$R_f$: 0.30 (silica gel; methylene chloride/methanol/conc. ammonia 2:1:0.25)

(24) 1-[1-(2-Carboxyethyl)piperidin-4-yl]-4-[2-(piperidin-4-yl)ethyl]piperazin trihydrochloride Prepared from 1-[1-(2-methoxycarbonylethyl)piperidin-4-yl]-4-[2-(piperidin-4-yl)ethyl]piperazine trihydrochloride.
Yield: 99% of theory,
Melting point: 341–345° C. (dec.)
Mass spectrum: M⁺=352
$R_f$: 0.09 (silica gel; methylene chloride/methanol/conc. ammonia=2:1:0.25)

(25) trans-1-(4-Carboxymethyloxyphenyl)-4-[(piperidin-4-yl)methyloxy)]cyclohexane hydrochloride Prepared from trans-1-(4-methoxycarbonylmethyloxyphenyl)-4-[(piperidin-4-yl)methyloxy]cyclohexane hydrochloride and 6N hydrochloric acid/acetic acid=1:1.

Yield: 95% of theory,
Melting point: 242–245° C. (dec.)
Mass spectrum: (M+H)⁺=348
$R_f$: 0.40 (silica gel; methylene chloride/methanol/conc. ammonia=2:1:0.25)

(26) trans-1-(4-Carboxymethyloxyphenyl)-4-[(piperidin-4-yl)-N-acetylmethylamino]cyclohexane hydrochloride Prepared from trans-1-(4-methoxycarbonylmethyloxyphenyl)-4-[(piperidin-4-yl)-N-acetylmethylamino]cyclohexane hydrochloride and 6N hydrochloric acid.
Yield: quantitative,
Melting point: 113–115° C. (dec.)
Mass spectrum: M⁺=388
$R_f$: 0.35 (silica gel; methylene chloride/methanol/conc. ammonia=2:1:0.25)

(27) trans-1-(4-Carboxymethyloxypiperidino)-4-[(piperidin-4-yl)methyloxy]cyclohexane ditrifluoroacetate Prepared from trans-1-(4-tert-butyloxycarbonylmethyloxypiperidino)-4-[(1-tert-butyloxycarbonylpiperidin-4-yl)methyloxy]cyclohexane and trifluoroacetic acid.
Yield: quantitative, of resin
Mass spectrum: M⁺=354
$R_f$: 0.10 (silica gel; methylene chloride/methanol/conc. ammonia=2:1:0.2)

(28) 1-(3-Carboxymethyloxypyridazin-6-yl)-4-[2-(piperidin-4-yl)ethyl]piperazine dihydrochloride Prepared from 4-[2-(1-tert-butyloxycarbonylpiperidin-4-yl)ethyl]-1-(3-methoxycarbonylmethyloxypyridazin-6-yl)piperazine.
Yield: 6% of theory,
Melting point: 265–270° C.
Mass spectrum: (M+H)⁺=350
$R_f$: 0.20 (silica gel; methylene chloride/methanol/conc. ammonia=2:1:0.2)

(29) cis/trans-1-(4-Carboxymethylpiperazino)-4-[(piperidin-4-yl)methyloxy]cyclohexane trihydrochloride Prepared from cis/trans-1-(4-methoxycarbonylmethylpiperazino)-4-[(piperidin-4-yl)methyloxy]cyclohexane trihydrochloride.
Yield: quantitative,
Mass spectrum: (M+H)⁺=340
$R_f$: 0.13 (silica gel; methylene chloride/methanol/conc. ammonia=2:1:0.2)

(30) cis/trans-1-[4-(1-Carboxyprop-2-yl)piperazino]-4-[(piperidin-4-yl)methyloxy]cyclohexane trihydrochloride Prepared from cis/trans-1-[4-(1-methoxycarbonylprop-2-yl)piperazino]-4-[(piperidin-4-yl)methyloxy]cyclohexane trihydrochloride.
Yield: 80% of theory,
Melting point: 90–110° C.
Mass spectrum: (M+H)⁺=368
$R_f$: 0.15 (silica gel; methylene chloride/methanol/conc. ammonia=2:1:0.2)

(31) 1-(4-Carboxymethyloxyphenyl)-4-[(piperidin-4-yl)methylamino]piperidine dihydrochloride Prepared from 1-(4-methoxycarbonylmethyloxyphenyl)-4-[(piperidin-4-yl)methylamino]piperidine dihydrochloride.

(32) 1-(4-Carboxymethyloxyphenyl)-4-[(piperidin-4-yl)-N-methylmethylamino]piperidine dihydrochloride Prepared from 1-(4-methoxycarbonylmethyloxyphenyl)-4-[(piperidin-4-yl)-N-methylmethylamino]piperidine dihydrochloride.

(33) 1-(4-Carboxymethyloxyphenyl)-4-[(piperidin-4-yl)-N-benzylmethylamino]piperidine dihydrochloride Prepared from 1-(4-methoxycarbonylmethyloxyphenyl)-4-[(piperidin-4-yl)-N-benzylmethylamino]piperidine dihydrochloride.

(34) 1-(4-Carboxymethyloxyphenyl)-4-[(piperidin-4-yl)aminomethyl]piperidine dihydrochloride Prepared from 1-(4-methoxycarbonylmethyloxyphenyl)-4-[(piperidin-4-yl)aminomethyl]piperidine dihydrochloride.

(35) 1-(4-Carboxymethyloxyphenyl)-4-[(piperidin-4-yl)-N-benzylaminomethyl]piperidine dihydrochloride Prepared from 1-(4-methoxycarbonylmethyloxyphenyl)-4-[(piperidin-4-yl)-N-benzylaminomethyl]piperidine dihydrochloride.

(36) 4-(4-Carboxymethyloxyphenyl)-1-[2-(piperidin-4-yl)ethyl]piperidine dihydrochloride Prepared from 4-(4-methoxycarbonylmethyloxyphenyl)-1-[2-(piperidin-4-yl)ethyl]piperidine dihydrochloride.

(37) 1-[4-(1,2-Dicarboxyethyloxy)phenyl]-4-[2-(piperidin-4-yl)ethyl]piperazine dihydrochloride Prepared from 1-[4-(1,2-dimethoxycarbonylethoxy)phenyl)-4-[2-(piperidin-4-yl)ethyl]piperazine dihydrochloride.

(38) 1-[4-(1-Carboxy-2-phenylethyloxy)phenyl]-4-[2-(piperidin-4-yl)ethyl]piperazine dihydrochloride Prepared from 1-[4-(1-methoxycarbonyl-2-phenylethyloxyphenyl]-4-[2-(piperidin-4-yl)ethyl]piperazine dihydrochloride.

(39) 1-[4-(1-Carboxy-3-hydroxypropyloxy)phenyl]-4-[2-(piperidin-4-yl)ethyl]piperazine dihydrochloride Prepared from 1-[4-(1-methoxycarbonyl-3-hydroxypropyl)phenyl]-4-[2-(piperidin-4-yl)ethyl]piperazine dihydrochloride.

(40) 1-[4-(1-Carboxy-2-(4-chlorophenyl)ethyloxy)phenyl]-4-[2-(piperidin-4-yl)ethyl]piperazine dihydrochloride Prepared from 1-[4-(2-(4-chlorophenyl)-1-methoxycarbonylethyloxy]phenyl]-4-[2-(piperidin-4-yl)ethyl]piperazine dihydrochloride.

(41) 1-(4-Carboxymethyloxyphenyl)-4-[2-(piperidin-4-yl)ethyl]piperazin-3-one hydrochloride Prepared from 1-(4-ethoxycarbonylmethyloxyphenyl)-4-[2-(piperidin-4-yl)ethyl]piperazin-3-one hydrochloride.

(42) 1-(4-Carboxymethyloxyphenyl)-4-[2-(piperidin-4-yl)ethyl]piperazine-2,5-dione hydrochloride Prepared from 1-(4-ethoxycarbonylmethyloxyphenyl)-4-[2-(piperidin-4-yl)ethyl]piperazine-2,5-dione hydrochloride.

(43) 1-[4-(N-Acetyl-N-carboxymethylamino) phenyl]-4-[2-(piperidin-4-yl)ethyl]piperazine dihydrochloride Prepared from 1-[4-(N-acetyl-N-methoxycarbonylmethylamino)phenyl]-4-[2-(piperidin-4-yl)ethyl]piperazine dihydrochloride.

Yield: 78.3% of theory,
Melting point: 118–121° C.
Mass spectrum: $M^+$=388
$R_f$: 0.19 (silica gel; methylene chloride/methanol/conc. ammonia=2:1:0.25)

(44) 1-[4-(N-n-Butylsulphonyl-N-carboxymethylamino)phenyl]-4-[2-(piperidin-4-yl) ethyl]piperazine dihydrochloride Prepared from 1-[4-(N-n-butylsulphonyl-N-methoxycarbonylmethylamino)phenyl]-4-[2-(piperidin-4-yl)ethyl]piperazine dihydrochloride.

Yield: 75.9% of theory,
Melting point: 104–105° C.
Mass spectrum: $M^+$=466
$R_f$: 0.22 (silica gel; methylene chloride/methanol/conc. ammonia=2:1:0.25)

EXAMPLE 2

1-(4-Methoxycarbonylmethyloxyphenyl)-4-[2-(piperidin-4-yl)ethyl]piperazine dihydrochloride A solution of 1.0 g (2.2 mmol) of 4-[2-(1-tert-butyloxycarbonylpiperidin-4-yl)ethyl]-1-(4-methoxycarbonylmethyloxyphenyl)piperazine in 20 ml of methanol and 30 ml of ethereal hydrochloric acid is allowed to stand at room temperature for 5 hours. It is then concentrated to dryness in vacuo. The solid residue which remains is triturated with acetone, filtered off with suction and dried.

Yield: 900 mg (96% of theory),
Melting point: 225–227° C.
Mass spectrum: $M^+$=361
$R_f$: 0.08 (silica gel; methylene chloride/methanol 9:1)

The following compounds can be prepared analogously to Example 2:

(1) 1-(4-Ethoxycarbonylmethyloxyphenyl)-4-[2-(piperidin-4-yl)ethyl]piperazin-2-one dihydrochloride Prepared from 4-[2-(1-tert-butyloxycarbonylpiperidin-4-yl)ethyl]-1-(4-ethoxycarbonylmethyloxyphenyl)piperazin-2-one and ethereal hydrochloric acid.

Yield: 92% of theory,
Melting point: 212–217° C. (dec.)
Mass spectrum: $M^+$=389
$R_f$: 0.09 (silica gel; methylene chloride/methanol=9:1)

(2) 1-[4-(2-Methoxycarbonylethyl)phenyl]-4-[2-(piperidin-4-yl)ethyl]piperazine dihydrochloride Prepared from 4-[2-(1-tert-butyloxycarbonylpiperidin-4-yl)ethyl]-1-[4-(2-methoxycarbonylethyl)phenyl]piperazine and trifluoroacetic acid.

Yield: 96% of theory,
Melting point: 253–256° C. (dec.)
Mass spectrum: $M^+$=359
$R_f$: 0.36 (silica gel; methylene chloride/methanol/conc. ammonia=4:1:0.2)

(3) 1-(4-Methoxycarbonylmethyloxyphenyl)-4-[(piperidin-4-yl)acetyl]piperazine hydrochloride Prepared from 4-[(1-tert-butyloxycarbonylpiperidin-4-yl)acetyl]-1-(4-methoxycarbonylmethyloxyphenyl)piperazine and ethereal hydrochloric acid.

Yield: 82% of theory,
Melting point: 98–99° C.
Mass spectrum: $M^+$=375
$R_f$: 0.10 (silica gel; methylene chloride/methanol=9:1)

(4) 1-(4-Methoxycarbonylmethyloxyphenyl)-2-methyl-4-[2-(piperidin-4-yl)ethyl]piperazine dihydrochloride Prepared from 4-[2-(1-tert-butyloxycarbonylpiperidin-4-yl)ethyl]-1-(4-methoxycarbonylmethyloxyphenyl)-2-methylpiperazine and trifluoroacetic acid.

Yield: 27% of theory,
Melting point: 230–231° C. (dec.)
Mass spectrum: $M^+$=375
$R_f$: 0.25 (silica gel; methylene chloride/methanol/conc. ammonia=9:1:0.1)

(5) 1-(4-Methoxycarbonylmethyloxyphenyl)-4-[2-(piperazin-4-yl)ethyl]piperazine dihydrochloride Prepared from 4-[2-(1-tert-butyloxycarbonylpiperazin-4-yl)ethyl]-1-(4-methoxycarbonylmethyloxyphenyl)piperazine and trifluoroacetic acid.

Yield: 93% of theory,
Melting point: 210–212° C. (sintering from 160° C.)
Mass spectrum: $M^+$=362
$R_f$: 0.13 (silica gel; methylene chloride/methanol/conc. ammonia=9:1:2.1)

(6) 1-(4-Methoxycarbonylmethylphenyl)-4-[2-(piperazin-4-yl)ethyl]piperazine dihydrochloride Prepared from 4-[2-(1-tert-butyloxycarbonylpiperazin-4-yl)ethyl]-1-(4-methoxycarbonylmethylphenyl)piperazine and trifluoroacetic acid.

Yield: 93% of theory,
Melting point: 238–242° C.
Mass spectrum: $M^+$=346
$R_f$: 0.25 (silica gel; methylene chloride/methanol/conc. ammonia=4:1:0.2)

(7) (S)-1-(4-Ethoxycarbonylmethyloxyphenyl)-3-(4-methoxybenzyl)-4-[2-(piperidin-4-yl)ethyl] piperazin-2-one dihydrochloride Prepared from (S)-4-[2-(1-tert-butyloxycarbonylpiperidin-4-yl)ethyl]-1-(4-ethoxycarbonylmethyloxyphenyl)-3-(4-methoxybenzylpiperazin-2-one and trifluoroacetic acid.

Yield: 77% of theory, foam
Melting point: 212–217° C. (dec.)
Mass spectrum: $M^+$=509
$R_f$: 0.20 (silica gel; methylene chloride/methanol=9:1)

(8) 1-[2,4-Di(ethoxycarbonylmethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[2,4-di(ethoxycarbonylmethyloxy)phenyl]piperazine and trifluoroacetic acid.

(9) 1-[3,5-Di(ethoxycarbonylmethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[3,5-di(ethoxycarbonylmethyloxy)phenyl]piperazine and trifluoroacetic acid.

(10) 1-(3-Methoxycarbonylmethyloxyphenyl)-4-[2-(piperidin-4-yl)ethyl]piperazine dihydrochloride Prepared from 4-[2-(1-tert-butyloxycarbonylpiperidin-4-yl)ethyl]-1-(3-ethoxycarbonylmethyloxyphenyl)piperazine and ethereal hydrochloric acid in methanol.

Yield: 34% of theory,
Melting point: >270° C.
Mass spectrum: M$^+$=361
R$_f$: 0.65 (silica gel; methylene chloride/methanol/conc. ammonia 2:1:0.25)

(11) 1-(2-Ethoxycarbonylbenzo-1,3-dioxo-5-yl)-4-[2-(piperidin-4-yl)ethyl]piperazine dihydrochloride Prepared from 4-[2-(1-tert-butyloxycarbonylpiperidin-4-yl)ethyl]-1-(2-ethoxycarbonylbenzo-1,3-dioxo-5-yl)piperazine and trifluoroacetic acid.

(12) 1-(4-Ethoxycarbonylmethyloxyphenyl)-4-[2-(piperidin-4-yl)ethyl]piperidine hydrochloride Prepared from 4-[2-(1-tert-butyloxycarbonylpiperidin-4-yl)ethyl]-1-(4-ethoxycarbonylmethyloxyphenyl)piperidine and trifluoroacetic acid.

(13) 1-(4-Ethoxycarbonylmethylaminophenyl)-4-[2-(piperidin-4-yl)ethyl]piperazine dihydrochloride Prepared from 4-[2-(1-tert-butyloxycarbonylpiperidin-4-yl)ethyl]-1-(4-ethoxycarbonylmethyloxyphenyl)piperazine and trifluoroacetic acid.

(14) 1-(4-Ethoxycarbonylmethyloxyphenyl)-2-(4-methoxybenzyl)-4-[2-(piperidin-4-yl)ethyl]piperazin-3-one hydrochloride Prepared from 4-[2-(1-tert-butyloxycarbonylpiperidin-4-yl)ethyl]-1-(4-ethoxycarbonylmethyloxyphenyl)-2-(4-methoxybenzyl)piperazin-3-one and trifluoroacetic acid.

(15) (S)-4-[1-(2-Ethoxycarbonylethyl)-3-isopropyloxycarbonylmethyl-2-oxopiperazinyl]-1-[2-(piperidin-4-yl)ethyl]piperidine hydrochloride Prepared from (S)-4-[2-(1-tert-butyloxycarbonyl-piperidin-4-yl)ethyl]-4-[1-(2-ethoxycarbonylethyl)-3-isopropyloxycarbonylmethyl]-2-oxopiperazinyl]piperidine and trifluoroacetic acid.

Mass spectrum: (M+H)$^+$=495
R$_f$: 0.10 (silica gel; methylene chloride/methanol=9:1)

(16) (R)-2-Benzyl-1-(4-ethoxycarbonylmethyloxyphenyl)-4-[2-(piperidin-4-yl)ethyl]piperazin-3-one hydrochloride Prepared from (R)-2-benzyl-4-[2-(1-tert-butyloxycarbonylpiperidin-4-yl)ethyl]-1-(4-ethoxycarbonylmethyloxyphenyl)piperazin-3-one and trifluoroacetic acid.

(17) 1-(4-Methoxycarbonylmethyloxyphenyl)-4-[(piperidin-4-yl)methyloxy]piperidine hydrochloride Prepared from 4-[(1-tert-butyloxycarbonylpiperidin-4-yl)methyloxy]-1-(4-methoxycarbonylmethyloxyphenyl)piperazine and ethereal hydrochloric acid.

Yield: quantitative,
Melting point: 195–198° C.
Mass spectrum: M$^+$=362
R$_f$: 0.12 (silica gel; methylene chloride/methanol/conc. ammonia=9:1:0.1)

(18) 1-(trans-4-Carboxylmethyloxycyclohexyl)-4-[2-(piperidin-4-yl)ethyl]piperazine dihydrochloride Prepared from 4-[2-(1-tert-butyloxycarbonylpiperidin-4-yl)ethyl]-1-(trans-4-carboxymethyloxycyclohexyl)piperazine and conc. hydrochloric acid/water=1:1.

Yield: quantitative,
Melting point: 288–289° C. (dec.)
Mass spectrum: (M+H)$^+$=354
R$_f$: 0.12 (silica gel; methylene chloride/methanol/conc. ammonia=2:1:0.25)

(19) 1-(trans-4-Methoxycarbonylmethyloxycyclohexyl)-4-[2-(piperidin-4-yl)ethyl]piperazin-2-one dihydrochloride Prepared from 4-[2-(1-tert-butyloxycarbonylpiperidin-4-yl)ethyl]-1-(trans-4-methoxycarbonylmethyloxycyclohexyl)piperazin-2-one and ethereal hydrochloric acid.

Yield: 80% of theory,
Melting point: 255–256° C. (dec.)
Mass spectrum: M$^+$=381
R$_f$: 0.26 (silica gel; methylene chloride/methanol/conc. ammonia=4:1:0.25)

(20) 1-(1-Methoxycarbonylmethylpiperidin-4-yl)-4-[2-(piperidin-4-yl)ethyl]piperazine trihydrochloride Prepared from 4-[2-(1-tert-butyloxycarbonylpiperidin-4-yl)ethyl]-1-(1-methoxycarbonylmethylpiperidin-4-yl)piperazine and methanolic hydrochloric acid.

Yield: 93% of theory,
Melting point: 294–297° C. (dec.)
Mass spectrum: M$^+$=352
R$_f$: 0.20 (silica gel; methylene chloride/methanol/conc. ammonia=4:1:0.25)

(21) 1-[1-(2-Methoxycarbonylethyl)piperidin-4-yl]-4-[2-(piperidin-4-yl)ethyl]piperazine trihydrochloride Prepared from 4-[2-(1-tert-butyloxycarbonylpiperidin-4-yl)ethyl]-1-[1-(2-methoxycarbonylethyl)piperidin-4-yl]piperazine and methanolic hydrochloric acid.

Yield: 97% of theory,
Melting point: 324–326° C. (dec.)
Mass spectrum: M$^+$=366
R$_f$: 0.37 (silica gel; methylene chloride/methanol/conc. ammonia=9:1:0.25)

(22) trans-[1-(4-Methoxycarbonylmethyl-oxyphenyl)-4-[(piperidin-4-yl)methyloxy]cyclohexane hydrochloride Prepared from trans-4-[(1-tert-butyloxycarbonyl-piperidin-4-yl)methyloxy]-1-(4-methoxycarbonylmethyl-oxyphenyl)cyclohexane and ethereal hydrochloric acid.

Yield: 86% of theory,
Melting point: 198–200° C. (dec.)
Mass spectrum: M$^+$=361
R$_f$: 0.10 (silica gel; methylene chloride/methanol/conc. ammonia=9:1:0.1)

(23) trans-1-(4-Methoxycarbonylmethyloxyphenyl)-4-[(piperidin-4-yl)-N-acetylmethylamino]cyclohexane hydrochloride Prepared from trans-[1-(4-tert-butyloxycarbonylmethyloxyphenyl)-4-[(1-tert-butyloxycarbonylpiperidin-4-yl)-N-acetylmethylamino]cyclohexane and ethereal hydrochloric acid.

Yield: quantitative,
Melting point: 90–92° C.
Mass spectrum: M$^+$=402
R$_f$: 0.50 (silica gel; methylene chloride/methanol/conc. ammonia=4:1:0.25)

(24) cis/trans-1-(4-Methoxycarbonylmethyl)piperazino)-4-[(piperidin-4-yl)methyloxy]cyclohexane trihydrochloride Prepared from cis/trans-4-[(1-tert-butyloxycarbonylpiperidin-4-yl)methyloxy]-1-(4-methoxycarbonylmethyl)piperazino]cyclohexane and methanolic hydrochloric acid.

Yield: 46% of theory,
Melting point: 218–228° C.
Mass spectrum: M$^+$=353
R$_f$: 0.35 (silica gel; methylene chloride/methanol/conc. ammonia=4:1:0.2)

(25) cis/trans-1-[4-(2-Ethoxycarbonylethyl)piperazino]-4-[(piperidin-4-yl)methyloxy]cyclohexane trihydrochloride Prepared from cis/trans-4-[(1-tert-butyloxycarbonylpiperidin-4-yl)methyloxy]-1-[4-(2-ethoxycarbonylethyl)piperazino]cyclohexane and ethereal hydrochloric acid.

Yield: 98% of theory,
Melting point: 285–288° C.
Mass spectrum: M$^+$=381
R$_f$: 0.20 (silica gel; methylene chloride/methanol/conc. ammonia=4:1:0.2)

(26) cis/trans-1-[4-(1-Methoxycarbonylprop-2-yl)piperazino]-4-[(piperidin-4-yl)methyloxy]cyclohexane trihydrochloride Prepared from cis/trans-4-[(1-tert-butyloxycarbonylpiperidin-4-yl)methyloxy]-1-[4-(1-methoxycarbonylprop-2-yl)piperazino]cyclohexane and methanolic hydrochloric acid.

Yield: 90% of theory,
Melting point: 281–285° C.
Mass spectrum: M$^+$=381
R$_f$: 0.33 (silica gel; methylene chloride/methanol/conc. ammonia=9:1:0.1)

(27) 1-[4-(1-Methoxycarbonylethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(1-methoxycarbonylethyloxy)phenyl]piperazine and ethereal hydrochloric acid.

Yield: 80% of theory,
Melting point: 265–270° C.
Mass spectrum: M$^+$=375
R$_f$: 0.25 (silica gel; methylene chloride/methanol/conc. ammonia=4:1:0.2)

(28) 1-[4-(2-Ethoxycarbonylprop-2-yloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(2-ethoxycarbonylprop-2-yloxy)phenyl]piperazine and ethereal hydrochloric acid.

Yield: 76% of theory,
Melting point: 260–266° C.
Mass spectrum: M$^+$=403
R$_f$: 0.35 (silica gel; methylene chloride/methanol/conc. ammonia=2:1:0.2)

(29) 1-[4-(1-Methoxycarbonylbenzyl)phenyl]-4-[2-[piperidin-4-yl)ethyl]piperazine dihydrochloride Prepared from 4-[2-(1-tert-butyloxycarbonylpiperidin-4-yl)ethyl]-1-[4-(1-methoxycarbonylbenzyl)phenyl]piperazine and ethereal hydrochloric acid.

Yield: 76% of theory,
Melting point: 224–228° C.
Mass spectrum: (M+H)$^+$=438
R$_f$: 0.27 (silica gel; methylene chloride/methanol/conc. ammonia=4:1:0.2)

(30) 1-(4-Methoxycarbonylmethyloxyphenyl)-4-[(piperidin-4-yl)methylamino]piperidine dihydrochloride Prepared from 4-[(1-tert-butyloxycarbonylpiperidin-4-yl)methylamino]-1-(4-methoxycarbonylmethyloxyphenyl)piperidine and ethereal hydrochloric acid.

(31) 1-(4-Methoxycarbonylmethyloxyphenyl)-4-[(piperidin-4-yl)-N-methylmethylamino]piperidine dihydrochloride Prepared from 4-[(1-tert-butyloxycarbonylpiperidin-4-yl)-N-methylmethylamino]-1-(4-methoxycarbonylmethyloxyphenyl)piperidine and ethereal hydrochloric acid.

(32) 1-(4-Methoxycarbonylmethyloxyphenyl)-4-[(piperidin-4-yl)-N-benzylmethylamino]piperidine dihydrochloride Prepared from 4-[(1-tert-butyloxycarbonylpiperidin-4-yl)-N-benzylmethylamino]-1-(4-methoxycarbonylmethyloxyphenyl)piperidine and ethereal hydrochloric acid.

(33) 1-(4-Methoxycarbonylmethyloxyphenyl)-4-[(piperidin-4-yl)aminomethyl]piperidine dihydrochloride Prepared from 4-[(1-tert-butyloxycarbonylpiperidin-4-yl)aminomethyl]-1-(4-methoxycarbonylmethyloxyphenyl)piperidine and ethereal hydrochloric acid.

(34) 1-(4-Methoxycarbonylmethyloxyphenyl)-4-[(piperidin-4-yl)-N-benzylaminomethyl]piperidine dihydrochloride Prepared from 4-[(1-tert-butyloxycarbonylpiperidin-4-yl)-N-benzylaminomethyl]-1-(4-methoxycarbonylmethyloxyphenyl)piperidine and ethereal hydrochloric acid.

(35) 4-(4-Methoxycarbonylmethyloxyphenyl)-1-[2-(piperidin-4-yl)ethyl]piperidine dihydrochloride Prepared from 1-[2-(1-tert-butyloxycarbonylpiperidin-4-yl)ethyl]-4-(4-methoxycarbonylmethyloxyphenyl)piperidine and ethereal hydrochloric acid.

(36) 1-[4-(1,2-Dimethoxycarbonylethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(1,2-dimethoxycarbonylethyloxy)phenyl]piperazine and trifluoroacetic acid.

(37) 1-[4-(1-Methoxycarbonyl-2-phenylethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(1-methoxycarbonyl-2-phenylethyloxy)phenyl]piperazine and trifluoroacetic acid.

(38) 1-[4-(2-(4-Chlorophenyl)-1-methoxycarbonylethyloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(2-(4-chlorophenyl)-1-methoxycarbonylethyloxy)phenyl]piperazine and ethereal hydrochloric acid.

(39) 1-(4-Ethoxycarbonylmethyloxyphenyl)-4-[2-(piperidin-4-yl)ethyl]piperazin-3-one hydrochloride Prepared from 4-[2-(1-tert-butyloxycarbonylpiperidin-4-yl)ethyl]-1-(4-ethoxycarbonylmethyloxyphenyl)piperazin-3-one and ethereal hydrochloric acid.

(40) 1-(4-Ethoxycarbonylmethyloxyphenyl)-4-[2-(piperidin-4-yl)ethyl]piperazin-2,5-dione hydrochloride Prepared from 4-[2-(1-tert-butyloxycarbonylpiperidin-4-yl)ethyl]-1-(4-ethoxycarbonylmethyloxyphenyl)piperazin-2,5-dione and ethereal hydrochloric acid.

(41) 1-[4-(N-Acetyl-N-methoxycarbonylmethylamino)phenyl]-4-[2-(piperidin-4-yl)ethyl]piperazine dihydrochloride Prepared from 1-[4-(N-acetyl-N-methoxycarbonylmethylamino)phenyl]-4-[2-(1-tert-butyloxycarbonylpiperidin-4-yl)ethyl]piperazine.

Yield: 99.1% of theory,
Melting point: 198–199° C.
Mass spectrum: $M^+=402$
$R_f$: 0.25 (silica gel; methylene chloride/methanol/conc. ammonia=4:1:0.2)

(42) 1-[4-(N-n-Butylsulphonyl-N-methoxycarbonylmethylamino)phenyl]-4-[2-(piperidin-4-yl)ethyl]piperazine dihydrochloride Prepared from 4-[2-(1-tert-butyloxycarbonylpiperidin-4-yl)ethyl]-1-[4-(N-n-butylsulphonyl-N-methoxycarbonylmethylamino)phenyl]piperazine.

Yield: 85.2% of theory,
Melting point: 194–196° C.
Mass spectrum: $M^+=480$
$R_f$: 0.27 (silica gel; methylene chloride/methanol/conc. ammonia=4:1:0.2)

EXAMPLE 3

4-[2-(1-tert-Butyloxycarbonylpiperidin-4-yl)ethyl]-1-(4-methoxycarbonylmethyloxyphenyl)piperazine A solution of 4.8 g (0.01 mol) of 1-(4-methoxycarbonylmethyloxyphenyl)piperazine trifluoroacetate, 3.0 g (0.01 mol) of 1-[(1-tert-butyloxycarbonyl)piperidin-4-yl]-2-methanesulphonyloxyethane and 3.9 g=5.2 ml (0.03 mol) of N-ethyldiisopropylamine in 100 ml of methanol is heated at reflux temperature for 24 hours. The methanol is then distilled off in vacuo. The residue which remains is purified by chromatography on a silica gel column, methylene chloride which contains 3% methanol being used as eluent.

Yield: 2.1 g (46.6% of theory),
Melting point: 197–199° C.
Mass spectrum: $M^+=461$
$R_f$: 0.55 (silica gel; methylene chloride/methanol=9:1)

The following compounds can be prepared analogously to Example 3:

(1) 4-[2-(1-tert-Butyloxycarbonylpiperidin-4-yl)ethyl]-1-(4-ethoxycarbonylmethyloxyphenyl)piperazin-2-one Prepared from 1-(4-ethoxycarbonylmethyloxyphenyl)piperazin-2-one hydrochloride and 1-[(1-tert-butyloxycarbonyl)piperidin-4-yl]-2-methanesulphonyloxyethane.

Yield: 48% of theory,
Melting point: 94–96° C.
$R_f$: 0.65 (silica gel; methylene chloride/methanol=9:1)

(2) 4-[2-(1-tert-Butyloxycarbonylpiperidin-4-yl)ethyl]-1-[4-(2-methoxycarbonylethyl)phenyl]piperazine Prepared from 1-[4-(2-methoxycarbonylethyl)phenyl]piperazine and 1-[(1-tert-butyloxycarbonyl)piperidin-4-yl]-2-methanesulphonyloxyethane.

Yield: 56% of theory,
Melting point: 92–94° C.
$R_f$: 0.75 (silica gel; methylene chloride/methanol/conc. ammonia=9:1:0.1)

(3) 4-[2-(1-tert-Butyloxycarbonylpiperidin-4-yl)ethyl]-1-[3,4-di(methoxycarbonylmethyloxy)phenyl]piperazine Prepared from 1-[3,4-di(methoxycarbonylmethyloxy)phenyl]-piperazine and 1-[(1-tert-butyloxycarbonyl)piperidin-4-yl]-2-methanesulphonyloxyethane.

Yield: 30% of theory, of resin
Mass spectrum: $M^+=549$
$R_f$: 0.70 (silica gel; methylene chloride/methanol/conc. ammonia=9:1:0.1)

(4) 4-[2-(1-tert-Butyloxycarbonylpiperidin-4-yl)ethyl]-1-[4-methoxycarbonylmethyloxyphenyl)-2-methylpiperazine Prepared from 1-(4-methoxycarbonylmethyloxyphenyl)-2-methylpiperazine trifluoroacetate and 1-[(1-tert-butyloxycarbonyl)piperidin-4-yl]-2-methanesulphonyloxyethane.

Yield: 70% of theory, of oil

Mass spectrum: M⁺=475

R$_f$: 0.55 (silica gel; methylene chloride/methanol=9:1)

(5) (S)-4-[2-(1-tert-Butyloxycarbonylpiperidin-4-yl)
ethyl]-1-(4-ethoxycarbonylmethyloxyphenyl)-3-(4-
methoxybenzyl)piperazin-2-one Prepared from (S)-1-(4-ethoxycarbonylmethyl-oxyphenyl)-3-(4-methoxybenzyl)piperazin-2-one and 1-[(1-tert-butyloxycarbonyl)piperidin-4-yl]-2-methanesulphonyloxyethane.

Yield: 42% of theory, amorphous solid

Mass spectrum: M⁺=609

R$_f$: 0.25 (silica gel; ethyl acetate/cyclohexane=1:1)

(6) 4-[2-(1-tert-Butyloxycarbonylpiperidin-4-yl)
ethyl]-1-[2,4-di(ethoxycarbonylmethyloxy)phenyl]
piperazine Prepared from 1-[2,4-di(ethoxycarbonylmethyloxy)phenyl]piperazine and 1-[(1-tert-butyloxycarbonyl)piperidin-4-yl]-2-methanesulphonyloxyethane.

(7) 4-[2-(1-tert-Butyloxycarbonylpiperidin-4-yl)
ethyl]-1-[3,5-di(ethoxycarbonylmethyloxy)phenyl]
piperazine Prepared from 1-[3,5-di(ethoxycarbonylmethyloxy)phenyl]piperazine and 1-[(1-tert-butyloxycarbonyl)piperidin-4-yl]-2-methanesulphonyloxyethane.

(8) 4-[2-(1-tert-Butyloxycarbonylpiperidin-4-yl)
ethyl]-1-(3-ethoxycarbonylmethyloxyphenyl)
piperazine Prepared from 1-(3-ethoxycarbonylmethyloxyphenyl)piperazine and 1-[(1-tert-butyloxycarbonyl)piperidin-4-yl]-2-methanesulphonyloxyethane.

Yield: 29% of theory,

Melting point: 80–82° C.

Mass spectrum: M⁺=475

R$_f$: 0.50 (silica gel; methylene chloride/methanol 9:1)

(9) 4-[2-(1-tert-Butyloxycarbonylpiperidin-4-yl)
ethyl]-1-(4-ethoxycarbonylmethylaminophenyl)
piperazine Prepared from 1-(4-ethoxycarbonylmethylaminophenyl)piperazine and 1-[(1-tert-butyloxycarbonyl)piperidin-4-yl]-2-methanesulphonyloxyethane.

(10) (S)-1-[2-(1-tert-Butyloxycarbonylpiperidin-4-
yl)ethyl]-4-[1-(2-ethoxycarbonylethyl)-3-
isopropyloxycarbonylmethyl-2-oxopiperazinyl]
piperidine Prepared from (S)-4-[1-(2-ethoxycarbonylethyl)-3-isopropyloxycarbonylmethyl-2-oxopiperazinyl]piperidine and 1-[(1-tert-butyloxycarbonyl)piperidin-4-yl]-2-methanesulphonyloxyethane.

Yield: 26% of theory, amorphous solid

Mass spectrum: M⁺=594

R$_f$: 0.50 (silica gel; methylene chloride/methanol=9:1)

(11) 4-[2-(1-tert-Butyloxycarbonylpiperidin-4-yl)
ethyl]-1-(trans-4-methoxycarbonylmethyl-
oxycyclohexyl)piperazin-2-one Prepared from 1-(trans-4-methoxycarbonylmethyl-oxycyclohexyl)piperazin-2-one and 1-[(1-tert-butyloxycarbonyl)piperidin-4-yl]-2-methanesulphonyl-oxyethane.

Yield: 71% of theory,

Mass spectrum: M⁺=481

Melting point: 85–87° C.

R$_f$: 0.65 (silica gel; methylene chloride/methanol/conc. ammonia=9:1:0.1)

(12) 1-[4-(N-Acetyl-N-
methoxycarbonylmethylamino)phenyl]-4-[2-(1-tert-
butyloxycarbonylpiperidin-4-yl)ethyl]piperazine Prepared from 1-[4-(N-acetyl-N-methoxycarbonyl-methylamino)phenyl]piperazine hydrochloride and 1-[(1-tert-butyloxycarbonyl)piperidin-4-yl]-2-methanesulphonyloxyethane.

Yield: 34.8% of theory, of oil

Mass spectrum: M⁺=502

R$_f$: 0.6 (silica gel; methylene chloride/methanol=9:1)

(13) 4-[2-(1-tert-Butyloxycarbonylpiperidin-4-yl)
ethyl]-1-[4-(N-n-butylsulphonyl-N-
methoxycarbonylmethylamino)phenyl]piperazine Prepared from 1-[4-(N-n-butylsulphonyl-N-methoxycarbonylmethylamino)phenyl]piperazine hydro-chloride and 1-[(1-tert-butyloxycarbonyl)piperidin-4-yl]-2-methanesulphonyloxyethane.

Yield: 69.9% of theory, of oil

Mass spectrum: M⁺=580

R$_f$: 0.77 (silica gel; methylene chloride/methanol=9:1)

EXAMPLE 4

4-[(1-tert-Butyloxycarbonylpiperidin-4-yl)acetyl]-1-
(4-methoxycarbonylmethyloxyphenyl)piperazine A mixture of 1.5 g (0.062 mol) of 1-tert-butyloxycarbonylpiperidin-4-ylacetic acid, 2.94 g (0.0062 mol) of 1-(4-methoxycarbonylmethyloxyphenyl)piperazine trifluoroacetate, 1.9 g=2.6 ml (0.0185 mol) of triethylamine and 2.0 g (0.0062 mol) of 2-(1H-benzotriazol-1-yl)-1,1,3,3-tetramethyluronium tetrafluoroborate in 100 ml of dry dimethylformamide is stirred at room temperature overnight. It is then concentrated to dryness in vacuo and the residue which remains is partitioned between saturated, aqueous sodium hydrogen carbonate solution and ethyl acetate and the aqueous phase is extracted twice more with ethyl acetate. The combined organic extracts are dried and concentrated to dryness in vacuo. The residue is purified by means of chromatography on a silica gel column, methylene chloride which contains 3% methanol being used as eluent.

Yield: 1.3 g (44% of theory), amorphous solid

R$_f$: 0.40 (silica gel; methylene chloride/methanol=9:1)

The following compounds can be prepared analogously to Example 4:

(1) 4-[4-(1-Benzylpiperazinyl)acetyl]-1-(4-
methoxycarbonyl methyloxyphenyl)piperazine Prepared from 1-(4-methoxycarbonylmethyloxyphenyl) piperazine trifluoroacetate and 1-benzyl-4-carboxymethylpiperazine.

Yield: 45% of theory,

Melting point: 128–130° C.

Mass spectrum: M⁺=466

R$_f$: 0.75 (silica gel; methylene chloride/methanol/conc. ammonia=9:1:0.1)

(2) 4-[4-(1-Benzylpiperazinyl)carbonylmethyl]-1-(4-methoxycarbonylmethyloxyphenyl)piperazine Prepared from 4-carboxymethyl-1-(4-methoxycarbonylmethyloxyphenyl)piperazine and 1-benzylpiperazine.

Yield: 81% of theory,

Melting point: 95–96° C.

Mass spectrum: $M^+=466$ $R_f$: 0.40 (silica gel; methylene chloride/methanol=9:1)

EXAMPLE 5

1-(4-Methoxycarbonylmethyloxyphenyl)-4-[(piperidin-4-yl)aminocarbonyl]piperazine hydrochloride 2.0 g (4.3 mmol) of 4-[(1-benzylpiperidin-4-yl)aminocarbonyl]-1-(4-methoxycarbonylmethyloxyphenyl)piperazine are exhaustively hydrogenated at room temperature and under a hydrogen pressure of 50 psi over 0.5 g of palladium on carbon (10% strength) in 50 ml of methanol in the presence of 4.3 ml of 1N hydrochloric acid. The catalyst is filtered off, the filtrate is concentrated to dryness in vacuo and the residue is triturated with ether and filtered off with suction.

Yield: 1.5 g (84.8% of theory),

Melting point: 90–92° C.

Mass spectrum: $M^+=376$ $R_f$: 0.20 (silica gel; methylene chloride/methanol/conc. ammonia=4:1:0.2)

The following compounds can be prepared analogously to Example 5:

(1) 1-(4-Methoxycarbonylmethyloxyphenyl)-4-[(4-piperazinyl)acetyl]piperazine dihydrochloride Prepared from 4-[4-(1-benzylpiperazinyl)acetyl]-1-(4-methoxycarbonylmethyloxyphenyl)piperazine.

Yield: 96% of theory,

Melting point: 70–72° C.

Mass spectrum: $M^+=376$ $R_f$: 0.50 (silica gel; methylene chloride/methanol/conc. ammonia=4:1:0.2)

(2) 1-(4-Methoxycarbonylmethyloxyphenyl)-4-[(4-piperazinyl)carbonylmethyl]piperazine dihydrochloride Prepared from 4-[4-(1-benzylpiperazinyl)carbonylmethyl]-1-(4-methoxycarbonylmethyloxyphenyl)piperazine.

Yield: 96% of theory,

Melting point: 53–58° C.

Mass spectrum: $M^+=376$ $R_f$: 0.10 (silica gel; methylene chloride/methanol/conc. ammonia=9:1:0.1)

(3) 1-(4-tert-Butyloxycarbonylmethyloxyphenyl)-4-[(piperidin-4-yl)oxycarbonyl]piperazine Prepared from 4-[(1-benzylpiperidin-4-yl)oxycarbonyl]-1-(4-tert-butyloxycarbonylmethyloxyphenyl)piperazine.

EXAMPLE 6

4-[(1-Benzylpiperidin-4-yl)aminocarbonyl]-1-(4-methoxycarbonylmethyloxyphenyl)piperazine 1.5 g (0.008 mol) of 1-benzyl-4-aminopiperidine are added at 0° C. to a solution of 1.3 g (0.008 mol) of 1,1'-carbonyldi-(1,2,4-triazole) in 100 ml of dry dimethylformamide and the mixture is stirred for 30 minutes at 0° C. and for 1 hour at room temperature. 3.8 g (0.008 mol) of 1-(4-methoxycarbonylmethyloxyphenyl)piperazine trifluoroacetate and 2.4 g=3.3 ml (0.024 mol) of triethylamine are then added, and the mixture is heated for 2 hours at 80° C. and stirred for a further 16 hours at room temperature. The solution is concentrated to dryness in vacuo and the residue is partitioned between saturated sodium hydrogen carbonate solution and methylene chloride. The aqueous phase is extracted twice more with methylene chloride. The combined organic phases are dried and concentrated to dryness in vacuo. The residue is purified by chromatography on a silica gel column, methylene chloride which contains 3% methanol being used as eluent.

Yield: 2.0 g (54% of theory),

Melting point: 140–141° C.

Mass spectrum: $M^+=466$ $R_f$: 0.40 (silica gel; methylene chloride/methanol=9:1)

EXAMPLE 7

1-(4-Carboxymethyloxyphenyl)-4-[(4-piperazinyl)acetyl]piperazine 5.3 ml of a 1N sodium hydroxide solution are added to a solution of 0.6 g (1.3 mmol) of 1-(4-methoxycarbonylmethyloxyphenyl)-4-[(4-piperazinyl)acetyl]piperazine dihydrochloride in 8 ml of tetrahydrofuran and 4 ml of water, and the mixture is allowed to stand at room temperature for 3 hours. After this time, 5.3 ml of 1N hydrochloric acid are added and the solution is concentrated to dryness in vacuo. The residue is treated three times with acetone and concentrated to dryness each time. The residue which remains is stirred with a mixture of methylene chloride/methanol=1:1. The precipitated inorganic salts are filtered off with suction. The mother liquor is concentrated to dryness in vacuo.

Yield: 52% of theory, amorphous foam

Mass spectrum: $(M+H)^+=363$ $R_f$: 0.22 (silica gel; methylene chloride/methanol/conc. ammonia=2:1:0.25)

The following compounds can be prepared analogously to Example 7:

(1) 1-(trans-4-Carboxymethyloxycyclohexyl)-4-[2-(piperidin-4-yl)ethyl]piperazin-2-one Prepared from 1-(trans-4-methoxycarbonylmethyloxycyclohexyl)-4-[2-(piperidin-4-yl)ethyl]piperazin-2-one dihydrochloride.

Yield: quantitative,

Melting point: 305–307° C. (dec.)

Mass spectrum: $(M+H)^+=368$ $R_f$: 0.15 (silica gel; methylene chloride/methanol/conc. ammonia=2:1:0.25)

(2) 1-(1-Carboxymethylpiperidin-4-yl)-4-[2-(piperidin-4-yl)ethyl]piperazine

Prepared from 1-(1-methoxycarbonylmethylpiperidin-4-yl)-4-[2-(piperidin-4-yl)ethyl]piperazine trihydrochoride.

Yield: quantitative,

Melting point: 262–264° C. (dec.)

Mass spectrum: $(M+H)^+=339$ $R_f$: 0.065 (silica gel; methylene chloride/methanol/conc. ammonia=2:1:0.25)

(3) cis/trans-1-[4-(2-Carboxyethyl)piperazino]-4-[(piperidin-4-yl)methyloxy]cyclohexane trihydrochloride Prepared from cis/trans-1-[4-(2-ethoxycarbonylethyl)piperazino]-4-[(4-piperidin-4-yl)methyloxy]cyclohexane trihydrochloride and lithium hydroxide.

Yield: 58% of theory,
Melting point: 248–256° C.
Mass spectrum: $(M+H)^+=354$
$R_f$: 0.16 (silica gel; methylene chloride/methanol/conc. ammonia=2:1:0.2)

(4) 1-[4-(1-Carboxyethyloxy)phenyl]-4-[2-(piperidin-4-yl)ethyl]piperazine

Prepared from 1-[4-(1-methoxycarbonylethyloxy)phenyl]-4-[2-(piperidin-4-yl)ethyl]piperazine dihydrochloride and lithium hydroxide.

Yield: 79% of theory,
Melting point: 278–288° C.
Mass spectrum: $M^+=361$
$R_f$: 0.17 (silica gel; methylene chloride/methanol/conc. ammonia=2:1:0.2)

(5) 1-[4-(2-Carboxyprop-2-yloxy)phenyl]-4-[2-(piperidin-4-yl)ethyl]piperazine

Prepared from 1-[4-(2-ethoxycarbonylprop-2-yloxy)phenyl]-4-[2-(piperidin-4-yl)ethyl]piperazine dihydrochloride and lithium hydroxide.

Yield: 61% of theory,
Melting point: 262–265° C.
Mass spectrum: $M^+=375$
$R_f$: 0.30 (silica gel; methylene chloride/methanol/conc. ammonia=1:1:0.2)

(6) 1-[4-(1-Carboxybenzyloxy)phenyl]-4-[2-(piperidin-4-yl)ethyl]piperazine dihydrochloride Prepared from 1-[4-(1-methoxycarbonylbenzyloxy)phenyl]-4-[2-(piperidin-4-yl)ethyl]piperazine dihydrochloride and lithium hydroxide.

Yield: 89% of theory,
Melting point: >250° C.
Mass spectrum: $M^+=423$
$R_f$: 0.12 (silica gel; methylene chloride/methanol/conc. ammonia=2:1:0.2)

EXAMPLE 8

4-[2-(1-tert-Butyloxycarbonylpiperazin-4-yl)ethyl]-1-(4-methoxycarbonylmethyloxyphenyl)piperazine A solution of 1.63 g (3.4 mmol) of 1-(4-methoxycarbonylmethyloxyphenyl)piperazine trifluoroacetate, 1.0 g (3.4 mmol) of 2-(1-tert-butyloxycarbonylpiperazin-4-yl)ethyl bromide and 1.32 g=1.8 ml (10.2 mmol) of N-ethyldiisopropylamine in 5 ml of methanol is allowed to stand at room temperature for 24 hours. The methanol is distilled off in vacuo and the residue is purified by means of chromatography on a silica gel column, methylene chloride/methanol/conc. ammonia=99:1:0.1 being used as eluent.

Yield: 1.6 g (quantitative) of oil,
Mass spectrum: $M^+=462$
$R_f$: 0.55 (silica gel; methylene chloride/methanol/conc. ammonia=9:1:0.1)

The following compound can be prepared analogously to Example 8:

(1) 4-[2-(1-tert-Butyloxycarbonylpiperazin-4-yl)ethyl]-1-(4-methoxycarbonylmethylphenyl)piperazine Prepared from 1-(4-methoxycarbonylmethylphenyl)piperazine hydrochloride and 2-(1-tert-butyloxycarbonylpiperazin-4-yl)ethyl bromide.

Yield: 45% of theory,
Melting point: 161–180° C. (dec.)
Mass spectrum: $M^+=446$
$R_f$: 0.37 (silica gel; methylene chloride/methanol/conc. ammonia=9:1:0.1)

EXAMPLE 9

1-[3,4-Di(ethoxycarbonylmethyloxy) phenyl]-4-[2-(piperidin-4-yl)ethyl]piperazine dihydrochloride Hydrogen chloride is passed into a suspension of 200 mg (0.405 mmol) of 1-[3,4-di(carboxymethyloxy)phenyl]-4-[2-(piperidin-4-yl)ethyl]piperidine dihydrochioride in 50 ml of absolute ethanol with stirring and cooling with ice until it is saturated, a clear solution resulting. This solution is allowed to stand at room temperature overnight and is then concentrated to dryness in vacuo. The residue is triturated with acetone and filtered off with suction.

Yield: 0.2 g (83% of theory),
Melting point: 161–163° C. (dec.)
Mass spectrum: $M^+=477$
$R_f$: 0.35 (silica gel; methylene chloride/methanol/conc. ammonia=4:1:0.2)

The following compounds can be prepared analogously to Example 9:

(1) 1-[3,4-Di(isobutyloxycarbonylmethyloxy) phenyl]-4-[2-piperidin-4-yl)ethyl]piperazine dihydrochloride Prepared from 1-[3,4-di(carboxymethyloxy)phenyl]-4-[2-(piperidin-4-yl)ethyl]piperazine dihydrochloride and isobutanol.

Melting point: 156–158° C. (dec.)
Mass spectrum: $M^+=533$
$R_f$: 0.50 (silica gel; methylene chloride/methanol/conc. ammonia=4:1:0.2)

(2) 1-[3,4-Di(cyclohexyloxycarbonylmethyloxy) phenyl]4-[2-(piperidin-4-yl)ethyl]piperazine dihydrochloride Prepared from 1-[3,4-di(carboxymethyloxy)phenyl]-4-[2-(piperidin-4-yl)ethyl]piperazine dihydrochloride and cyclohexanol.

Melting point: 148–152° C.
Mass spectrum: $M^+=585$
$R_f$: 0.50 (silica gel; methylene chloride/methanol/conc. ammonia=4:1:0.2)

(3) 1-[3,4-Di[(cyclopentyloxycarbonylmethyloxy) phenyl]-4-[2-(piperidin-4-yl)ethyl]piperazine dihydrochloride Prepared from 1-[3,4-di[(carboxymethyloxy)phenyl]-4-[2-(piperidin-4-yl)ethyl]piperazine dihydrochloride and cyclopentanol.

Melting point: 88–90° C.

Mass spectrum: M⁺=557

$R_f$: 0.5 (silica gel; methylene chloride/methanol/conc. ammonia=2:1:0.25)

EXAMPLE 10

1-(4-Isobutyloxycarbonylmethyloxyphenyl)-4-[2-(piperidin-4-yl)ethyl]piperazine 20 ml of ethereal hydrochloric acid are added to a suspension of 0.6 g (1.4 mmol) of 1-(4-carboxymethyloxyphenyl)-4-[2-(piperidin-4-yl)ethyl]piperazine dihydrochloride in 30 ml of isobutanol and the ether is distilled off at 50° C. The mixture is then heated for 12 hours at 130° C. The solution resulting in this way is cooled and diluted with ether. The precipitated solid is filtered off with suction and purified by means of chromatography on a silica gel column, methylene chloride/methanol/conc. ammonia=4:1:0.2 being used as eluent.

Yield: 250 mg (43.4% of theory),

Melting point: 137–139° C.

Mass spectrum: M⁺=403

$R_f$: 0.30 (silica gel; methylene chloride/methanol/conc. ammonia=4:1:0.2)

The following compounds can be prepared analogously to Example 10:

(1) 1-(4-Cyclohexyloxycarbonylmethyloxyphenyl)-4-[2-(piperidin-4-yl)ethyl]piperazine dihydrochloride Prepared from 1-(4-carboxymethyloxyphenyl)-4-[2-(piperidin-4-yl)ethyl]piperazine dihydrochloride and cyclohexanol at 180° C.

Yield: 42% of theory,

Melting point: 248–250° C.

Mass spectrum: M⁺=429

$R_f$: 0.40 (reversed-phase plate RP 18; methanol/50% strength sodium chloride solution=3:2)

(2) 1-(4-Cyclopentyloxycarbonylmethyloxyphenyl)-4-[2-(piperidin-4-yl)ethyl]piperazine dihydrochloride Prepared from 1-(4-carboxymethyloxyphenyl)-4-[2-(piperidin-4-yl)ethyl]piperazine dihydrochloride and cyclopentanol.

(3) 1-(4-n-Butyloxycarbonylmethyloxyphenyl)-4-[2-(piperidin-4-yl)ethyl]piperazine dihydrochloride Prepared from 1-(4-carboxymethyloxyphenyl)-4-[2-(piperidin-4-yl)ethyl]piperazine dihydrochloride and n-butanol.

(4) 1-(4-Cycloheptyloxycarbonylmethyloxyphenyl)-4-[2-(piperidin-4-yl)ethyl]piperazine dihydrochloride Prepared from 1-(4-carboxymethyloxyphenyl)-4-[2-(piperidin-4-yl)ethyl]piperazine dihydrochloride and cycloheptanol.

(5) 1-(4-Cyclohexyloxycarbonylmethyloxyphenyl)-2-methyl-4-[2-(piperidin-4-yl)ethyl]piperazine dihydrochloride Prepared from 1-(4-carboxymethyloxyphenyl)-2-methyl-4-[2-piperidin-4-yl)ethyl]piperazine dihydrochloride and cyclohexanol.

Yield: 63% of theory, amorphous solid

Mass spectrum: M⁺=443

$R_f$: 0.27 (reversed-phase plate RP18; methanol/5% strength sodium chloride solution=3:2)

EXAMPLE 11 trans-1-(4-tert-Butyloxycarbonylmethyloxyphenyl)-4-[(1-tert-butyloxycarbonylpiperidin-4-yl)methylamino]cyclohexane 0.23 g (6.1 mmol) of sodium borohydride is added in portions at −18° C. with stirring to a solution of 8.85 g (15 mmol) of 1-(4-tert-butyloxycarbonylmethyloxyphenyl)-4-[(1-tert-butyloxycarbonylpiperidin-4-yl)methyleneimino]cyclohexane in 40 ml of dry methanol and the mixture is stirred for a further 2.5 hours at −15° C. and then for 1 day at room temperature. The solution is concentrated to dryness in vacuo, the residue is partitioned between water and ethyl acetate, and the organic phase is dried and evaporated to dryness in vacuo. The residue which remains is purified by means of chromatography on a silica gel column, methylene chloride/methanol/conc. ammonia=9:1:0.1 being used as eluent.

Yield: 3.88 g (44% of theory),

Melting point: 64–67° C.

Mass spectrum: M⁺=502

$R_f$: 0.47 (silica gel; methylene chloride/methanol/conc. ammonia=9:1:0.1)

EXAMPLE 12 trans-1-(4-tert-Butyloxycarbonylmethyloxyphenyl)-4-[(1-tert-butyloxycarbonylpiperidin-4-yl)-N-methylmethylamino]-cyclohexane 160 ml (2 mmol) of formalin solution (37% strength) and 135 mg (2 mmol) of sodium cyanoborohydride are added at room temperature and with stirring to a solution of 502 mg (1 mmol) of trans-1-(4-tert-butyloxycarbonylmethyloxyphenyl)-4-[(1-tert-butyloxycarbonylpiperidin-4-yl)methylamino]cyclohexane in 20 ml of methanol, and the mixture is stirred further for 1 hour and evaporated to dryness in vacuo. The residue is purified by means of chromatography on a silica gel column, methylene chloride/methanol/conc. ammonia=19:1:0.1 and 9:1:0.1 being used as eluent.

Yield: 370 mg (72% of theory), of oil

Mass spectrum: M⁺=516

$R_f$: 0.60 (silica gel; methylene chloride/methanol/conc. ammonia=9:1:0.1)

The following compounds can be prepared analogously to Example 12:

(1) 4-[2-(1-tert-Butyloxycarbonylpiperidin-4-yl)ethyl]-1-(trans-4-carboxymethyloxycyclohexyl)piperazine Prepared from 450 mg (2.6 mmol) of 4-carboxymethyloxycyclohexanone, 770 mg (2.6 mmol) of 1-[2-(1-tert-butyloxycarbonylpiperidin-4-yl)ethyl]piperazine, 0.15 ml (2.6 mmol) of acetic acid and 260 mg (3.9 mmol) of sodium cyanoborohydride in 30 ml of tetrahydrofuran.

Yield: 28% of theory, foam $R_f$: 0.22 (silica gel; methylene chloride/methanol/conc. ammonia=4:1:0.25)

(2) trans-1-(4-tert-Butyloxycarbonylmethyloxypiperidino)-4-[(1-tert-butyloxycarbonylpiperidin-4-yl)methyloxy]cyclohexane Prepared from 4-[(1-tert-butyloxycarbonylpiperidin-4-yl)methyloxy]cyclohexanone, 4-tert-butyloxycarbonylmethyloxypiperidine and sodium triacetoxyborohydride.

Yield: 9% of theory, $R_f$: 0.50 (silica gel; methylene chloride/methanol/conc. ammonia=9:1:0.1)

(3) cis/trans-4-[(1-tert-Butyloxycarbonylpiperidin-4-yl)methyloxy]-1-(4-methoxycarbonylmethylpiperazino)cyclohexane Prepared from 4-[(1-tert-butyloxycarbonylpiperidin-4-yl)methyloxy]cyclohexanone, 1-methyloxycarbonylmethylpiperazine and sodium triacetoxyborohydride.

Yield: 18% of theory, of oil $R_f$: 0.90 (silica gel; methylene chloride/methanol/conc. ammonia=2:1:0.2)

(4) cis/trans-4-[(1-tert-Butyloxycarbonylpiperidin-4-yl)methyloxy]-1-[4-(2-ethoxycarbonylethyl)piperazino]cyclohexane Prepared from 4-[(1-tert-butyloxycarbonylpiperidin-4-yl)methyloxy]cyclohexanone, 1-(2-ethoxycarbonylethyl)piperazine and sodium triacetoxyborohydride.

Yield: 85% of theory, of oil

Mass spectrum: $M^+=481$ $R_f$: 0.45 (silica gel; methylene chloride/methanol/conc. ammonia=9:1:0.1)

(5) cis/trans-4-([1-tert-Butyloxycarbonylpiperidin-4-yl)methyloxy]-1-[4-(1-methoxycarbonylprop-2-yl)piperazino]cyclohexane Prepared from 4-[(1-tert-butyloxycarbonylpiperidin-4-yl)methyloxy]cyclohexanone, 1-(1-methoxycarbonylprop-2-yl)piperazine and sodium cyanoborohydride.

Yield: 13% of theory,

Melting point: 70–72° C.

$R_f$: 0.50 (silica gel; methylene chloride/methanol/conc. ammonia=9:1:0.1)

EXAMPLE 13

4-[(1-tert-Butyloxycarbonylpiperidin-4-yl)methyloxy]-1-(4-methoxycarbonylmethyloxyphenyl)piperidine Prepared from 400 mg (1 mmol) of 4-[(1-tert-butyloxycarbonylpiperidin-4-yl)methyloxy]-1-(4-hydroxyphenyl)piperidine, 0.1 ml (1 mmol) of methyl bromoacetate and 166 mg (1.2 mmol) of potassium carbonate and 10 ml of dimethylformamide analogously to Example XIIIa.

Yield: 340 mg (72% of theory),

Melting point: 77–79° C.

Mass spectrum: $M^+=462$ $R_f$: 0.60 (silica gel; methylene chloride/methanol=15:1)

The following compounds can be prepared analogously to Example 13:

(1) 4-[2-(1-tert-Butyloxycarbonylpiperidin-4-yl)ethyl]-1-(1-methoxycarbonylmethylpiperidin-4-yl)piperazine Prepared from 4-[2-(1-tert-butyloxycarbonylpiperidin-4-yl)ethyl]-1-(piperidin-4-yl)piperazine and methyl bromoacetate.

Yield: 85% of theory,

Melting point: 71–74° C.

Mass spectrum: $M^+=452$ $R_f$: 0.50 (silica gel; methylene chloride/methanol/conc. ammonia=9:1:0.1)

(2) trans-4-[(1-tert-Butyloxycarbonylpiperidin-4-yl)methyloxy]-1-(4-methoxycarbonylmethyloxyphenyl)cyclohexane Prepared from trans-4-[(1-tert-butyloxycarbonylpiperidin-4-yl)methyloxy]-1-(4-hydroxyphenyl)cyclohexane and methyl bromoacetate.

Yield: 82% of theory,

Melting point: 70–72° C.

Mass spectrum: $M^+=461$ $R_f$: 0.55 (silica gel; methylene chloride/methanol=15:1)

(3) 4-[2-(1-tert-Butyloxycarbonylpiperidin-4-yl)ethyl]-1-[4-(1-methoxycarbonylethyloxy)phenyl]piperazine Prepared from 4-[2-(1-tert-butyloxycarbonylpiperidin-4-yl)ethyl]-1-(4-hydroxyphenyl)piperazine and methyl 2-bromopropionate.

Yield: 90% of theory, of oil $R_f$: 0.30 (silica gel; methylene chloride/methanol/conc. ammonia=2:1:0.1)

(4) 4-[2-(1-tert-Butyloxycarbonylpiperidin-4-yl)ethyl]-1-[4-(2-ethoxycarbonylpropyloxy)phenyl]piperazine Prepared from 4-[2-(1-tert-butyloxycarbonylpiperidin-4-yl)ethyl]-1-(4-hydroxyphenyl)piperazine and ethyl 2-bromoisobutyrate.

Yield: 47% of theory, of oil $R_f$: 0.60 (silica gel; methylene chloride/methanol/=20:1)

(5) 4-[2-(1-tert-Butyloxycarbonylpiperidin-4-yl)ethyl]-1-[4-(1-methoxycarbonylbenzyl)phenyl]piperazine Prepared from 4-[2-(1-tert-butyloxycarbonylpiperidin-4-yl)ethyl]-1-(4-hydroxyphenyl)piperazine and methyl α-bromophenylacetate.

Yield: 93% of theory, of oil $R_f$: 0.23 (silica gel; methylene chloride/methanol/conc. ammonia=20:1:0.1)

EXAMPLE 14

4-[2-(1-tert-Butyloxycarbonylpiperidin-4-yl)ethyl]-1-[1-(2-methoxycarbonylethyl)piperidin-4-yl]piperazine A solution of 730 mg (1.9 mmol) of 4-[2-(1-tert-butyloxycarbonylpiperidin-4-yl)ethyl]-1-(piperidin-4-yl)piperazine and 0.18 ml (2 mmol) of methyl acrylate in 10 ml of methanol is allowed to stand at room temperature overnight and is then concentrated to dryness in vacuo. The residue is purified by means of chromatography on a silica gel column, methylene chloride/methanol/conc. ammonia=19:1:0.1 being used as eluent.

Yield: 840 mg (94% of theory),

Melting point: 95–97° C.

$R_f$: 0.55 (silica gel; methylene chloride/methanol/conc. ammonia=9:1:0.1)

EXAMPLE 15 trans-[1-(4-tert-Butyloxycarbonylmethyloxyphenyl)-4-[(1-tert-butyloxycarbonylpiperidin-4-yl)-N-acetylmethylamino]cyclohexane A solution of 0.14 ml (2.0 mmol) of acetyl chloride in 5 ml of methylene chloride is added dropwise with stirring and at −10° C. to a solution of 740 mg (1.5 mmol) of trans-1-(4-tert-butyloxycarbonylmethyloxyphenyl)-4-[(1-tert-butyloxycarbonylpiperidin-4-yl)methylamino]cyclohexane and 0.3 ml (2.1 mmol) of triethylamine in 50 ml of methylene chloride and the mixture is allowed to stand at room temperature overnight. It is washed with water and the organic phase is concentrated to dryness in vacuo. The residue is purified by means of chromatography on a silica gel column, methylene chloride/methanol=30:1 being used as eluent.

Yield: 690 mg (86% of theory), of resin

Mass spectrum: $M^+$=544

$R_f$: 0.65 (silica gel; methylene chloride/methanol/conc. ammonia=9:1:0.1)

EXAMPLE 16

1-[4-(1-Methoxycarbonyl-3-hydroxypropyloxy)phenyl]-4-[2-(piperidin-4-yl)ethyl]piperazine dihydrochloride Prepared from 4-[2-(1-tert-butyloxycarbonylpiperidin-4-yl)ethyl]-1-[4-(2-oxotetrahydrofuran-3-yloxy)phenyl]piperazine and ethereal hydrochloric acid in methanol. The product is contaminated with the corresponding lactone.

Melting point: from 220° C. (dec.)

Mass spectrum: $(M+H)^+$=406

$R_f$: 0.22 (silica gel; methylene chloride/methanol/conc. ammonia=4:1:0.2)

EXAMPLE 17

Dry ampoule containing 2.5 mg of active compound per 1 ml

Composition

| Active compound | 2.5 mg |
|---|---|
| Mannitol | 50.0 mg |
| Water for injection purposes to | 1.0 ml |

Preparation

Active compound and mannitol are dissolved in water. After dispensing, the solution is freeze-dried. Dissolution to give the ready-to-use solution is carried out using water for injection purposes.

EXAMPLE 18

Dry ampoule containing 35 mg of active compound per 2 ml

Composition

| Active compound | 35.0 mg |
|---|---|
| Mannitol | 100.0 mg |
| Water for injection purposes to | 2.0 ml |

Preparation

Active compound and mannitol are dissolved in water. After dispensing, the solution is freeze-dried. Dissolution to give the ready-to-use solution is carried out using water for injection purposes.

EXAMPLE 19

Tablet containing 50 mg of active compound

Composition

| (1) Active compound | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed and granulated with an aqueous solution of (4). (5) is admixed to the dried granules. Tablets are pressed from this mixture which are biplanar with a bevel on both sides and a breaking notch on one side. Diameter of the tablets: 9 m.

EXAMPLE 20

Tablets containing 350 mg of active compound

Composition

| (1) Active compound | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed and granulated with an aqueous solution of (4). (5) is admixed to the dried granules. Tablets are pressed from this mixture which are biplanar with a bevel on both sides and a breaking notch on one side. Diameter of the tablets: 12 mm.

EXAMPLE 21

Capsules containing 50 mg of active compound

Composition

| (1) Active compound | 50.0 mg |
|---|---|
| (2) Maize starch, dry | 58.0 mg |
| (3) Lactose, powdered | 50.0 mg |
| (4) Magnesium stearate | 2.0 mg |
| | 160.0 mg |

Preparation (1) is triturated with (3). This trituration is added to the mixture of (2) and (4) with intensive mixing.

This powder mixture is dispensed into hard gelatin capsules of size 3 in a capsule dispensing machine.

EXAMPLE 22

Capsules containing 350 mg of active compound
Composition

| | | |
|---|---|---:|
| (1) | Active compound | 350.0 mg |
| (2) | Maize starch, dry | 46.0 mg |
| (3) | Lactose, powdered | 30.0 mg |
| (4) | Magnesium stearate | 4.0 mg |
| | | 430.0 mg |

Preparation (1) is triturated with (3). This trituration is added to the mixture of (2) and (4) with intensive mixing.

This powder mixture is dispensed into hard gelatin capsules of size 0 in a capsule dispensing machine.

What is claimed is:

1. A compound of the formula I

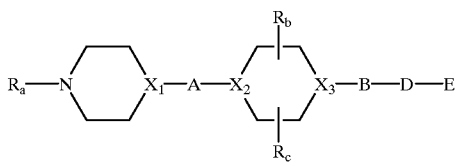

(I)

in which $R_a$ is a hydrogen atom, a $C_{1-5}$-alkyl or phenyl-$C_{1-3}$-alkyl group, in which in each case the alkyl moiety is optionally substituted by a carboxyl, $C_{1-3}$-alkoxycarbonyl, aminocarbonyl, N—$C_{1-3}$-alkylaminocarbonyl, N,N-di($C_{1-3}$-alkyl)aminocarbonyl, vinyl or ethynyl group or alternatively, if the abovementioned substituents are not on an α-carbon atom adjacent to a nitrogen atom, by a hydroxyl, $C_{1-3}$-alkoxy, amino, $C_{1-3}$-alkylamino or di($C_{1-3}$-alkyl)amino group, or is a radical which is cleaved in vivo, $R_b$ and $R_c$, which are identical or different, in each case are a hydrogen atom or the side chain of a natural D- or L-α-amino acid, or its ester or ether, A is an —$HCR_1$—$HCR_2$—, —CO—$HCR_1$—, —$HCR_1$—CO—, —$NR_3$—$HCR_1$—, —$HCR_1$—$NR_3$—, —$NR_2$—CO—, —CO—$NR_2$—, —O—CO—, —CO—O—, —O—$HCR_1$— or —$CHR_1$—O— group, in which $R_1$ is a hydrogen atom, a $C_{1-3}$-alkyl, phenyl-$C_{1-3}$-alkyl or phenyl group, $R_2$ is a hydrogen atom, a $C_{1-3}$-alkyl or phenyl-$C_{1-3}$-alkyl group and $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$ is a methine group, $X_2$ and $X_3$ are each a nitrogen atom, it additionally being optional in the above-mentioned heterocyclic rings in which $X_2$ and $X_3$ are each a nitrogen atom for a methylene group linked to a ring nitrogen atom to be replaced by a carbonyl group, B is a 3-piperidinylene, 4-piperidinylene or 1,4-piperazinylene group, in which in each case a methylene group adjacent to a nitrogen atom is optionally replaced by a carbonyl group, it additionally being optional for a 1,4-piperazinylene group to be substituted by $R_b$ and $R_c$, and $R_b$ and $R_c$ being defined as mentioned above, or a phenylene, cyclohexylene, pyridinylene, pyridazinylene, pyrimidinylene or pyrazinylene group, D is an —O—$R_1CR_4$—CO—, —$NR_3$—$HCR_1$—CO—, —$NR_3$—$CH_2CH_2CO$—, —$CH_2CO$—, —$CHR_1CH_2CO$— or (—O—$)_2$CH—CO— group, in which $R_1$ and $R_3$ are defined as mentioned above and $R_4$ is a hydrogen atom, a $C_{1-3}$-alkyl, hydroxy-$C_{1-3}$-alkyl, carboxy-$C_{1-3}$-alkyl, $C_{1-3}$-alkoxycarbonyl-$C_{1-3}$-alkyl, $C_{3-7}$-cycloalkoxycarbonyl-$C_{1-3}$-alkyl, phenyl-$C_{1-3}$-alkyl, phenyl, pyridyl-$C_{1-3}$-alkyl or pyridyl group, and E is a hydroxyl group, an alkoxy group having 1 to 6 carbon atoms, a phenylalkoxy group in which the alkoxy moiety contains 1 to 3 carbon atoms, a cycloalkoxy group having 3 to 9 carbon atoms in which the cycloalkyl moiety having 5 to 8 carbon atoms is optionally, additionally substituted by one or two alkyl groups each having 1 to 3 carbon atoms, a cycloalkoxy group having 5 to 8 carbon atoms in which in the cycloalkyl moiety a methylene group in the 3- or 4-position is replaced by an oxygen atom or by an imino group which is optionally substituted by an alkyl, phenylalkyl or phenylalkoxycarbonyl group, in which the alkyl and alkoxy moiety each contain 1 to 3 carbon atoms, or by an alkanoyl group having 2 to 6 carbon atoms, and the cycloalkyl moiety is optionally, additionally substituted by one or two alkyl groups each having 1 to 3 carbon atoms, or is a cycloalkenyloxy group in which the cycloalkenyl moiety contain 4 to 7 carbon atoms, an alkenyloxy, phenylalkenyloxy, alkynyloxy or phenylalkynyloxy group with the proviso that a bond to the oxygen atom does not start from a carbon atom which carries a double or triple bond and in which the alkenyl and alkynyl moiety each contain 3 to 5 carbon atoms, a cycloalkylalkoxy group in which the cycloalkyl moiety contains 3 to 8 carbon atoms and the alkoxy moiety 1 to 3 carbon atoms, a bicycloalkoxy group having a total of 8 to 10 carbon atoms, which in the bicycloalkyl moiety is optionally, additionally substituted by one or two alkyl groups each having 1 to 3 carbon atoms, a 1,3-dihydro-3-oxo-1-isobenzofuranyloxy group or an $R_7$—CO—O—($R_5CR_6$)—O group, in which $R_5$ is a hydrogen atom, a $C_{1-6}$-alkyl, $C_{3-7}$-cycloalkyl or phenyl group, $R_6$ is a hydrogen atom or a $C_{1-6}$-alkyl group and $R_7$ is a $C_{1-5}$-alkyl, $C_{1-5}$-alkoxy, $C_{5-7}$-cycloalkyl or $C_{5-7}$-cycloalkoxy group, or E is an α-amino group of a natural D- or L-amino acid or its ester, where the expressions "a phenyl group" or "a phenylene group" mentioned in the definition of the above radicals in each instance mean, respectively, either an unsubstituted phenyl or phenylene group or a phenyl or phenylene group which is mono-, di- or trisubstituted by fluorine, chlorine, bromine or iodine atoms, by $C_{1-3}$-alkyl, trifluoromethyl, nitro, amino, $C_{1-3}$-alkylamino, di($C_{1-3}$-alkyl)amino, $C_{1-4}$-alkanoylamino, hydroxyl, $C_{1-3}$-alkoxy, carboxyl, $C_{1-3}$-alkoxycarbonyl, $C_{3-7}$-cycloalkoxycarbonylalkoxy, hydroxycarbonyl-$C_{1-3}$-alkoxy, $C_{1-3}$-alkoxycarbonyl-$C_{1-3}$-alkoxy, aminocarbonyl, $C_{1-3}$-alkylaminocarbonyl or di($C_{1-3}$-alkyl)-aminocarbonyl groups, wherein, if there is more than one substituent, the substituents are identical or different, the esters of a natural α-amino acid are understood as meaning its $C_{1-6}$-alkyl, $C_{2-6}$-alkenyl, $C_{5-7}$-cycloalkyl, phenyl or phenyl-$C_{1-3}$-alkyl esters, the ethers of the side chain of a natural D- or L-α-amino acid are understood as meaning its $C_{1-5}$-alkyl, phenyl-$C_{1-3}$-alkyl, phenyl or $C_{4-7}$-cycloalkyl ether and a radical which is cleaved in vivo is understood as meaning an alkanoyl group having a total of 1 to 6 carbon atoms, a benzoyl, allyloxycarbonyl, $C_{1-5}$-alkoxycarbonyl or phenyl-$C_{1-3}$-alkoxycarbonyl group, or a tautomer or pharmaceutically acceptable salt thereof.

2. A compound of the formula I according to claim 1, in which $R_a$ is a hydrogen atom, a $C_{1-5}$-alkyl or phenyl-$C_{1-3}$-alkyl group in which in each case the alkyl moiety is optionally substituted by a carboxyl, $C_{1-3}$-alkoxycarbonyl, aminocarbonyl, N—$C_{1-3}$-alkylamino-carbonyl, N,N-di($C_{1-3}$-alkyl)aminocarbonyl, vinyl or ethynyl group or alternatively, if the abovementioned substituents are not on an α-carbon atom adjacent to a nitrogen atom, by a hydroxyl, $C_{1-3}$-alkoxy, amino, $C_{1-3}$-alkylamino or di($C_{1-3}$-alkyl)amino group, or is a radical which is cleaved in vivo, $R_b$ and $R_c$, which are identical or different, are each a hydrogen atom or the side chain of a natural D- or L-α-amino acid, or its ester or ether, A is an —$HCR_1$—$HCR_2$—, —CO—$HCR_1$—, —$HCR_1$—CO—, —$NR_3$—$HCR_1$—, —$HCR_1$—$NR_3$—, —$NR_2$—CO—, —CO—$NR_2$—, —O—CO—, —CO—O—, —O—$HCR_1$— or —$CHR_1$—O— group, in which $R_1$ is a hydrogen atom, a $C_{1-3}$-alkyl, phenyl-$C_{1-3}$-alkyl or phenyl group, $R_2$ is a hydrogen atom, a $C_{1-3}$-alkyl or phenyl-$C_{1-3}$-alkyl group and $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$ is a methine group, $X_2$ and $X_3$ are each a nitrogen atom, it additionally being optional in the abovementioned heterocylic rings in which $X_2$ and $X_3$ are each a nitrogen atom for a methylene group linked to a ring nitrogen atom to be replaced by a carbonyl group, B is a 3-piperidinylene, 4-piperidinylene or 1,4-piperazinylene group in which in each case a methylene group adjacent to a nitrogen atom is optionally replaced by a carbonyl group, it additionally being optional for a 1,4-piperazinylene group to be substituted by $R_b$ and $R_c$, and $R_b$ and $R_c$ being defined as mentioned above, or a phenylene, cyclohexylene or pyridazinylene group, D is an —O—$R_1CR_4$—CO—, —$NR_3$—$HCR_1$—CO—, —$NR_3$—$CH_2CH_2CO$—, —$CH_2CO$—, —$CHR_1CH_2CO$— or (—O—)$_2$CH—CO— group, in which $R_1$ and $R_3$ are defined as mentioned above and $R_4$ is a hydrogen atom, a $C_{1-3}$-alkyl, hydroxy-$C_{1-3}$-alkyl, carboxy-$C_{1-3}$-alkyl, $C_{1-3}$-alkoxycarbonyl-$C_{1-3}$-alkyl, $C_{3-7}$-cycloalkoxycarbonyl-$C_{1-3}$-alkyl, phenyl-$C_{1-3}$-alkyl, phenyl, pyridyl-$C_{1-3}$-alkyl or pyridyl group, and E is a hydroxyl, $C_{1-6}$-alkoxy, $C_{3-9}$-cycloalkoxy, phenyl-$C_{1-3}$-alkoxy or $R_7$—CO—O—($R_5CR_6$)—O— group, in which $R_5$ is a hydrogen atom, a $C_{1-6}$-alkyl, $C_{3-7}$-cycloalkyl or phenyl group, $R_6$ is a hydrogen atom or a $C_{1-6}$-alkyl group and $R_7$ is a $C_{1-5}$-alkyl, $C_{1-5}$-alkoxy, $C_{5-7}$-cycloalkyl or $C_{5-7}$-cycloalkoxy group, the expressions "a phenyl group" or "a phenylene group" mentioned in the definitions of the above radicals in each instance mean, respectively, either an unsubstituted phenyl or phenylene group or a phenyl or phenylene group which is mono-, di- or trisubstituted by fluorine, chlorine, bromine or iodine atoms, by $C_{1-3}$-alkyl, trifluoromethyl, nitro, amino, $C_{1-3}$-alkylamino, di($C_{1-3}$-alkyl)amino, $C_{1-4}$-alkanoylamino, hydroxyl, $C_{1-3}$-alkoxy, carboxyl, $C_{1-3}$-alkoxycarbonyl, $C_{3-7}$-cycloalkoxycarbonylalkoxy, hydroxycarbonyl-$C_{1-3}$-alkoxy, $C_{1-3}$-alkoxycarbonyl-$C_{1-3}$-alkoxy, aminocarbonyl, $C_{1-3}$-alkylaminocarbonyl or di($C_{1-3}$-alkyl)-aminocarbonyl groups, wherein, if there is more than one substituent, the substituents are identical or different, the esters of a natural α-amino acid are understood as meaning its $C_{1-6}$-alkyl, $C_{2-6}$-alkenyl, $C_{5-7}$-cycloalkyl, phenyl or phenyl-$C_{1-3}$-alkyl esters, the ethers of the side chain of a natural D- or L-α-amino acid are understood as meaning its $C_{1-5}$-alkyl, phenyl-$C_{1-3}$-alkyl, phenyl or $C_{4-7}$-cycoalkyl ether and a radical which is cleaved in vivo is understood as meaning an alkanoyl group having a total of 1 to 6 carbon atoms, a benzoyl, allyloxycarbonyl, $C_{1-5}$-alkoxycarbonyl or phenyl-$C_{1-3}$-alkoxycarbonyl group, or a tautomer or pharmaceutically acceptable salt thereof.

3. A compound of the formula I according to claim 1, in which $R_a$ is a hydrogen atom, a $C_{1-3}$-alkyl, phenyl-$C_{1-3}$-alkyl, $C_{1-5}$-alkoxycarbonyl or phenyl-$C_{1-3}$-alkoxycarbonyl group, $R_b$ and $R_c$, which are identical or different, are each a hydrogen atom or the side chain of a natural D- or L-α-amino acid, or its ester or ether, A is a —$CH_2CH_2$—, —CO—$CH_2$—, —$CH_2$—CO—, —$CH_2$—$NR_3$—, —$NR_3$—$CH_2$—, —NH—CO—, —O—CO— or —$CH_2$—O— group, in which $R_3$ is a hydrogen atom, a $C_{1-3}$-alkyl, phenyl-$C_{1-3}$-alkyl, $C_{1-3}$-alkylcarbonyl or $C_{1-5}$-alkylsulphonyl group, $X_1$ is a methine group, $X_2$ and $X_3$ are each a nitrogen atom, it additionally being optional in the abovementioned heterocylic rings in which $X_2$ and $X_3$ are each a nitrogen atom for a methylene group linked to a ring nitrogen atom to be replaced by a carbonyl group, B is a 4-piperidinylene group or a 1,4-piperazinylene group in which a methylene group adjacent to a nitrogen atom is optionally replaced by a carbonyl group, it additionally being optional for the abovementioned 1,4-piperazinylene groups to be substituted by a carboxymethyl or $C_{1-5}$-alkoxycarbonyl group, or is a 1,3- or 1,4-phenylene group which is optionally substituted by an E—CO—$CH_2$— group, E being defined as below, or a 1,4-cyclohexylene or 2,5-pyridazinylene group, D is an —O—$R_1CR_4$—O—, —$H_2CO$—, —$CHR_1CH_2CO$—,—$NR_3CH_2CO$— or (—O—)$_2$CH—CO— group, in which $R_3$ is defined as in claim 1, $R_1$ is a hydrogen atom or a $C_{1-3}$-alkyl group and $R_4$ is a hydrogen atom, a $C_{1-3}$-alkyl, hydroxy-$C_{1-2}$-alkyl, carboxymethyl, benzyl, chlorobenzyl or phenyl group, and E is a hydroxyl, $C_{1-6}$alkoxy, $C_{3-9}$-cycloalkoxy or phenyl-$C_{1-3}$-alkoxy group, the esters of a natural α-amino acid in the definition of the abovementioned radicals being understood as meaning its $C_{1-6}$-alkyl, $C_{2-6}$-alkenyl, $C_{5-7}$-cycloalkyl, phenyl or phenyl-$C_{1-3}$-alkyl esters and the ethers of the side chain of a natural D- or L-α-amino acid being understood as meaning its $C_{1-5}$-alkyl, phenyl-$C_{1-3}$-alkyl, phenyl or $C_{4-7}$-cycloalkyl ether, or a tautomer or pharmaceutically acceptable salt thereof.

4. A compound of the formula I according to claim 1, in which $R_a$ is a hydrogen atom, a benzyl, $C_{1-5}$-alkoxycarbonyl or benzyloxycarbonyl group, $R_b$ and $R_c$, which are identical or different, are each a hydrogen atom or the side chain of a natural D- or L-α-amino acid, or its ester or ether, A is a —CH$_2$CH$_2$—, —CO—CH$_2$—, —CH$_2$—CO—, —CH$_2$—NR$_3$—, —NR$_3$—CH$_2$— or —NH—CO— group, in which $R_3$ is a hydrogen atom, a methyl, benzyl, acetyl or n-butylsulphonyl group, $X_1$ is a methine group, $X_2$ and $X_3$ are each a nitrogen atom, it additionally being optional in the abovementioned heterocylic rings in which $X_2$ and $X_3$ are each a nitrogen atom for a methylene group linked to a ring nitrogen atom to be replaced by a carbonyl group, B is a 4-piperidinylene group or a 1,4-piperazinylene group in which a methylene group adjacent to a nitrogen atom is optionally replaced by a carbonyl group, it additionally being optional for the abovementioned 1,4-piperazinylene groups to be substituted by a carboxymethyl or $C_{1-5}$-alkoxycarbonyl group, or is a 1,3- or 1,4-phenylene group which is optionally substituted by an E—CO—CH$_2$— group, E being defined as below, or a 1,4-cyclohexylene or 2,5-pyridazinylene group, D is an —O—R$_1$CH—CO—, —O—(CH$_3$CCH$_3$)—CO—, —CH$_2$CH$_2$CO—, —(CHCH$_3$)CH$_2$CO—,—NR$_3$CH$_2$CO— or (—O—)$_2$CH—CO— group, in which $R_3$ is defined as in claim 1 and $R_1$ is a hydrogen atom, methyl, 2-hydroxyethyl, carboxymethyl, benzyl, chlorobenzyl or phenyl group, and E is a hydroxyl $C_{1-6}$-alkoxy, $C_{3-9}$-cycloalkoxy or phenyl-$C_{1-3}$-alkoxy group, the esters of a natural α-amino acid in the definition of the abovementioned radicals being understood as meaning its $C_{1-6}$-alkyl, $C_{2-6}$-alkenyl, $C_{5-7}$-cycloalkyl, phenyl or phenyl-$C_{1-3}$-alkyl esters and the ethers of the side chain of a natural D- or L-α-amino acid being understood as meaning its $C_{1-5}$-alkyl, phenyl-$C_{1-3}$-alkyl, phenyl or $C_{4-7}$-cycloalkyl ether, or a tautomer or pharmaceutically acceptable salt thereof.

5. A compound selected from the group consisting of:

(a) 1-(4-carboxymethyloxyphenyl)-4-[2-(piperidin-4-yl)ethyl]-piperazine, (b) 1-(4-carboxymethyloxyphenyl)-4-[2-(piperidin-4-yl)ethyl]-piperazin-2-one, (c) 1-[3,4-di(carboxymethyloxy)phenyl]-4-[2-(piperidin-4-yl)-ethyl]piperazine, (d) 1-(4-carboxymethyloxyphenyl)-2-methyl-4-[2-(piperidin-4-yl)ethyl]piperazine, (e) 1-(trans-4-carboxymethyloxycyclohexyl)-4-[2-(piperidin-4-yl)ethyl]-piperazin-2-one, (f) 1-[4-(1-carboxybenzyloxy)phenyl]-4-[2-(piperidin-4-yl)-ethyl]piperazine.

and their $C_{1-4}$-alkyl, cyclopentyl and cyclohexyl esters, and their pharmaceutically acceptable salts.

6. 1-(4-Cyclohexyloxycarbonylmethyloxyphenyl)-4-[2-(piperidin-4-yl)ethyl]piperazine or a pharmaceutically acceptable salt thereof.

7. 1-[3,4-Di(cyclopentyloxycarbonylmethyloxy)phenyl]-4-[2-(piperidin-4-yl)ethyl]piperazine or a pharmaceutically acceptable salt thereof.

8. A pharmaceutical composition comprising a compound in accordance with claim 1, 2, 3, 4, 5, 6, or 7.

9. A method for preventing the formation of venous and arterial thromboses which comprises administering, to a patient abnormally susceptible to the formation of a thrombus, an antithrombotic amount of a compound in accordance with claim 1, 2, 3, 4, 5, 6, or 7.

* * * * *